United States Patent
Goel et al.

(10) Patent No.: US 9,868,992 B2
(45) Date of Patent: Jan. 16, 2018

(54) TISSUE AND BLOOD-BASED MIRNA BIOMARKERS FOR THE DIAGNOSIS, PROGNOSIS AND METASTASIS-PREDICTIVE POTENTIAL IN COLORECTAL CANCER

(71) Applicants: Ajay Goel, Dallas, TX (US); Keun Hur, Dallas, TX (US); Yuji Toiyama, Dallas, TX (US); C. Richard Boland, Dallas, TX (US)

(72) Inventors: Ajay Goel, Dallas, TX (US); Keun Hur, Dallas, TX (US); Yuji Toiyama, Dallas, TX (US); C. Richard Boland, Dallas, TX (US)

(73) Assignee: Baylor Research Institute, Dallas, TX (US)

( * ) Notice: Subject to any disclaimer, the term of this patent is extended or adjusted under 35 U.S.C. 154(b) by 92 days.

(21) Appl. No.: 14/215,959

(22) Filed: Mar. 17, 2014

(65) Prior Publication Data
US 2014/0322354 A1 Oct. 30, 2014

Related U.S. Application Data

(60) Provisional application No. 61/793,302, filed on Mar. 15, 2013.

(51) Int. Cl.
*C12Q 1/68* (2006.01)
*A61B 1/31* (2006.01)

(52) U.S. Cl.
CPC .............. *C12Q 1/6886* (2013.01); *A61B 1/31* (2013.01); *C12Q 2600/178* (2013.01)

(58) Field of Classification Search
None
See application file for complete search history.

(56) References Cited

U.S. PATENT DOCUMENTS

| | | | |
|---|---|---|---|
| 2010/0203513 A1* | 8/2010 | Ju | C12Q 1/6886 435/6.16 |
| 2010/0298151 A1* | 11/2010 | Taylor | C12Q 1/6809 506/2 |
| 2011/0287020 A1* | 11/2011 | Gruber | A61K 38/2292 424/155.1 |
| 2012/0045768 A1* | 2/2012 | Arunachalam | C12Q 1/6813 435/6.12 |
| 2012/0088687 A1 | 4/2012 | Goel et al. | |
| 2012/0184453 A1 | 7/2012 | Wang et al. | |
| 2012/0231970 A1 | 9/2012 | Nakagama et al. | |

FOREIGN PATENT DOCUMENTS

| WO | WO 2007/081740 | 7/2007 |
|---|---|---|
| WO | WO 2009/059026 | 5/2009 |
| WO | WO 2009/080437 | 7/2009 |
| WO | WO 2009/111643 | 9/2009 |
| WO | WO 2011/076142 | 6/2011 |
| WO | WO 2012/097069 | 7/2012 |
| WO | WO 2012/128902 | 9/2012 |

OTHER PUBLICATIONS

Lu et al, Nature 435: 834 (2005).*
Gui et al, Clinical Science 120: 183 (2011).*
Siu Chi Lam, "Identification of microRNA 885-5p as a Novel Regulator of Tumor Metastasis in Colorectal Cancer," Cancer Research (2011) vol. 71, No. 8, Supplement 1, Abstract 3979 (3 pages).
Amaia Lujambio et al., "Genetic Unmasking of an Epigenetically Silenced microRNA in Human Cancer Cells," Cancer Research (2007) vol. 67, No. 4, pp. 1424-1429.
International Search Report and Written Opinion of the International Searching Authority for PCT/US2014/030407 dated Aug. 22, 2014 (18 pages).
Extended Search Report by the European Patent Office for application No. EP 14 76 4952 dated Sep. 21, 2016.
Office Action issued in European Application No. 14764952, dated Oct. 17, 2017.

* cited by examiner

*Primary Examiner* — James Martinell
(74) *Attorney, Agent, or Firm* — Norton Rose Fulbright US LLP

(57) ABSTRACT

Methods and compositions for the diagnosis, prognosis and classification of cancer, especially colorectal cancer, are provided. For example, in certain aspects methods for cancer prognosis using expression or methylation analysis of selected biomarkers are described. Particular aspects of the present invention may include methods and biomarkers for diagnosing or detecting colorectal cancer or metastasis in a subject by measuring a level of expression of biomarker miRNA such as miR-885-5p in the sample from the subject and evaluating the risk of developing cancer or metastasis in the subject.

9 Claims, 35 Drawing Sheets

GOOD PROGNOSIS miRNAs IN LOW EXPRESSION

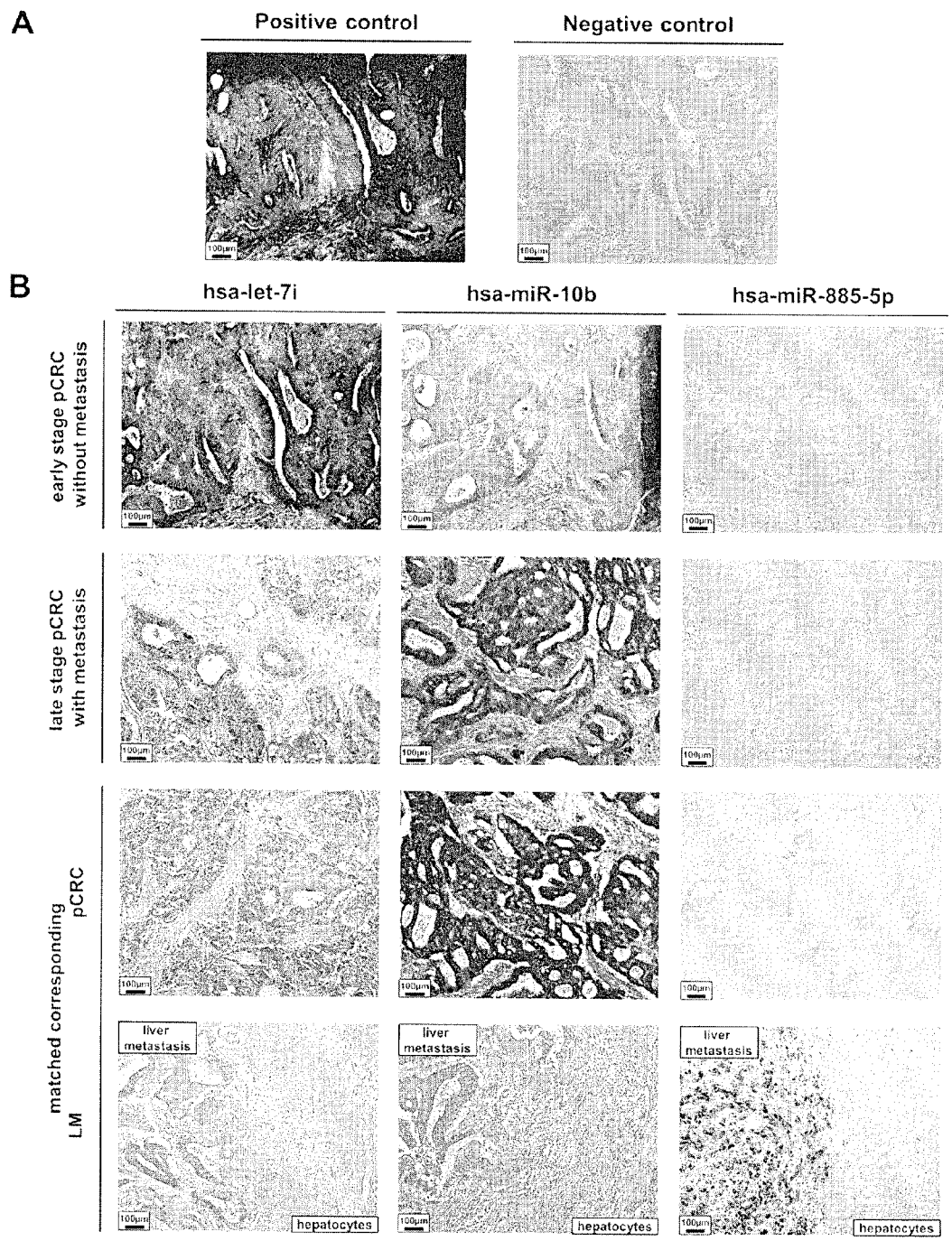
FIGS. 8 (A-B)

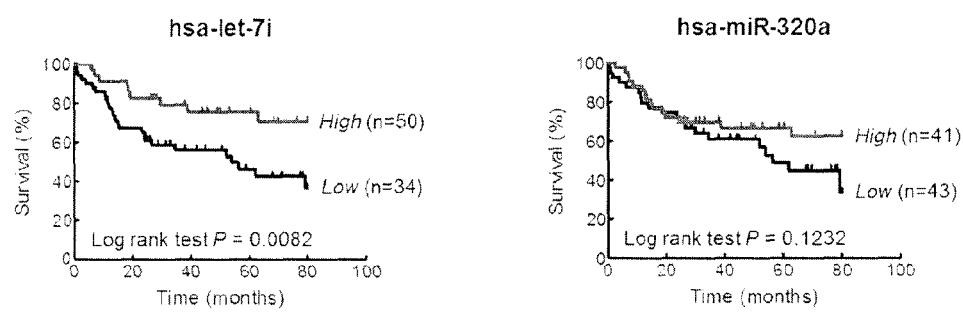
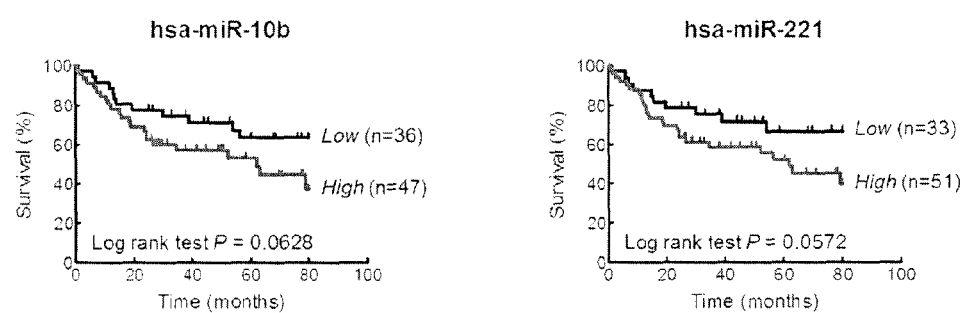
FIGS. 9 (A-B)

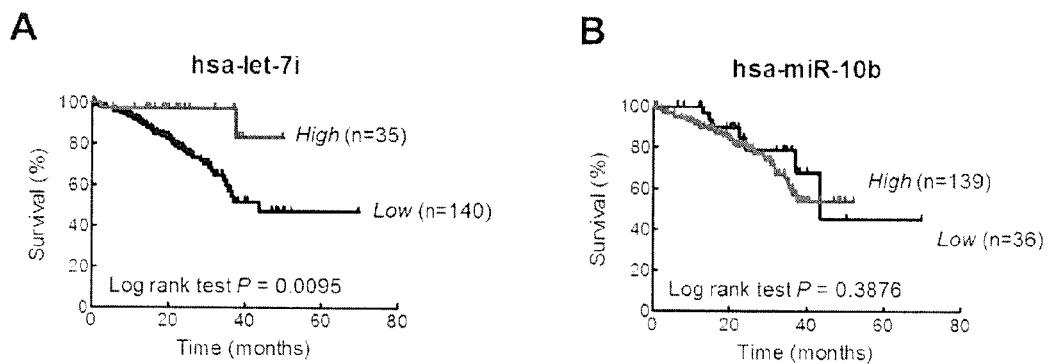
FIGS. 10 (A-B)
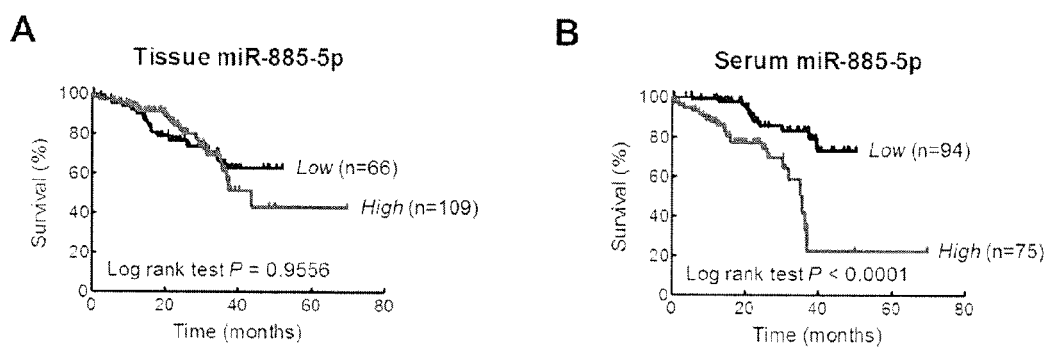
FIGS. 11 (A-B)

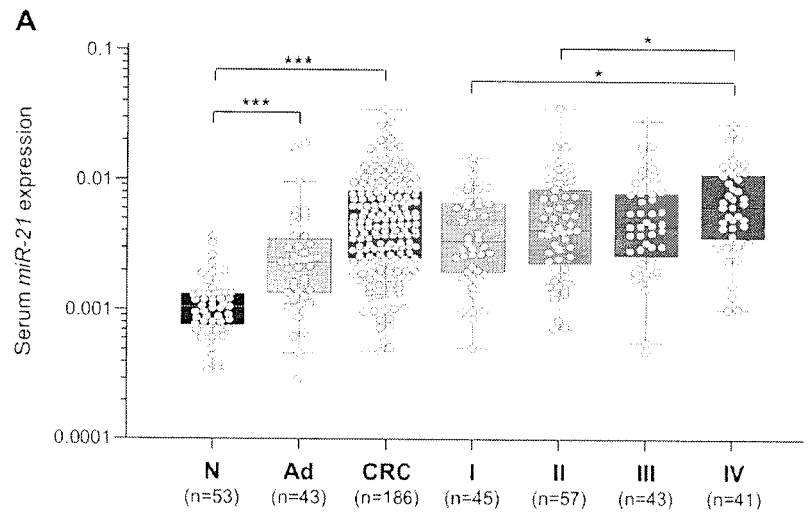
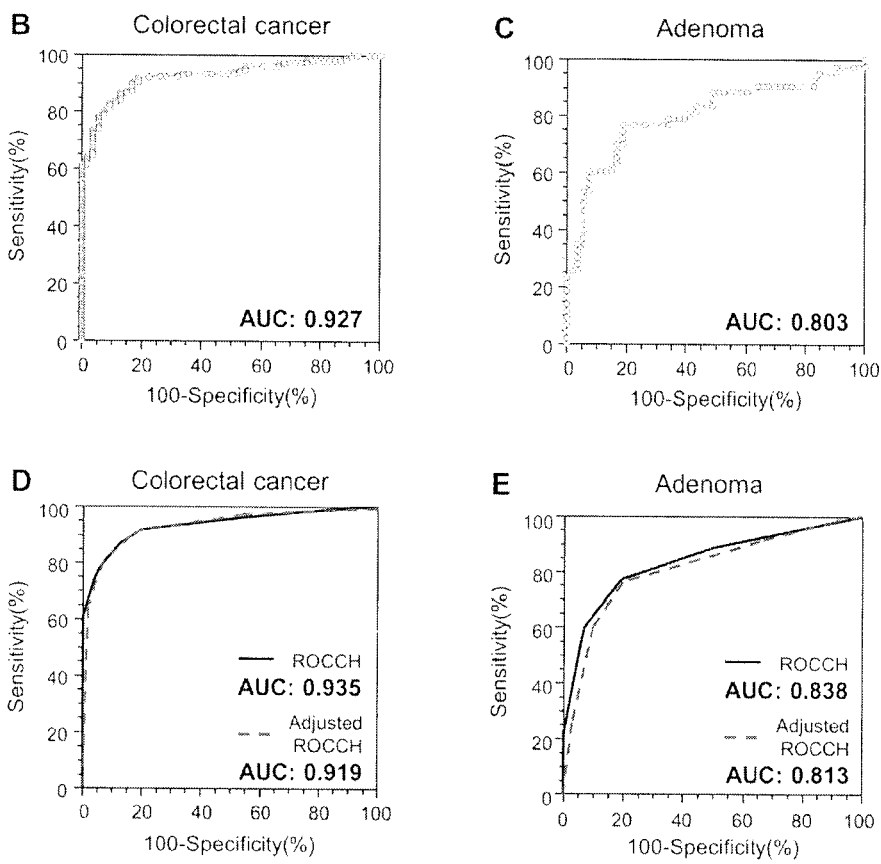
FIGS. 14A-14E

A

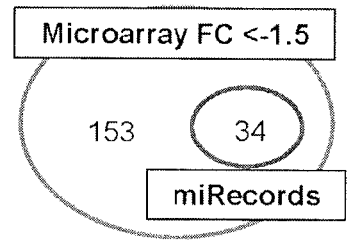

B

| Lovo miR124 | HT29 miR124 | HCT116 miR124 | Lovo control | HT29 control | HCT116 control | Regulation | FC | ILMN Gene |
|---|---|---|---|---|---|---|---|---|
| -1.50355 | | -1.8355937 | 0 | | 0 | down | -3.1812 | STOM |
| -1.9602504 | -1.38637 | -1.5570235 | 0 | 0 | 0 | down | -3.1049 | C9ORF23 |
| -1.2840428 | -1.1265025 | -1.2505958 | 0 | 0 | 0 | down | -2.33008 | CTNND1 |
| -1.2549028 | -1.034699 | -1.1226134 | 0 | 0 | 0 | down | -2.19985 | PAPSS2 |
| -0.92489576 | -1.2386703 | -1.1174035 | 0 | 0 | 0 | down | -2.13414 | ASCC3 |
| -0.93617296 | -0.92775106 | -1.3520255 | 0 | 0 | 0 | down | -2.10232 | AP1M2 |
| -0.8253598 | -0.93581915 | -1.2700272 | 0 | 0 | 0 | down | -2.01447 | PGM2 |
| -0.9953208 | -1.0851958 | -0.7414923 | 0 | 0 | 0 | down | -1.91942 | QSER1 |
| -0.99262094 | -0.8399334 | -0.8317342 | 0 | 0 | 0 | down | -1.85073 | DNM2 |
| -0.91982317 | -0.8449731 | -0.8614702 | 0 | 0 | 0 | down | -1.83454 | C11ORF82 |
| -0.98311996 | -0.88323116 | -0.6616845 | 0 | 0 | 0 | down | -1.79338 | JAZF1 |
| -0.8982897 | -0.648211 | -0.81754684 | 0 | 0 | 0 | down | -1.7267 | G3BP2 |
| -0.9472928 | -0.740118 | -0.6703024 | 0 | 0 | 0 | down | -1.72417 | NEK6 |
| -0.6982908 | -0.63626623 | -0.9484844 | 0 | 0 | 0 | down | -1.69468 | FRMD8 |
| -0.81918335 | -0.64198494 | -0.81426764 | 0 | 0 | 0 | down | -1.69171 | STEAP3 |
| -0.5861783 | -0.7441535 | -0.9401984 | 0 | 0 | 0 | down | -1.68979 | GNPDA2 |
| -0.76777315 | -0.7471242 | -0.6883445 | 0 | 0 | 0 | down | -1.66372 | TSPAN6 |
| -0.7029276 | -0.62951946 | -0.87010384 | 0 | 0 | 0 | down | -1.66346 | *PPM1F* |
| -0.8419008 | -0.5779166 | -0.7501354 | 0 | 0 | 0 | down | -1.65097 | CHSY1 |
| -0.7421942 | -0.60307837 | -0.8228903 | 0 | 0 | 0 | down | -1.65029 | RAD17 |
| -0.7808418 | -0.717751 | -0.6477165 | 0 | 0 | 0 | down | -1.64198 | SLC10A7 |
| -0.61890984 | -0.7884271 | | 0 | 0 | 0 | down | -1.62864 | MAPK14 |
| -0.74278927 | -0.6908121 | -0.6741457 | 0 | 0 | 0 | down | -1.62742 | ACADVL |
| -0.67155266 | -0.6556754 | -0.7504463 | 0 | 0 | 0 | down | -1.61615 | CAPNS1 |
| -0.6987629 | -0.5431714 | -0.80576324 | 0 | 0 | 0 | down | -1.60499 | ANKLE2 |
| -0.6229024 | -0.5847707 | -0.78558445 | 0 | 0 | 0 | down | -1.58493 | SLC44A2 |
| -0.6542163 | -0.7031274 | -0.62140036 | 0 | 0 | 0 | down | -1.57962 | NFKBIZ |
| -0.63898754 | -0.6890788 | -0.6490631 | 0 | 0 | 0 | down | -1.57903 | G3BP2 |
| -0.54682446 | -0.6794915 | -0.7328901 | 0 | 0 | 0 | down | -1.57251 | LRRC1 |
| -0.5427475 | -0.6146951 | -0.78368664 | 0 | 0 | 0 | down | -1.56596 | *MAPRE1* |
| -0.6079855 | -0.7639322 | -0.50810003 | 0 | 0 | 0 | down | -1.544 | ARL5B |
| -0.6399822 | -0.5800967 | -0.6357374 | 0 | 0 | 0 | down | -1.53539 | EIF3B |
| -0.6291783 | -0.5594621 | | 0 | 0 | 0 | down | -1.50976 | NAV2 |
| -0.6400187 | | -0.54367614 | 0 | | 0 | down | -1.50718 | FAM134B |

FIGS 29A-29B

TISSUE AND BLOOD-BASED MIRNA BIOMARKERS FOR THE DIAGNOSIS, PROGNOSIS AND METASTASIS-PREDICTIVE POTENTIAL IN COLORECTAL CANCER

This application is a utility application claiming priority to U.S. Provisional Patent Application No. 61/793,302, filed Mar. 15, 2013, the contents of which are hereby incorporated by reference in its entirety.

The invention was made with government support under Grant Nos. R01 CA72851 and CA129286 awarded by the National Institutes of Health (NIH). The government has certain rights in the invention.

BACKGROUND OF THE INVENTION

1. Field of the Invention

The present invention relates generally to the fields of oncology, molecular biology, cell biology, and cancer. More particularly, it concerns cancer diagnosis, prognosis or classification using molecular markers.

2. Description of Related Art

Colorectal cancer (CRC) is one of the most common malignancies worldwide, and is a major cause of cancer-related deaths (Siegel 2012). Survival rates of patients with CRC have increased in the past few years, possibly as a result of earlier diagnosis and improved treatment regimens, nonetheless, approximately 30-50% of patients who undergo curative resection subsequently experience local tumor recurrence or metastasis (Lieberman 2012). This subgroup of patients usually receive chemotherapy often in combination with monoclonal antibody therapy, with a median overall survival duration of ~20 months, and the response rates at best around 50% (Halama 2008). However, the substantial financial costs associated with CRC treatment not only present an economic burden, but treatment of all patients with chemotherapy without a priori selection leads to overtreatment of patients with toxic agents that produce severe adverse effects (Meropol 2007). In order to overcome this clinical challenge, there is a clear need to identify biomarkers that will facilitate the identification of patients with a poor prognosis, and permit personalized treatment strategies for patients with high risk of CRC recurrence.

Blood-based tumor markers are gaining acceptance as a potential alternative for noninvasive detection of cancer. Serum carcinoembryonic antigen (CEA) is one marker that is frequently used for predicting prognosis in patients with CRC (Duffy 2007; Reiter 2000). Unfortunately, CEA levels do not always correlate with the presence of metastasis, and the incidence of false-positive and false-negative results are very high (Fakih 2006; Tan 2009). Consequently, there is a dire need to identify highly robust biomarkers that can clinically determine cancer prognosis, and are better indicators of patient outcome than the existing TNM staging system or other conventional tumor markers of CRC (Duffy 2001).

MicroRNAs (miRNAs) are non-coding RNA molecules of approximately 21-23 nucleotides in length that regulate target gene expression by interfering with their transcription or by inhibiting translation (Cortez 2009). miRNAs play crucial roles in diverse cellular biological processes, including differentiation, proliferation, growth, migration and survival. The discovery that miRNA expression is frequently dysregulated in malignant tumors underpins their critical role, which is a matter of active investigation, both from a basic science perspective and for its clinical usefulness (van Kouwenhove 2011). Recently, several studies have highlighted the diagnostic and prognostic utility of plasma and serum-based miRNA levels, because tumor-derived miRNAs are present in human circulation in remarkably stable forms that are protected from endogenous ribonuclease activity (Mitchell 2008). These reports suggest that plasma/serum miRNA-based assays may constitute accurate methods for diagnosis and prognosis of human cancer, although to date only a few studies have specifically addressed the clinical significance of circulating miRNAs in patients with CRC (Ng 2009; Huang 2010; Wang 2012; Pu 2010; Cheng 2011).

Distant metastasis is the major cause of serious morbidity and mortality in cancer patients. Liver metastasis is the most common manifestation, and occurs in >50% of CRC patients with metastases.[2] Aggressive liver resection in metastatic CRC patients may improve the 5-year survival, but most of these patients still experience tumor recurrence (Rees 2008; Fernandez 2004). Although current diagnostic imaging tools such as contrast enhanced computed tomography (CT), positron emission tomography-CT (PET-CT), and magnetic resonance imaging (MRI) can facilitate the detection of CRC metastasis (Bipat 2007), these modalities are of limited value because of the inability to identify truly early metastatic lesions and the costs associated with advanced imaging. In view of this clinical challenge, there is a clear need for the development of metastasis-specific molecular biomarkers that can help predict outcomes and direct more effective therapies.

However, despite many attempts to establish prognostic, diagnostic or metastatic markers to understand the clinical biology of patients with colorectal cancer, validated clinical or biomarker parameters are lacking in many aspects. Therefore, there remains a need to discover novel prognostic, diagnostic or metastatic markers for cancer patients, especially colorectal cancer patients.

SUMMARY OF THE INVENTION

In certain aspects, biomarkers may be used for the detection or assessment of pathologies, including, but not limited to all stages of cancer, such as colorectal cancer.

Certain embodiments may comprise methods for evaluating a colorectal cancer such as a primary colorectal cancer in a patient suspected of having or determined to have a colorectal cancer such as primary colorectal cancer, or providing a prognosis or diagnosis for the patient. The methods may provide a clinician with information useful for screening, examination, surveillance, diagnosis and/or treatment options. Methods may involve identifying a patient suspected of having or determined to have a colorectal cancer such as primary colorectal cancer.

The methods may further include determining or measuring in a sample from the patient expression levels of one, two, three, four, five, six, seven, eight, nine, or more biomarker miRNA such as miR-21, miR-31, miR124, miR-200c, miR-203, miR-885-5p, let-7i, miR-10b, miR-320a, and/or miR221. The measuring may also include measuring methylation levels of one or more genes encoding biomarker miRNA such as miR124, miR-200c and/or miR-203.

In further embodiments, the methods may comprise measuring expression levels of miR-885-5p as the single miRNA biomarker or in combination with one of more miRNA biomarkers described herein. In particular embodiments, the sample may be a blood sample or serum sample. In other aspects, the sample may be a tissue sample.

In further aspects, the miR-885-5p marker may be measured in a blood sample or serum sample or any sample from a circulation system. In particular embodiments, methods may involve measuring the expression of one or more markers, such as miR-21, miR-31, miR-200c, miR-203 and/or miR-885-5p in a serum sample or any sample from a circulation system. In further embodiments, methods may also include measuring the expression of one or more markers, such as miR-124, let-7i, miR-10b, miR-320a, and/or miR-221 or the methylation of a gene encoding miR-124, miR-200c, and/or miR-203 in a tissue sample.

In further embodiments, the methods may comprise determining a risk associated with colorectal cancer in the patient based on the level of expression compared to a control or reference level for the biomarker. In particular aspects, the risk may be a risk for dysplasia, cancer or metastasis, or more particularly, distant metastasis. In further aspects, the risk may be a risk of having or developing cancer, of having a poor prognosis, of having poor survival probability, or developing tumor recurrence or metastasis, or a combination thereof. The risk may be a risk of developing liver metastasis. In further aspects, the risk may be a risk of developing distant metastasis.

The methods may comprise determining the patient as having a high or significant risk, such as a poor diagnosis or prognosis or a high metastasis risk by having increased expression level of miR-885-5p or increased expression levels in one or more of miR-21, miR-31, miR-124, miR-200c, miR-203, miR-885-5p, miR-10b, and/or miR-221 or deceased expression levels of miR-124, let-7i, and 320a compared to a control or reference expression level, or an increased methylation level of a gene encoding miR-124 compared to a control or reference methylation level. In the other aspects, the method may comprise determining the patient as having a low risk, such as a favorable diagnosis or prognosis or a low metastasis risk by having decreased expression levels in a biomarker comprising miR-21, miR-31, miR-124, miR-200c, miR-203, miR-885-5p, miR-10b, and/or miR-221 or increased expression levels of miR-124, let-7i, and 320a compared to a control or reference expression level.

In certain aspects, the expression or methylation levels of the biomarker in the sample may be compared to a control or reference levels for the biomarker. The increased or decreased expression or methylation n levels with respect to reference levels or control may be indicative of a high risk of colorectal dysplasia, cancer, or metastasis. The control may be a normal tissue, a non-cancerous tissue, a pre-cancer tissue, a primary tumor tissue, a non-dysplastic tissue, a non-metastasized tissue, or the same tissue taken at a point in time before the patient develops dysplasia, cancer or any stages of cancer, or metastasis or from patients with poor or favorable prognosis or diagnosis. The reference level can be expression or methylation levels of any of the controls or an average of a population of controls or expression or methylation levels of a different gene or miRNA taken from the same tissue or a different tissue whose expression or methylation level does not change, for example in developing dysplasia, cancer, metastasis. In some embodiments, methods involve comparing the level of expression or methylation of at least one biomarker miRNA to the level of expression or methylation level of a comparative miRNA to determine a biomarker difference value. A "comparative miRNA" refers to a miRNA whose expression level is used to evaluate the level of another miRNA in the sample; in some embodiments, the expression level of a comparative miRNA is used to evaluate a biomarker miRNA expression level.

In some embodiments, a level of miRNA is increased or decreased compared to a control or reference level if it is at least 20, 30, 40, 50, 60, 80, 90, 100, 110, 120, 130, 140, 150, 160, 170, 180, 190, 200, 250, 300, 350, 400, 450, 500, 600, 700, 800, 900, or 1000% higher (or any range derivable therein) than the reference or control level. This may or may not include using a standardized or normalized level of expression in determining whether there is an increase or decrease. The level may be an expression level of the miRNA or methylation level of the encoding gene.

Embodiments also concern methods and compositions that can be used for detecting colorectal cancer, differentiating colorectal cancer, distinguishing colorectal cancer, colorectal cancer as a high risk lesion, identifying colorectal cancer as a low/high risk metastasis, identifying tissue having colorectal cancer as a target for surgical resection or intensive or frequent surveillance, determining tissue having colorectal cancer that should not be surgically resected, categorizing colorectal cancer, diagnosing colorectal cancer, providing a prognosis to a patient regarding colorectal cancer, evaluating management, surveillance or treatment options for colorectal cancer, or treating a patient with colorectal cancer.

In some embodiments, methods involve measuring or determining in a sample from the patient that the sample has increased expression levels in a biomarker comprising miR-21, miR-31, miR-200c, miR-203, miR-885-5p, miR-10b, and/or miR-221 or deceased expression levels of miR-124, let-7i, and 320a compared to a control or reference expression level for the gene and identifying the patient as being at a significant risk for developing colon dysplasia, cancer, or metastasis compared to the overall risk for normal people or patients without colorectal dysplasia or cancer or patients with colorectal dysplasia or cancer.

In further embodiments, methods involve managing a patient suspected of having or determined to have a colorectal cancer such as primary colorectal cancer by measuring the expression of miR-21, miR-31, miR124, miR-200c, miR-203, miR-885-5p, let-7i, miR-10b, miR-320a, and/or miR221 in a sample, and monitoring and/or treating the patient for colorectal cancer or metastasis if the patient exhibits one or more characterizes including: increased expression level of miR-885-5p or increased expression levels in one or more of miR-21, miR-31, miR-124, miR-200c, miR-203, miR-885-5p, miR-10b, and/or miR-221 or deceased expression levels of miR-124, let-7i, and 320a compared to a control or reference expression level, or an increased methylation level of a gene encoding miR-124 compared to a control or reference methylation level. For example, the monitoring may comprise intensive or frequent surveillance to the patient, such as comprising performing a colonoscopy on the patient after a sample from the patient is evaluated.

There may also be provided methods for managing or treating or preventing a colorectal cancer or metastasis. The methods may comprise identifying the patient as being suspected of having or determined to have a colorectal cancer and having one or more of the following: increased expression level of miR-885-5p or increased expression levels in one or more of miR-21, miR-31, miR-124, miR-200c, miR-203, miR-885-5p, miR-10b, and/or miR-221 or deceased expression levels of miR-124, let-7i, and 320a compared to a control or reference expression level, or an increased methylation level of a gene encoding miR-124 compared to a control or reference methylation level. The methods may further comprise developing a management plan or administering a preventive procedure, screening, further diagnosis, examination, monitoring, surveillance plan or treatment to the identified patient based on the different levels.

In a particular embodiment, the methods may comprise administering a preventive procedure or treatment that inhibits or reduces the expression levels of one or more markers of miR-21, miR-31, miR-124, miR-200c, miR-203, miR-885-5p, miR-10b, and/or miR-221 and/or a preventive procedure or treatment that increases or promotes the expression levels of one or more markers of miR-124, let-7i, and 320a.

These methods can be implemented involving steps and compositions described below in different embodiments. In certain embodiments, methods and compositions for isolating, enriching, and/or labeling miRNA molecules and for preparing and using arrays or other detection techniques for miRNA analysis may refer to U.S. Pat. No. 7,919,245 (incorporated herein by reference).

In certain aspects, methods involve obtaining a sample of a subject or a patient or obtaining a sample from the subject or patient. The term subject or patient may refer to an animal (for example a mammal), including but not limited to humans, non-human primates, rodents, dogs, or pigs. The methods of obtaining provided herein include methods of biopsy such as fine needle aspiration, core needle biopsy, vacuum assisted biopsy, incisional biopsy, excisional biopsy, punch biopsy, shave biopsy or skin biopsy. In particular embodiments, methods involve obtaining a serum sample or tissue sample. The tissue sample may be a rectal, cecum, or colon tissue sample or any sample of a large intestine.

In certain embodiments the sample is obtained from a biopsy from rectal, cecum, or colon tissue by any of the biopsy methods previously mentioned. In other embodiments the sample may be obtained from any of the tissues provided herein that include but are not limited to gall bladder, skin, heart, lung, breast, pancreas, liver, muscle, kidney, smooth muscle, bladder, intestine, brain, prostate, esophagus, or thyroid tissue.

Alternatively, the sample may include but not be limited to blood, serum, sweat, hair follicle, buccal tissue, tears, menses, urine, feces, or saliva. In particular embodiments, the sample may be a tissue sample, a whole blood sample, a urine sample, a saliva sample, a serum sample, a plasma sample or a fecal sample.

In certain aspects the sample is obtained from cystic fluid or fluid derived from a tumor or neoplasm. In yet other embodiments the cyst, tumor or neoplasm is in the digestive system. In certain aspects of the current methods, any medical professional such as a doctor, nurse or medical technician may obtain a biological sample for testing. In further aspects of the current methods, the patient or subject may obtain a biological sample for testing without the assistance of a medical professional, such as obtaining a whole blood sample, a urine sample, a fecal sample, a buccal sample, or a saliva sample.

In further embodiments, the sample may be a fresh, frozen or preserved sample or a fine needle aspirate. In particular embodiments, the sample is a formalin-fixed, paraffin-embedded (FFPE) sample. An acquired sample may be placed in short term or long term storage by placing in a suitable medium, excipient, solution, or container. In certain cases storage may require keeping the sample in a refrigerated, or frozen environment. The sample may be quickly frozen prior to storage in a frozen environment. In certain instances the frozen sample may be contacted with a suitable cryopreservation medium or compound. Examples of cryopreservation mediums or compounds include but are not limited to: glycerol, ethylene glycol, sucrose, or glucose.

Some embodiments further involve isolating nucleic acids such as ribonucleic or RNA from a biological sample. Other steps may or may not include amplifying a nucleic acid in a sample and/or hybridizing one or more probes to an amplified or non-amplified nucleic acid. In certain embodiments, a microarray may be used to measure or assay the level of miRNA expression in a sample.

There may also be provided methods for assaying nucleic acids in the sample. Measuring or assaying for expression levels of an miRNA can be accomplished by a variety of different chemical and/or enzymatic reactions that are well known to those of skill in the art. In certain embodiments, methods may involve, but not be limited to, next generation sequencing, single-molecule real-time sequencing, mass spectrometry, digital color-coded barcode technology analysis, microarray expression profiling, quantitative PCR, reverse transcriptase PCR, reverse transcriptase real-time PCR, quantitative real-time PCR, end-point PCR, multiplex end-point PCR, cold PCR, ice-cold PCR, in situ hybridization, Northern hybridization, hybridization protection assay (HPA), branched DNA (bDNA) assay, rolling circle amplification (RCA), single molecule hybridization detection, invader assay, and/or Bridge Litigation Assay.

Measuring or assaying for methylation levels of a miRNA can be accomplished by a variety of different chemical and/or enzymatic reactions that are well known to those of skill in the art, including, but not limited to, next generation sequencing, single-molecule real-time sequencing, mass spectrometry, bisulfite sequencing, combined bisulfite restriction analysis (COBRA), Southern blotting, single nucleotide primer extension (SNuPE), methylation-specific PCR (MSPCR), restriction landmark genomic scanning for methylation (RLGS-M), HpaII-tiny fragment enrichment by ligation-mediated PCR (HELP assay), CpG island microarray, ChIP-chip (chromatin immunuprecipitation-on-chip), ChIP-seq (chromatin immunoprecipitation-sequencing), methylated DNA immunoprecipitation (MeDIP), or a microarray-based methylation profiling.

Methods may further involve recording the expression levels, risk, diagnosis, or prognosis in a tangible medium, reporting it to the patient, a health care payer, a physician, an insurance agent, or an electronic system, monitoring the patient for colorectal dysplasia, cancer, or metastasis, and/or comprising determining or administering a further screening, examination, monitoring, surveillance, or treatment for the patient based on the expression levels, risk, diagnosis or prognosis within one hour, one day, one week, one month, one year, two years, three years, four years, five years of the measuring or evaluating or within any intermediate time values or ranges.

There may be provided methods to perform intensive or frequent surveillance to the patient for colorectal dysplasia, cancer, or metastasis or administering a prevention or treatment for colorectal dysplasia, cancer, or metastasis if the patient has a high risk based on expression levels. Some further embodiments involve normal surveillance for colorectal dysplasia, cancer, or metastasis or administering a colorectal dysplasia, cancer, or metastasis prevention or treatment if the patient does not have a high risk based on expression levels. The treatment may comprise inhibiting or reducing the expression levels of the biomarkers or any traditional cancer therapies, such as surgery, chemotherapy, radiation, gene therapy, or immunotherapy for patients with risks determined based on the biomarker expression levels.

Further embodiments involve methods of managing a patient suspected of having or determined to have a colorectal cancer in a patient. The methods may comprise monitoring by performing colonoscopy or other testing methods, or treating the patient for colorectal cancer or metastasis after the patient has been determined to have increased expression of miR-885-5p or any miRNA different levels described herein, or a combination thereof.

In other embodiments, there may be a series of evaluations performed on a sample, for instance, in some embodiments, the cyst or tumor or biopsy may first undergo cytological examination or evaluation prior to implementing any molecular tests.

In some embodiments, methods will involve determining or calculating a diagnostic or risk score based on data concerning the expression level of one or more miRNAs, meaning that the expression level of the one or more miRNAs is at least one of the factors on which the score is based. A diagnostic score will provide information about the biological sample, such as the general probability that the patient is at high or significant risk for developing dysplasia or cancer, or is at low risk for developing dysplasia or cancer, or both.

In some embodiments, the diagnostic score represents the probability that the patient is more likely than not either at high or low risk for dysplasia, cancer or metastasis. In certain embodiments, a probability value is expressed as a numerical integer or number that represents a probability of 0% likelihood to 100% likelihood that a patient has a particular category of cancer, dysplasia, metastasis, or risk, such as high risk or low risk for dysplasia, cancer or metastasis. Yet further, the probability value is used to predict a patient that is at risk for development of metastasis or a patient that is at risk for development of colon cancer.

In some embodiments, the probability value is expressed as a number that represents a probability of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% likelihood (or any range derivable therein) that a patient has a particular category of cancer, dysplasia, metastasis or risk, such as at risk for having or deleoping dysplasia, cancer or metastasis. Alternatively, the probability may be expressed generally in percentiles, quartiles, or deciles.

A difference between or among weighted coefficients or expression levels or between or among the weighted comparisons may be, be at least or be at most about 0.1, 0.2, 0.3, 0.4, 0.5, 0.6, 0.7, 0.8, 0.9, 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 times or -fold (or any range derivable therein).

In some embodiments, determination of calculation of a diagnostic, prognostic, or risk score is performed by applying classification algorithms based on the expression values of biomarkers with differential expression p values of about, between about, or at most about 0.005, 0.006, 0.007, 0.008, 0.009, 0.01, 0.011, 0.012, 0.013, 0.014, 0.015, 0.016, 0.017, 0.018, 0.019, 0.020, 0.021, 0.022, 0.023, 0.024, 0.025, 0.026, 0.027, 0.028, 0.029, 0.03, 0.031, 0.032, 0.033, 0.034, 0.035, 0.036, 0.037, 0.038, 0.039, 0.040, 0.041, 0.042, 0.043, 0.044, 0.045, 0.046, 0.047, 0.048, 0.049, 0.050, 0.051, 0.052, 0.053, 0.054, 0.055, 0.056, 0.057, 0.058, 0.059, 0.060, 0.061, 0.062, 0.063, 0.064, 0.065, 0.066, 0.067, 0.068, 0.069, 0.070, 0.071, 0.072, 0.073, 0.074, 0.075, 0.076, 0.077, 0.078, 0.079, 0.080, 0.081, 0.082, 0.083, 0.084, 0.085, 0.086, 0.087, 0.088, 0.089, 0.090, 0.091, 0.092, 0.093, 0.094, 0.095, 0.096, 0.097, 0.098, 0.099, 0.1, 0.2, 0.3, 0.4, 0.5, 0.6, 0.7, 0.8, 0.9 or higher (or any range derivable therein). In certain embodiments, the diagnostic score is calculated using one or more statistically significantly differentially expressed biomarkers (either individually or as difference pairs).

Any of the methods described herein may be implemented on tangible computer-readable medium comprising computer-readable code that, when executed by a computer, causes the computer to perform one or more operations. In some embodiments, there is a tangible computer-readable medium comprising computer-readable code that, when executed by a computer, causes the computer to perform operations comprising: receiving information corresponding to the level of expression of a first biomarker comprising miR-885-5p in a serum sample of a patient suspected of having or determined to have a colorectal cancer such as primary colorectal cancer; and determining a difference value in the expression level using the information corresponding to the expression level in the serum sample compared to a control or reference level.

In some embodiments, receiving information comprises receiving from a tangible data storage device information corresponding to the expression or methylation levels from a tangible storage device. In additional embodiments the medium further comprises computer-readable code that, when executed by a computer, causes the computer to perform one or more additional operations comprising: sending information corresponding to the difference value to a tangible data storage device, calculating a risk score for the patient of developing dysplasia or cancer or metastasis, developing a management performing intensive or frequent surveillance to the patient for colorectal dysplasia or cancer or metastasis or administering a dysplasia or cancer or metastasis prevention or treatment if the patient has a high risk, and/or or performing normal surveillance for colorectal dysplasia or cancer or metastasis or administering a less aggressive or conventional prevention or treatment for dysplasia or cancer or metastasis if the patient does not have a high risk.

Also provided are kits containing the disclosed compositions or compositions used to implement the disclosed methods. In some embodiments, kits can be used to evaluate one or more miRNA molecules. In certain embodiments, a kit contains, contains at least, or contains at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more, or any range and combination derivable therein, miRNA probes or primers including those that may specifically hybridize under stringent conditions to miRNAs disclosed herein. In other embodiments, kits or methods may involve 1, 2, or more miRNA probes or primers, which may be capable of specifically detecting any biomarkers for methylation or expression.

Other objects, features and advantages of the invention will be apparent from the following details description. It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. As used herein, the phrase "consisting essentially of" limits the scope of a claim to the specified materials or steps and those that do not materially affect the basic and novel characteristic(s) of the claimed invention. As used herein, the phrase "consisting of" excludes any element, step, or ingredient not specified in the claim except for, e.g., impurities ordinarily associated with the element or limitation.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is impairment in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 8A-8B)—In situ expression of CRC metastasis-specific miRNAs (let-7i, miR-10b, and miR-885-5p. Pathologic expression patterns of three validated CRC metastasis-specific miRNAs (let-7i, miR-10b, and miR-885-5p) were determined by hybridization with LNA-modified and 5'- and 3'-DIG-labeled oligonucleotide probes. In situ hybridization analysis of let-7i, miR-10b, and miR-885-5p in (A) positive and negative controls (pCRC), and (B) matched primary pCRC with and without later metastases, and expression in the matched LM. (Positive control, U6 snRNA; Negative control, scrambled miRNA control)

FIGS. 9A-9B)—Kaplan-Meier Overall Survival Analysis based on 4 miRNAs (let-7i, miR-10b, miR-221, and miR-320a) in miRNA Microarray Cohort. Based on Kaplan-Meier survival curves, 4 miRNAs were categorized into (A) Tumor Suppressor-miRNA group (let-7i and miR-320a) and (B) Oncogenic-miRNA group (miR-10b and miR-221). The P values were determined by log-rank test.

FIGS. 10A-10B)—Kaplan-Meier Overall Survival Analysis based on 2 miRNAs (let-7 and miR-10b) in the miRNA Microarray Validation Cohort. The P values were determined by log-rank test.

FIGS. 11A-11B)—Kaplan-Meier Overall Survival Analysis based on Tissue and Serum-miR-885-5p Expression in Matching CRC Tissue and Serum Cohort. The P values were determined by log-rank test.

FIGS. 14A-14E—The miR-21 expression levels in serum samples (n=282). (A) Box plots represent serum miR-21 levels in healthy controls (N; n=53) and patients with adenomatous polyps (Ad; n=43) and different TNM stages (I, II, III and IV) of CRC (n=186). Y-axis (log 10-scale) represents relative expression of miR-21 normalized to cel-miR-39. Boxes represent the interquartile range and the horizontal line across each box indicates median values. Statistically significant differences were determined using the Mann-Whitney U test and Kruskal-Wallis tests. *P<0.05; ***P<0.0001. Receiver operating characteristics (ROC) curve analysis using serum miR-21 for distinguishing patients with colorectal neoplasms from normal controls. (B) Serum miR-21 yielded an AUC value of 0.927 (95% CI: 0.89-0.96), with 82.8% sensitivity and 90.6% specificity in distinguishing CRC from normal controls. (C) Serum miR-21 yielded AUC values of 0.803 (95% CI: 0.71-0.88) with 76.8% sensitivity and 81.1% specificity in discriminating adenomas from normal controls. ROC convex hull (ROCCH) curve analysis using raw data and BCa bootstrap bias-corrected data for distinguishing patients with colorectal neoplasms from normal controls. (D) AUC values derived from ROCCH curves of original and BCa bootstrap-corrected samples were 0.935 (95% CI: 0.812-0.982) and 0.919 (95% CI: 0.867-0.958), respectively in distinguishing CRC patients from normal controls. (E) AUC values derived from ROCCH curves of original and BCa bootstrap-corrected samples were 0.838 (95% CI: 0.619-0.964) and 0.813 (95% CI: 0.691-0.910), respectively in distinguishing adenoma patients from normal controls.

FIGS. 29A-29C—Strategy for identification of potential targets of miR-124 in CRC. (A) The Venn diagram represents the down-regulated genes (>1.5 fold change) observed in the gene microarray analysis after transfection of miR- 124 precursor (in blue), and the predicted targets with seeding sequences of miR-124 was selected by in silico prediction tool miRecords (in red). (B) The list of genes identified using mentioned strategy. The expression intensity of each mRNA. (C) Comparison between microarray analysis and RT-PCR. For each MAPRE1 and PPM1F gene, the variation in expression compared to control is represented as average fold change for microarray and comparison of expression levels between miR-124 precursor transfected cells and control cells.

DETAILED DESCRIPTION OF THE INVENTION

Figure 1:
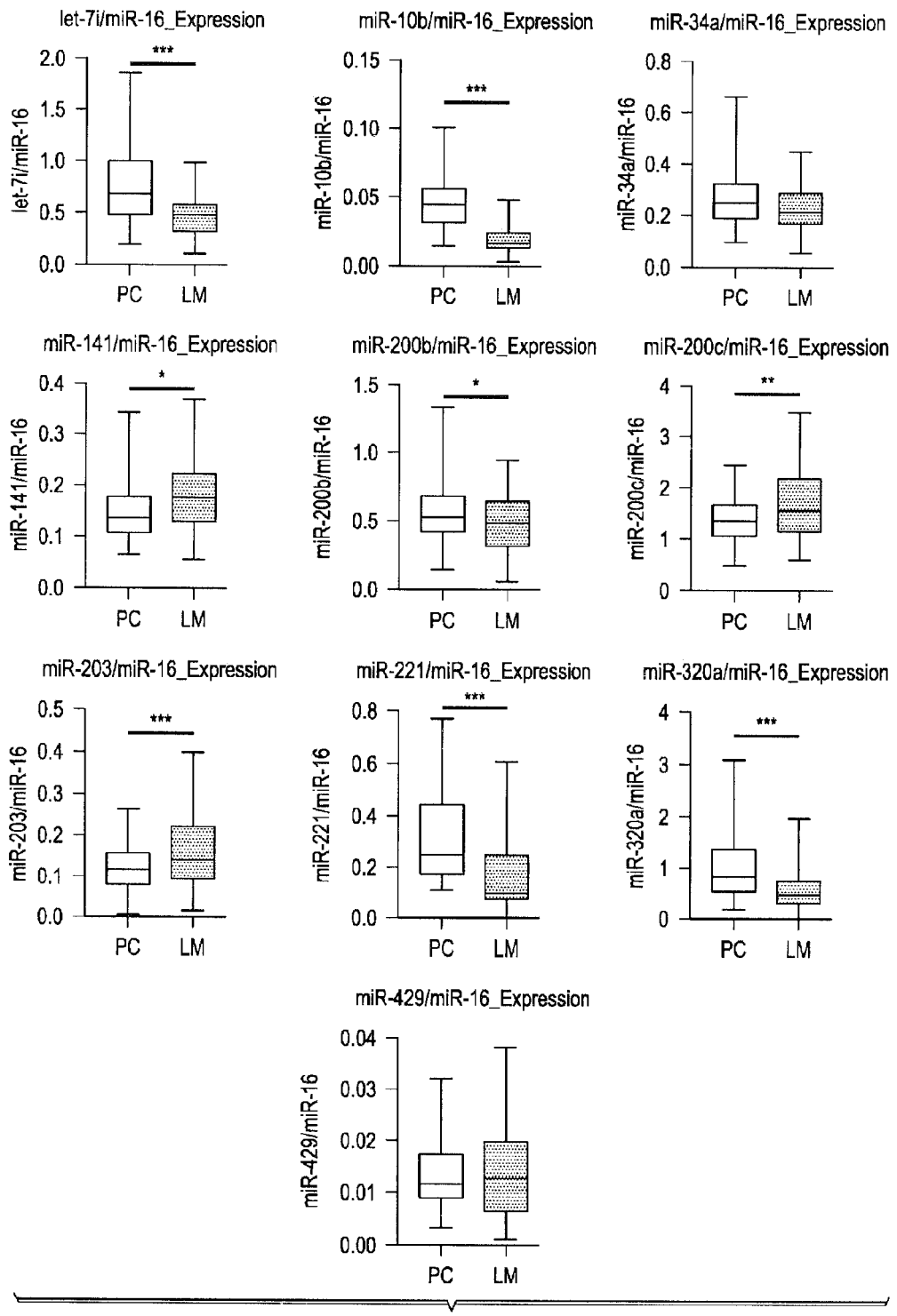
FIG. 1—FIG. 1 shows the expression analysis of metastasis predictive microRNAs expression comparing Primary Colorectal (PC) cancer microRNA expression compared to colorectal cancer (CRC) liver metastasis (LM) microRNA expression.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

Embodiments of the present invention involve biomarkers and methods for detecting Colorectal Cancer (CRC) metastasis and exploring curative target of metastasized CRC, including but not limited to cancer research, cancer screening, diagnosis of metastasis, planning of cancer treatment and molecular target of anti-cancer drug.

Certain aspects of the present invention include the identification and use of miRNA biomarkers (let-7i, miR-10b, miR-30b, miR-21, miR-31, miR-34a, miR-141, miR-200b, miR-200c, miR-203, miR-221, miR-320a, miR-373, miR-429, miR-518d, and miR-520c) that have been found to be very specific for detecting liver metastasized CRC. Most of the existing cancer metastasis biomarkers are developed through comparison between primary tissues with metastasis and without metastasis. In contrast, certain aspects of the present invention may be based on a detailed analysis and discovery that certain miRNA biomarkers were identified by direct comparison between primary CRC and matching liver metastasis tissues, rather than a comparison to primary tissues. These biomarkers were validated using tissue sample miRNAs expression, but also using serum samples of CRC patients with distant metastasis. Thus, the miRNA biomarkers in certain aspects of the present invention are more accurate and specific compared to biomarkers developed using just primary cancer tissues.

Certain aspects of the present invention have several advantages when compared to existing miRNA biomarkers. First, the miRNAs biomarkers may be used as metastasis specific biomarkers because they are derived from the direct comparison between primary CRC and matching liver metastasis tissues. Second, the miRNAs biomarkers are more specific for the detection of CRC metastasis, as validated using miRNAs expression of serum samples from CRC patients with and without distant metastasis.

I. DEFINITIONS

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

"Diagnosis" may refer to the process of attempting to determine or identify a possible disease or disorder, or to the opinion reached by this process. From the point of view of statistics the diagnostic procedure may involve classification tests.

"Prognosis" may refer to a prediction of how a patient will progress, and whether there is a chance of recovery. "Cancer prognosis" generally refers to a forecast or prediction of the probable course or outcome of the cancer. As used herein, cancer prognosis includes the forecast or prediction of any one or more of the following: duration of survival of a patient susceptible to or diagnosed with a cancer, duration of recurrence-free survival, duration of progression free survival of a patient susceptible to or diagnosed with a cancer, response rate in a group of patients susceptible to or diagnosed with a cancer, duration of response in a patient or a group of patients susceptible to or diagnosed with a cancer, and/or likelihood of metastasis in a patient susceptible to or diagnosed with a cancer. Prognosis may also include prediction of favorable responses to cancer treatments, such as a conventional cancer therapy.

By "subject" or "patient" is meant any single subject for which therapy is desired, including humans, cattle, dogs, guinea pigs, rabbits, chickens, and so on. Also intended to be included as a subject are any subjects involved in clinical research trials not showing any clinical sign of disease, or subjects involved in epidemiological studies, or subjects used as controls.

As used herein, the term "colorectal cancer" includes the well-accepted medical definition that defines colorectal cancer as a medical condition characterized by cancer of cells of the intestinal tract below the small intestine (i.e., any portion of the large intestine (colon), including the cecum, ascending colon, transverse colon, descending colon, sigmoid colon, or rectum). Additionally, as used herein, the term "colorectal cancer" also further includes medical conditions, which are characterized by cancer of cells of the duodenum and small intestine (jejunum and ileum).

As used herein, the term "tissue sample" (the term "tissue" is used interchangeably with the term "tissue sample") includes any material composed of one or more cells, either individual or in complex with any matrix obtained from a patient. The definition includes any biological or organic material and any cellular subportion, product or by-product thereof. The definition of "tissue sample" should be understood to include without limitation colorectal tissue samples, tissues suspected of including colorectal cancer cells, blood components, and even fecal matter or fluids that includes colorectal cells. Also included within the definition of "tissue" for purposes of this invention are certain defined acellular structures such as dermal layers of epithelium that have a cellular origin but are no longer characterized as cellular. The term "stool" or "feces" as used herein is a clinical term that refers to feces obtained from a mammal such as a human.

As used herein, the term "biological fluid" refers to a fluid containing cells and compounds of biological origin, and may include blood, stool or feces, lymph, urine, serum, pus, saliva, seminal fluid, tears, urine, bladder washings, colon washings, sputum or fluids from the respiratory, alimentary, circulatory, or other body systems. For the purposes of the present invention the "biological fluids", the nucleic acids containing the biomarkers may be present in a circulating cell or may be present in cell-free circulating DNA or RNA.

As used herein, the term "gene" refers to a functional protein, polypeptide or peptide-encoding unit. As will be understood by those in the art, this functional term includes both genomic sequences, cDNA sequences, or fragments or combinations thereof, as well as gene products, including those that may have been altered by the hand of man. Purified genes, nucleic acids, protein and the like are used to refer to these entities when identified and separated from at least one contaminating nucleic acid or protein with which it is ordinarily associated. The term "allele" or "allelic form" refers to an alternative version of a gene encoding the same functional protein but containing differences in nucleotide sequence relative to another version of the same gene.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

As used herein, a "biomarker" refers to a molecular indicator that is associated with a particular pathological or physiological state. The "biomarker" as used herein is a molecular indicator for cancer, more specifically an indicator for primary CRCs and distant metastasis of primary CRCs. Examples of "biomarkers" include miR-885-5p, let-7i, miR-10b, miR-21, miR-31, miR-30b, miR-34a, miR-124, miR-141, miR-200b, miR-200c, miR-203, miR-221, miR-320a, miR-373, miR-429, miR-518d, and miR-520c.

The term "biomarker miRNA" refers to a miRNA whose expression level is indicative of a particular disease or condition. The level of expression of a biomarker miRNA may highlight or emphasize differences in miRNA expression between different populations, such as low or high risk cancer, particularly colorectal cancer. In some embodiments, when miRNA expression is different in a particular population relative to another population, differences between miRNA expression levels can be increased, decreased, highlighted, emphasized, or otherwise more readily observed.

As used herein, the term "kit" or "testing kit" denotes combinations of reagents and adjuvants required for an analysis. Although a test kit consists in most cases of several units, one-piece analysis elements are also available, which must likewise be regarded as testing kits.

As used herein, the term "TNM" refers to the internationally recognized TNM classification of malignant tumors developed and maintained by the International Union Against Cancer, which has been adopted by the American Joint Committee on Cancer (AJCC) and the International Federation of Gynecology and Obstetrics (FIGO). T refers to the size or direct extent of the primary tumor; N to the degree of spread to regional lymph nodes, and M to the presence of metastasis.

II. BIOMARKERS

Biomarker microRNAs (miRNAs) are short RNA molecules (e.g., 16-29 nucleotides in length) that arise from longer precursors, which are transcribed from non-protein coding genes (Carrington et al., 2003). The precursors are processed by cellular proteins to generate short double-stranded miRNA. One of the miRNA strands is incorporated into a complex of proteins and miRNA called the RNA-induced silencing complex (RISC). The miRNA guides the RISC complex to a target mRNA, which is then cleaved or translationally silenced, depending on the degree of sequence complementarity of the miRNA or its target mRNA (Bagga et al., 2005; Lim et al., 2005).

Previous work has shown that several miRNAs are differentially expressed in cancers, including CRC (Calin 2006; Schetter 2008; Lu 2005; Balaguer 2010; Balaguer 2011; Link 2010). MiRNA signatures are emerging as promising biomarkers for diagnosis, prognosis and metastasis for cancer patients (Schetter 2008; Bloomston 2007). Most studies to date have focused on the role for miRNAs in primary tumors but not the metastatic foci. A more systematic and comprehensive analysis is necessary to determine the specific involvement of miRNAs in CRC metastasis. Also, miRNAs are relatively stable and measurable, making them ideal targets for molecular diagnostics.

A. miR-885-5p, let-7i, and miR-10b

The miR-885-5p form of this microRNA acts as a tumour suppressor in neuroblastoma, through interference with cell cycle progression and cell survival. It is found at 3p25.3, a chromosome region frequently deleted in primary neuroblastoma, and expression results in p53 protein accumulation and pathway activation. Altered expression of multiple genes is observed with miR-885-5p, including the CDK2 and MCM5 genes encoding cyclin-dependent kinase 2 and mini-chromosome maintenance protein MCM5, and also with several p53 target genes.

In certain embodiments, serum miR-885-5p may be used as a non-invasive CRC biomarker. MiR-885-5p was significantly up-regulated in LM compared to pCRC tissues, and high serum miR-885-5p expression was an independent factor for predicting CRC prognosis and metastasis, suggesting that the elevated levels of serum miR-885-5p may be due to up-regulation of this miRNA in distant, metastasized cells.

With the potential clinical impact of being metastasis-specific miRNAs, both let7i and miR-10b were significantly down-regulated in LM compared to pCRC. Low let-7i expression and high miR-10b expression were independent predictors of distant metastasis in pCRC tissues. Since each miRNA can regulate hundreds of different target genes,[6,7] aberrantly expressed miRNAs in cancer tissues reflect the possible mechanistic basis of genetic dysregulation in multiple signaling pathways.

These miRNAs may be used as both tissue and/or serum-based CRC metastasis biomarkers may be clinically applicable for the management of patients with CRC.

B. miR-200

Epithelial-to-mesenchymal transition (EMT) manifests through downregulation of E-cadherin and successive loss of cell-cell adhesion, leading to a mesenchymal phenotype (Thiery 2009). This contributes to accelerated invasiveness, dissemination and metastasis of epithelial tumor cells in several carcinomas, including CRC (Spaderna 2006; Hugo 2007; Thiery 2002). The miR-200 family (miR-200a, miR-200b, miR-200c, miR-141, and miR-429) inhibits the E-cadherin-suppressor targets such as zinc finger E-box binding homeobox-1 (ZEB1) and 02 (ZEB2), which are important initiators of EMT in CRC (Burk 2008; Wellner 2009). In addition, dysregulated expression of miR-200b, -200c, -141 and -429 is responsible for EMT-MET switch in colorectal metastasis. MiR-200c/429 cluster was found to be significantly over-expressed in liver metastasis compared to primary colorectal cancer, and the expression of these miRNAs was specifically regulated by aberrant expression of their promoter regions (Hur 2012). In spite of their involvement in metastasis, none of the previous studies has explored the clinical significance of miR-200 family expression in serum of patients with CRC.

In certain embodiments of the invention, serum levels of miR-200c, which is a bona fide EMT-related miRNA, are not only significantly associated with a metastatic phenotype in the colon, but also serve as a potential biomarker for predicting lymph node metastasis, tumor recurrence and prognosis in CRC patients.

C. miR-21

MiR-21 is an "oncogenic miRNA" that modulates the expression of multiple cancer-related target genes such as PTEN, TPM1 and PDCD, has been shown to be overexpressed in various human tumors (Meng 2007; Zhu 2007; Asangani 2008). In addition, miR-21 expression is up-regulated in CRC tissues, is elevated during tumor progression, and is also associated with poor survival and response to chemotherapy (Slaby 2007; Shibuya 2010; Chang 2011; Schetter 2008). The clinical significance of circulating miR-21 levels in CRC remains unclear at this time. While an earlier study was unable to use plasma miR-21 as a biomarker due to low levels of detection using direct amplification method (Pu 2010), a more recent study demonstrated significantly elevated plasma miR-21 expression in CRC patients using TaqMan-based approaches (Kanaan 2012). On the other hand, miR-31 is another miRNA frequently overexpressed in CRC tissues and has been shown to associate with tumor prognosis (Slaby 2007; Wang 2009). Additionally, both miR-21 and miR-31 are significantly upregulated even in premalignant lesions, such as colonic adenomas, which are the target lesions of CRC screening (Oberg 2011; Fassan 2011; Cekaite 2012). It is envisaged that these two miRNAs might be good candidates for exploration as circulating biomarkers for the early detection and prognosis of CRC, assuming that the expression pattern for these miRNAs in serum mirrors that in the neoplastic tissues.

Certain aspects of the invention are based, in part, on two important observations. First, miR-21 levels in cell culture medium increased significantly in a time- and cell number-dependent manner, establishing the secretory nature of this miRNA for development as a noninvasive biomarker of the early detection of colorectal neoplasia. Second, a significant correlation in miR-21 expression was observed between matching serum and tissues from a small subset of CRC patients, validating the specificity of miR-21 expression in the circulation. Increased miR-21 expression was thereafter successfully validated in a large, independent set of matching serum and tissue samples. These results are the first to demonstrate that high levels of miR-21 in both primary CRC tissues and matched serum samples are associated with large tumor size, distant metastasis and advanced TNM stage. Another interesting feature was the existence of significant correlation between miR-21 expression in primary lesions and those in sera. The fact that the circulating miR-21 in serum of CRC patients is likely produced by the CRCs was further strengthened by an observation that a significant drop in serum miR-21 expression in post-operative serum vis-à-vis pre-operative samples following potentially curative surgery in patients with CRC.

In certain aspects of the invention, miR-21 expression may be exploited not only as a promising non-invasive biomarker for early detection of CRC, but also for the identification of clinically meaningful adenomas—a critical target lesion for any CRC screening strategy.

miR-21 expression in serum may also serve as a prognostic biomarker for CRC. High levels of serum miR-21 indicate a poor prognosis in patients with CRC, providing a significant step forward in the identification of a non-invasive biomarker for this disease. Furthermore, the multivariate Cox's proportional hazards model illustrated that high expression of serum miR-21 was an independent prognostic variable, whereas the prognostic values of miR-21 expression in tumors and CEA levels were significantly compromised by other clinical factors. Therefore, serum levels of miR-21 might not only diagnose neoplasia, but also help predict metastases or tumor recurrence with higher accuracy compared to miR-21 expression in the tumor tissue.

Examples described herein clearly highlight that the relative expression for serum miR-21 was significantly different between cases (patients with adenomas and cancers) and controls. Unlike tissue or cellular miRNAs, at present, due to the lack of availability of a consensus house-keeping miRNA for normalizing the expression of circulating miRNAs (Cortez 2011; Zen 2012), measurement of "relative expression levels" of circulating miRNAs has been the common approach in published studies. In spite of this limitation, same amount of the starting serum (200 ul) from each patient was used for every quantitation and, in order to further ensure the technical aspects of the assay, including variability in serum RNA extraction and PCR amplification efficiencies, the normalization of experimental miRNA data was done by using spiked-in synthetic, nonhuman mature miRNA from C. elegans (Kroh 2010). Although the method of quantifying relative expression [$2^{-\Delta Ct}$; $\Delta Ct = Ct$ (miRNA of interest)–Ct (cel-miR-39)] of serum miRNAs was quite robust, absolute quantitation of serum miR-21 expression levels may further improve the translation of these data into a clinically-viable diagnostic test for the early detection of colorectal neoplasia in the immediate future.

Thus, certain aspects of the invention provide compelling evidence for the potential usefulness of serum miR-21 as a noninvasive screening and prognostic tool in patients with colorectal neoplasia, a concept that can be incorporated into routine clinical practice.

III. SAMPLES

The expression of one or more biomarkers may be measured in a sample of cells or non-cell samples from a subject with cancer or suspected of having cancer. The type and classification of the cancer can and will vary. The cancer may be an early stage cancer, i.e., stage I or stage II, or it may be a late stage cancer, i.e., stage III or stage IV. The cancer may be a cancer of the colon or rectum.

Other types of cancer include, but are not limited to, anal cancer, bladder cancer, bone cancer, brain cancer, breast cancer, cervical cancer, duodenal cancer, endometrial cancer, eye cancer, gallbladder cancer, head and neck cancer, liver cancer, larynx cancer, non-small cell lung cancer, small cell lung cancer, lymphomas, melanoma, mouth cancer, ovarian cancer, pancreatic cancer, penal cancer, prostate cancer, rectal cancer, renal cancer, skin cancer, testicular cancer, thyroid cancer, and vaginal cancer.

A. Biological Samples

In order to carry out the method of the invention, a sample is obtained from the subject under study. For example, the sample of cells or tissue sample will be obtained from the subject with cancer by biopsy or surgical resection. The type of biopsy can and will vary, depending upon the location and nature of the cancer. In a particular embodiment, said sample is a tumor tissue sample or opinion thereof. In a more particular embodiment, said tumor tissue sample is a colorectal tissue sample from a patient suffering from colorectal cancer. Said sample can be obtained by conventional methods, e.g., biopsy, by using methods well known to those of ordinary skill in the related medical arts. Methods for obtaining the sample from the biopsy include gross apportioning of a mass, or microdissection or other art-known cell-separation methods. Tumor cells can additionally be obtained from fine needle aspiration cytology. Still further, samples can be obtained from the subject without the assistance of a medical professional; such as the samples can be obtained in the privacy of the subject's home. Such samples that can be procured without the assistance of a medical professional includes, but is not limited to fecal samples, urine samples, blood samples (e.g., whole blood samples), buccal samples, and salvia samples.

Samples can be obtained from subjects previously diagnosed or not with colorectal cancer, or from subjects who are receiving or have previously received anti-colorectal cancer treatment. In a particular embodiment, samples can be obtained from patients who have not previously received any anti-colorectal cancer treatment.

In order to simplify conservation and handling of the samples, these can be formalin-fixed and paraffin-embedded or first frozen and then embedded in a cryosolidifiable medium, such as OCT-Compound, through immersion in a highly cryogenic medium that allows for rapid freeze.

In a particular embodiment, the expression levels may be determined using nucleic acids obtained from as fresh tissue from a biopsy or fine needle aspiration cytology. Other tissue samples are envisaged, such a formalin-fixed, paraffin-embedded tissue sample depending on their availability.

Fixed and paraffin-embedded tissue samples are broadly used storable or archival tissue samples in the field of oncology. Nucleic acid may be isolated from an archival pathological sample or biopsy sample which is first deparaffinized. An exemplary deparaffinization method involves washing the paraffinized sample with an organic solvent, such as xylene, for example. Deparaffinized samples can be rehydrated with an aqueous solution of a lower alcohol. Suitable lower alcohols, for example include, methanol, ethanol, propanols, and butanols. Deparaffinized samples may be rehydrated with successive washes with lower alcoholic solutions of decreasing concentration, for example. Alternatively, the sample is simultaneously deparaffinized and rehydrated. The sample is then lysed and nucleic acid is extracted from the sample. As an illustrative, non-limiting example, tissue selected for fixation and paraffin embedding can be fixed in 10% buffered formalin for 16 hours to 48 hours. After this period of time, said tissue will be embedded in paraffin following conventional techniques. Nevertheless, nucleic acid quality issues are especially delicate when analyzing formalin-fixed tissue samples.

In a particular embodiment, the expression levels may be determined using nucleic acids obtained from a fecal sample, urine sample, blood sample, serum sample, biopsy tissue sample or fine needle aspiration cytology. Because of the variability of the cell types in diseased-tissue biopsy material, and the variability in sensitivity of the diagnostic methods used, the sample size required for analysis may range from 1, 10, 50, 100, 200, 300, 500, 1,000, 5,000, 10,000, to 50,000 or more cells. The appropriate sample size may be determined based on the cellular composition and condition of the sample (e.g., fecal, blood, urine, serum and/or salvia), biopsy or cytology, and the standard preparative steps for this determination and subsequent isolation of the nucleic acid for use in the invention are well known to one of ordinary skill in the mi.

A sample of cells, tissue, or fluid may be removed by needle aspiration biopsy. For this, a fine needle attached to a syringe may be inserted through the skin and into the organ or tissue of interest. The needle may be guided to the region of interest using ultrasound or computed tomography (CT) imaging. Once the needle is inserted into the tissue, a vacuum is created with the syringe such that cells or fluid may be sucked through the needle and collected in the syringe. A sample of cells or tissue may also be removed by incisional or core biopsy. For this, a cone, a cylinder, or a tiny bit of tissue is removed from the region of interest. CT imaging, ultrasound, or an endoscope is generally used to guide this type of biopsy. Lastly, the entire cancerous lesion may be removed by excisional biopsy or surgical resection.

Once a sample of cells or sample of tissue is removed from the subject with cancer, it may be processed for the isolation of nucleic acids using techniques well known in the art and disclosed in standard molecular biology reference books, such as Ausubel et al., (2003) Current Protocols in Molecular Biology, John Wiley & Sons, New York, N.Y. A sample of tissue may also be stored in RNAlater (Ambion; Austin Tex.) or flash frozen and stored at −80° C. for later use. The biopsied tissue sample may also be fixed with a fixative, such as formaldehyde, paraformaldehyde, or acetic acid/ethanol. The fixed tissue sample may be embedded in wax (paraffin) or a plastic resin. The embedded tissue sample (or frozen tissue sample) may be cut into thin sections. Nucleic acids may also be extracted from a fixed or wax-embedded tissue sample.

B. Sample Preparation

It is contemplated that the miRNA of a wide variety of samples can be analyzed using arrays, miRNA probes, or array technology. While endogenous miRNA is contemplated for use with compositions and methods disclosed herein, recombinant miRNA—including nucleic acids that are complementary or identical to endogenous miRNA or precursor miRNA—can also be handled and analyzed as described herein. Samples may be biological samples, in which case, they can be from biopsy, fine needle aspirates, exfoliates, fecal, urine, blood, tissue, organs, semen, saliva, tears, other bodily fluid, hair follicles, skin, or any sample containing or constituting biological cells. In certain embodiments, samples may be, but are not limited to, fresh, frozen, fixed, formalin fixed, paraffin embedded, or formalin fixed and paraffin embedded. Alternatively, the sample may not be a biological sample, but a chemical mixture, such as a cell-free reaction mixture (which may contain one or more biological enzymes).

1. Subjects

The subject with cancer will generally be a mammalian subject. Mammals may include primates, livestock animals, and companion animals. Primates may include humans, New World monkeys, Old World monkeys, gibbons, and great apes. Livestock animals may include horses, cows, goats, sheep, deer (including reindeer) and pigs. Companion animals may include dogs, cats, rabbits, and rodents (including mice, rats, and guinea pigs). In an exemplary embodiment, the subject is a human.

In some cases, samples may be obtained from a subject based on the results of such a cytological analysis. A cancer diagnosis may include an examination of a subject by a physician, nurse or other medical professional. The examination may be part of a routine examination, or the examination may be due to a specific complaint. A specific complaint may include but is not limited to: pain, illness, anticipation of illness, presence of a suspicious lump or mass, a disease, or a condition. In particular aspects, the subjects may be suspected of having or be previously determined to have a cancer, a tumor, a pre-cancer, or any other disease.

In some embodiments the subject may or may not be aware of the disease or condition. In some cases, the subject may be referred to a specialist such as an oncologist, surgeon, or endocrinologist. The specialist may likewise obtain a biological sample for testing or refer the individual to a testing center or laboratory for submission of the biological sample. In some cases the medical professional may refer the subject to a testing center or laboratory for submission of the biological sample. In other cases, the subject may provide the sample. In some cases, a molecular profiling business may obtain the sample.

2. Biological Sample Collection

In certain aspects, methods involve obtaining a sample from a subject. The term subject may refer to an animal (for example a mammal), including but not limited to humans, non-human primates, rodents, dogs, or pigs. The methods of obtaining provided herein include methods of biopsy such as fine needle aspiration, core needle biopsy, vacuum assisted biopsy, incisional biopsy, excisional biopsy, punch biopsy, shave biopsy or skin biopsy. In certain embodiments the sample is obtained from a biopsy from colorectal tissue by any of the biopsy methods previously mentioned. In other embodiments the sample may be obtained from any of the tissues provided herein that include but are not limited to gall bladder, skin, heart, lung, breast, pancreas, liver, muscle, kidney, smooth muscle, bladder, colon, intestine, brain, prostate, esophagus, or thyroid tissue. Alternatively, the sample may be obtained from any other source including but not limited to blood, sweat, hair follicle, buccal tissue, tears, menses, feces, or saliva. In certain aspects the sample is obtained from cystic fluid or fluid derived from a tumor or neoplasm. In yet other embodiments the cyst, tumor or neoplasm is colorectal. In certain aspects of the current methods, any medical professional such as a doctor, nurse or medical technician may obtain a biological sample for testing. Yet further, the biological sample can be obtained without the assistance of a medical professional.

A sample may include but is not limited to, tissue, cells, or biological material from cells or derived from cells of a subject. The biological sample may be a heterogeneous or homogeneous population of cells or tissues. The biological sample may be obtained using any method known to the art that can provide a sample suitable for the analytical methods described herein. The sample may be obtained by non-invasive methods including but not limited to: scraping of the skin or cervix, swabbing of the cheek, saliva collection, urine collection, feces collection, collection of menses, tears, or semen.

The sample may be obtained by methods known in the art. In certain embodiments the samples are obtained by biopsy. In other embodiments the sample is obtained by swabbing, scraping, phlebotomy, or any other methods known in the art. In some cases, the sample may be obtained, stored, or transported using components of a kit of the present methods. In some cases, multiple samples, such as multiple colorectal samples may be obtained for diagnosis by the methods described herein. In other cases, multiple samples, such as one or more samples from one tissue type (for example colon) and one or more samples from another tissue (for example buccal) may be obtained for diagnosis by the methods. In some cases, multiple samples such as one or more samples from one tissue type (e.g. rectal) and one or more samples from another tissue (e.g. cecum) may be obtained at the same or different times. Samples may be obtained at different times are stored and/or analyzed by different methods. For example, a sample may be obtained and analyzed by routine staining methods or any other cytological analysis methods.

In some embodiments the biological sample may be obtained by a physician, nurse, or other medical professional such as a medical technician, endocrinologist, cytologist, phlebotomist, radiologist, or a pulmonologist. The medical professional may indicate the appropriate test or assay to perform on the sample. In certain aspects a molecular profiling business may consult on which assays or tests are most appropriately indicated. In further aspects of the current methods, the patient or subject may obtain a biological sample for testing without the assistance of a medical professional, such as obtaining a whole blood sample, a urine sample, a fecal sample, a buccal sample, or a saliva sample.

In other cases, the sample is obtained by an invasive procedure including but not limited to: biopsy, needle aspiration, or phlebotomy. The method of needle aspiration may further include fine needle aspiration, core needle biopsy, vacuum assisted biopsy, or large core biopsy. In some embodiments, multiple samples may be obtained by the methods herein to ensure a sufficient amount of biological material.

General methods for obtaining biological samples are also known in the art. Publications such as Ramzy, Ibrahim Clinical Cytopathology and Aspiration Biopsy 2001, which is herein incorporated by reference in its entirety, describes general methods for biopsy and cytological methods. In one embodiment, the sample is a fine needle aspirate of a colorectal or a suspected colorectal tumor or neoplasm. In some cases, the fine needle aspirate sampling procedure may be guided by the use of an ultrasound, X-ray, or other imaging device.

In some embodiments of the present methods, the molecular profiling business may obtain the biological sample from a subject directly, from a medical professional, from a third party, or from a kit provided by a molecular profiling business or a third party. In some cases, the biological sample may be obtained by the molecular profiling business after the subject, a medical professional, or a third party acquires and sends the biological sample to the molecular profiling business. In some cases, the molecular profiling business may provide suitable containers, and excipients for storage and transport of the biological sample to the molecular profiling business.

In some embodiments of the methods described herein, a medical professional need not be involved in the initial diagnosis or sample acquisition. An individual may alternatively obtain a sample through the use of an over the counter (OTC) kit. An OTC kit may contain a means for obtaining said sample as described herein, a means for storing said sample for inspection, and instructions for proper use of the kit. In some cases, molecular profiling services are included in the price for purchase of the kit. In other cases, the molecular profiling services are billed separately. A sample suitable for use by the molecular profiling business may be any material containing tissues, cells, nucleic acids, genes, gene fragments, expression products, gene expression products, or gene expression product fragments of an individual to be tested. Methods for determining sample suitability and/or adequacy are provided.

3. Biological Sample Storage

In certain aspects, a sample may be obtained and prior to analysis by one or more methods described herein, the sample may be stored for a length of time. A length of time may include a time interval such as seconds, minutes, hours, days, weeks, months, years or longer. In some cases, the sample obtained from a subject is subdivided prior to the step of storage or further analysis. In some cases where the sample is subdivided different portions of the sample are subjected to different downstream methods or processes. Such methods or processes may include storage, cytological analysis, integrity tests, nucleic acid extraction, molecular profiling or any combination of these.

In some cases where storage is contemplated, some part of the sample may be stored while another portion of the sample is further processed. Processing may include but is not limited to molecular profiling, cytological staining, gene or gene expression product (RNA or protein) extraction, detection, or quantification, fixation or examination.

In other cases, the sample is obtained and stored and subdivided after the step of storage for further analysis such that different portions of the sample are subject to different downstream methods or processes including but not limited to storage, cytological analysis, adequacy tests, nucleic acid extraction, molecular profiling or a combination thereof.

In some cases, samples are obtained and analyzed by cytological analysis, and the resulting sample material is further analyzed by one or more molecular profiling methods described herein. In such cases, the samples may be stored between the steps of cytological analysis and the steps of molecular profiling. Samples may be stored upon acquisition to facilitate transport, or to wait for the results of other analyses. In another embodiments, samples may be stored while awaiting instructions a medical professional.

An acquired sample may be placed in short term or long term storage by placing in a suitable medium, excipient, solution, or container. In certain cases storage may require keeping the sample in a refrigerated, or frozen environment. The sample may be quickly frozen prior to storage in a frozen environment. In certain instances the frozen sample may be contacted with a suitable cryopreservation medium or compound. Examples of cryopreservation mediums or compounds include but are not limited to: glycerol, ethylene glycol, sucrose, or glucose.

A suitable medium, excipient, or solution may include but is not limited to: hanks salt solution, saline, cellular growth medium, an ammonium salt solution such as ammonium sulphate or ammonium phosphate, or water.

Suitable concentrations of ammonium salts include solutions of about 0.1 g/ml, 0.2 g/ml, 0.3 g/ml, 0.4 g/ml, 0.5 g/ml, 0.6 g/ml, 0.7 g/ml, 0.8 g/ml, 0.9 g/ml, 1.0 g/ml, 1.1 g/ml, 1.2 g/ml, 1.3 g/ml, 1.4 g/ml, 1.5 g/ml, 1.6 g/ml, 1.7 g/ml, 1.8 g/ml, 1.9 g/ml, 2.0 g/ml, 2.2 g/ml, 2.3 g/ml, 2.5 g/ml, 2.7 g/ml, 3.0 g/ml or higher. The medium, excipient, or solution may or may not be sterile.

The medium, excipient, or solution may contain preservative agents to maintain the sample in an adequate state for subsequent diagnostics or manipulation, or to prevent coagulation. Said preservatives may include citrate, ethylene diamine tetraacetic acid, sodium azide, or thimersol. The sample may be fixed prior to or during storage by any method known to the art such as using glutaraldehyde, formaldehyde, or methanol. The container may be any container suitable for storage and or transport of the biological sample including but not limited to: a cup, a cup with a lid, a tube, a sterile tube, a vacuum tube, a syringe, a bottle, a microscope slide, or any other suitable container. The container may or may not be sterile. In some cases, the sample may be stored in a commercial preparation suitable for storage of cells for subsequent cytological analysis such as but not limited to Cytyc ThinPrep, SurePath, or Monoprep.

The storage temperature may be explicitly defined or defined by a temperature range. The sample may be stored at room temperature or at reduced temperatures such as cold temperatures (e.g. between about 20° C. and about 0° C.), or freezing temperatures, including for example 0° C., −1° C., −2° C., −3° C., −4° C., −5° C., −6° C., −7° C., −8° C., −9° C., −10° C., −12° C., −14° C., −15° C., −16° C., −20° C., −22° C., −25° C., −28° C., −30° C., −35° C., −40° C., −45° C., −50° C., −60° C., −70° C., −80° C., −100° C., −120° C., −140° C., −180° C., −190° C., −200° C. or any ranges or values derivable therein. The sample may be stored in any condition or environment that allows or achieves the desired temperature condition. In some cases, the samples may be stored in a refrigerator, on ice or a frozen gel pack, in a freezer, in a cryogenic freezer, on dry ice, in liquid nitrogen, or in a vapor phase equilibrated with liquid nitrogen.

The sample container may be any container suitable for storage and or transport of the biological sample including but not limited to: a cup, a cup with a lid, a tube, a sterile tube, a vacuum tube, a syringe, a bottle, a microscope slide, or any other suitable container. The container may or may not be sterile.

4. Sample Conveyance and Transportation

Additionally contemplated in the current methods are methods of transporting a sample. Transport may involve moving or conveyance of a sample to or from a clinic, hospital, doctor's office, or other location to a second location. Upon transport the sample may be stored and/or analyzed by for example, cytological analysis or molecular profiling. In some embodiments some aspect of analysis, processing or profiling may begin or take place during transport. In some cases, the sample may be transported to a molecular profiling company in order to perform the analyses described herein. In other cases, the sample may be transported to a laboratory such as a laboratory authorized or otherwise capable of performing the methods described herein, such as a Clinical Laboratory Improvement Amendments (CLIA) laboratory.

In some instances the subject may transport the sample. Transportation by an individual may include the individual appearing at a molecular profiling business or a designated sample receiving point and providing a sample. Providing of the sample may involve any of the techniques of sample acquisition described herein, or the sample may have already have been acquired and stored in a suitable container. In other cases the sample may be transported to a molecular profiling business using a courier service, the postal service, a shipping service, or any method capable of transporting the sample in a suitable manner.

In some cases, the sample may be provided to a molecular profiling business by a third party testing laboratory (e.g. a cytology lab). In other cases, the sample may be provided to a molecular profiling business by the subject's primary care physician, endocrinologist or other medical professional. The cost of transport may be billed to the individual, medical provider, or insurance provider. The molecular profiling business may begin analysis of the sample immediately upon receipt, or may store the sample in any manner described herein. The method of storage may or may not be the same as chosen prior to receipt of the sample by the molecular profiling business.

The sample may be transported in any medium or excipient including any medium or excipient provided herein suitable for storing the sample such as a cryopreservation medium or a liquid based cytology preparation. In some cases, the sample may be transported frozen or refrigerated such as at any of the suitable sample storage temperatures provided herein.

Once the sample is received, the sample may be assayed using a variety of routine analyses known to the art such as cytological assays, and genomic analysis by a molecular profiling business, a representative or licensee thereof, a medical professional, researcher, or a third party laboratory or testing center (e.g. a cytology laboratory). Such tests may be indicative of cancer, the type of cancer, any other disease or condition, the presence of disease markers, or the absence of cancer, diseases, conditions, or disease markers. The tests may take the form of cytological examination including microscopic examination as described below. The tests may involve the use of one or more cytological stains. The biological material may be manipulated or prepared for the test prior to administration of the test by any suitable method known to the art for biological sample preparation. The specific assay performed may be determined by the molecular profiling company, the physician who ordered the test, or a third party such as a consulting medical professional, cytology laboratory, the subject from whom the sample derives, or an insurance provider. The specific assay may be chosen based on the likelihood of obtaining a definite diagnosis, the cost of the assay, the speed of the assay, or the suitability of the assay to the type of material provided.

5. Sample Integrity Tests

In some embodiments, concurrent with sample acquisition, sample storage or sample analysis the sample may be subjected to tests or examination that detail or reveal the integrity of the sample for use in the compositions or methods described herein. As a result of an integrity test a sample may be determined to be adequate or inadequate for further analysis.

In some embodiments sample integrity tests may pertain to the quality, integrity or adequacy of cells and or tissue in the sample. Metrics employed to determine quality, integrity or adequacy may involve but are not limited to cell number tests, cell viability tests, nuclear content tests, genetic content tests, biochemical assays, cell mass tests, cell volume tests, PCR tests, Q-PCR tests, RT-PCR tests, immunochemical analysis, histochemical analysis, microscopic analysis or visual analysis.

In certain aspects sample integrity may be ascertained by tests that measure nucleic acid content or integrity. Nucleic acid content tests may measure DNA content, RNA content or a some mixture of DNA or RNA. In some aspects nucleic acids are extracted or purified from other cellular components prior to a nucleic acid content test. In some embodiments nucleic acid specific dyes are used to assay nucleic acid integrity. In cases of nucleic acid extraction, spectrophotometric or electrophoretic methods may be used to assay nucleic acid integrity.

In yet other aspects, sample integrity may be ascertained by tests that measure protein content or integrity. Methods that measure protein content or integrity are well known to those skilled in the art. Such methods include but are not limited to ultraviolet absorbance reading (e.g. 280 nm absorbance readings), cell staining, protein staining or immunocytochemical methods. In some instances tests may be performed in parallel in intact samples or the samples may be divided and tests performed serially or in parallel.

Integrity tests may be performed on small subsets or aliquots of a sample or on the entirety of a sample.

IV. NUCLEIC ACID ASSAY METHODS

It is contemplated that a number of assays could be employed to analyze miRNAs in biological samples. Such assays include, but are not limited to, array hybridization, solution hybridization, nucleic amplification, polymerase chain reaction, quantitative PCR, RT-PCR, in situ hybridization, Northern hybridization, hybridization protection assay (HPA) (GenProbe), branched DNA (bDNA) assay (Chiron), rolling circle amplification (RCA), single molecule hybridization detection (US Genomics), Invader assay (ThirdWave Technologies), and/or Oligo Ligation Assay (OLA), hybridization, and array analysis. U.S. patent application Ser. No. 11/141,707, filed May 31, 2005; Ser. No. 11/857,948, filed Sep. 19, 2007; Ser. No. 11/273,640, filed Nov. 14, 2005 and provisional patent application 60/869,295, filed Dec. 8, 2006 are incorporated by reference in their entirety.

A. Isolation of Nucleic Acids

Nucleic acids may be isolated using techniques well known to those of skill in the art, though in particular embodiments, methods for isolating small nucleic acid molecules, and/or isolating RNA molecules can be employed.

Chromatography is a process often used to separate or isolate nucleic acids from protein or from other nucleic acids. Such methods can involve electrophoresis with a gel matrix, filter columns, alcohol precipitation, and/or other chromatography.

If miRNA from cells is to be used or evaluated, methods generally involve lysing the cells with a chaotropic (e.g., guanidinium isothiocyanate) and/or detergent (e.g., N-lauroyl sarcosine) prior to implementing processes for isolating particular populations of RNA.

In particular methods for separating miRNA from other nucleic acids, a gel matrix may be prepared using polyacrylamide, though agarose can also be used. The gels may be graded by concentration or they may be uniform. Plates or tubing can be used to hold the gel matrix for electrophoresis. For example, one-dimensional electrophoresis may be employed for the separation of nucleic acids. Plates may be used to prepare a slab gel, while the tubing (glass or rubber, typically) can be used to prepare a tube gel. The phrase "tube electrophoresis" refers to the use of a tube or tubing, instead of plates, to form the gel. Materials for implementing tube electrophoresis can be readily prepared by a person of skill in the art or purchased.

Methods may involve the use of organic solvents and/or alcohol to isolate nucleic acids, particularly miRNA used in methods and compositions disclosed herein. Some embodiments are described in U.S. patent application Ser. No. 10/667,126, which is hereby incorporated by reference.

In certain aspects, this disclosure provides methods for efficiently isolating small RNA molecules from cells comprising: adding an alcohol solution to a cell lysate and applying the alcohol/lysate mixture to a solid support before eluting the RNA molecules from the solid support. In some embodiments, the amount of alcohol added to a cell lysate achieves an alcohol concentration of about 55% to 60%. While different alcohols can be employed, ethanol works well. A solid support may be any structure, and it includes beads, filters, and columns, which may include a mineral or polymer support with electronegative groups. A glass fiber filter or column may work particularly well for such isolation procedures.

In specific embodiments, miRNA isolation processes may include: a) lysing cells in the sample with a lysing solution comprising guanidinium, wherein a lysate with a concentration of at least about 1 M guanidinium is produced; b) extracting miRNA molecules from the lysate with an extraction solution comprising phenol; c) adding to the lysate an alcohol solution for forming a lysate/alcohol mixture, wherein the concentration of alcohol in the mixture is between about 35% to about 70%; d) applying the lysate/alcohol mixture to a solid support; e) eluting the miRNA molecules from the solid support with an ionic solution; and, f) capturing the miRNA molecules. Typically the sample is dried down and resuspended in a liquid and volume appropriate for subsequent manipulation.

B. Amplification

Many methods exist for evaluating miRNA levels by amplifying all or part of miRNA nucleic acid sequences such as mature miRNAs, precursor miRNAs, and/or primary miRNAs. Suitable nucleic acid polymerization and amplification techniques include reverse transcription (RT), polymerase chain reaction (PCR), real-time PCR (quantitative PCR (q-PCR)), nucleic acid sequence-base amplification (NASBA), ligase chain reaction, multiplex ligatable probe amplification, invader technology (Third Wave), rolling circle amplification, in vitro transcription (IVT), strand displacement amplification, transcription-mediated amplification (TMA), RNA (Eberwine) amplification, and other methods that are known to persons skilled in the art. In certain embodiments, more than one amplification method may be used, such as reverse transcription followed by real time PCR (Chen et al., 2005 and/or U.S. patent application Ser. No. 11/567,082, filed Dec. 5, 2006, which are incorporated herein by reference in its entirety).

An exemplary PCR reaction includes multiple amplification steps, or cycles that selectively amplify target nucleic acid species. An exemplary reaction includes three steps: a denaturing step in which a target nucleic acid is denatured; an annealing step in which a set of PCR primers (forward and reverse primers) anneal to complementary DNA strands; and an elongation step in which a thermostable DNA polymerase elongates the primers. By repeating these steps multiple times, a DNA fragment is amplified to produce an amplicon, corresponding to the target DNA sequence. Exemplary PCR reactions may include 20 or more cycles of denaturation, annealing, and elongation. In many cases, the annealing and elongation steps can be performed concurrently, in which case the cycle contains only two steps. Since mature miRNAs are single stranded, a reverse transcription reaction (which produces a complementary cDNA sequence) is performed prior to PCR reactions. Reverse transcription reactions include the use of, e.g., a RNA-based DNA polymerase (reverse transcriptase) and a primer.

In PCR and q-PCR methods, for example, a set of primers is used for each target sequence. In certain embodiments, the lengths of the primers depends on many factors, including, but not limited to, the desired hybridization temperature between the primers, the target nucleic acid sequence, and the complexity of the different target nucleic acid sequences to be amplified. In certain embodiments, a primer is about 15 to about 35 nucleotides in length. In other embodiments, a primer is equal to or fewer than 15, 20, 25, 30, or 35 nucleotides in length or any range derivable therein. In additional embodiments, a primer is at least 35 nucleotides in length.

In a further aspect, a forward primer can comprise at least one sequence that anneals to a target miRNA and alternatively can comprise an additional 5' noncomplementary region. In another aspect, a reverse primer can be designed to anneal to the complement of a reverse transcribed miRNA. The reverse primer may be independent of the miRNA sequence, and multiple miRNAs may be amplified using the same reverse primer. Alternatively, a reverse primer may be specific for a miRNA.

In some embodiments, two or more miRNAs or nucleic acids are amplified in a single reaction volume or multiple reaction volumes. In certain aspects, one or more miRNA or nucleic may be used as a normalization control or a reference nucleic acid for normalization. Normalization may be performed in separate or the same reaction volumes as other amplification reactions.

One aspect includes multiplex q-PCR, such as qRT-PCR, which enables simultaneous amplification and quantification of at least one miRNA of interest and at least one reference nucleic acid in one reaction volume by using more than one pair of primers and/or more than one probe. The primer pairs may comprise at least one amplification primer that uniquely binds each nucleic acid, and the probes are labeled such that they are distinguishable from one another, thus allowing simultaneous quantification of multiple miRNAs. Multiplex qRT-PCR has research and diagnostic uses, including but not limited to detection of miRNAs for diagnostic, prognostic, and therapeutic applications.

A single combined reaction for q-PCR, may be used to: (1) decrease risk of experimenter error, (2) reduce assay-to-assay variability, (3) decrease risk of target or product contamination, and (4) increase assay speed. The qRT-PCR reaction may further be combined with the reverse transcription reaction by including both a reverse transcriptase and a DNA-based thermostable DNA polymerase. When two polymerases are used, a "hot start" approach may be used to maximize assay performance (U.S. Pat. Nos. 5,411,876 and 5,985,619). For example, the components for a reverse transcriptase reaction and a PCR reaction may be sequestered using one or more thermoactivation methods or chemical alteration to improve polymerization efficiency (U.S. Pat. Nos. 5,550,044, 5,413,924, and 6,403,341).

To assess the expression of miRNAs, real-time RT-PCR detection can be used to screen nucleic acids or RNA isolated from samples of interest and a related reference such as, but not limited to a normal adjacent tissue (NAT) samples.

A panel of amplification targets may be chosen for real-time RT-PCR quantification. In one aspect, the panel of targets includes one or more miRNA described herein. The selection of the panel or targets can be based on the results of microarray expression analyses, such as with mirVana™ miRNA Bioarray V1 (Ambion), Human miRNA Microarrays (V3) (Agilent), miRLink™ Arrays (Asuragen), or any other suitable microarray.

One example of a normalization target is 5S rRNA and others can be included. Reverse transcription (RT) reaction components may be assembled on ice prior to the addition of RNA template. Total RNA template may be added and mixed. RT reactions may be incubated in an appropriate PCR System at an appropriate temperature (such as 15-30° C., including all values and ranges there between) for an appropriate time, 15 to 30 minutes or longer, then at a temperature of 35 to 42 to 50° C. for 10 to 30 to 60 minutes, and then at 80 to 85 to 95° C. for 5 minutes, then placed on wet ice. Reverse Transcription reaction components may include nuclease-free water, reverse transcription buffer, dNTP mix, RT Primer, RNase Inhibitor, Reverse Transcriptase, and RNA.

Following assembly of the PCR reaction components a portion of the RT reaction is transferred to the PCR mix. PCR reactions may be incubated in an PCR system at an elevated temperature (e.g., 95° C.) for 1 minute or so, then for a number of cycles of denaturing, annealing, and extension (e.g., 40 cycles of 95° C. for 5 seconds and 60° C. for 30 seconds). Results can be analyzed, for example, with SDS V2.3 (Applied Biosystems). Real-time PCR components may include Nuclease-free water, $MgCl_2$, PCR Buffer, dNTP mix, one or more primers, DNA Polymerase, cDNA from RT reaction and one or more detectable label.

Software tools such as NormFinder (Andersen et al., 2004) may be used to determine targets for normalization with the targets of interest and tissue sample set. For normalization of the real-time RT-PCR results, the cycle threshold ($C_t$) value (a log value) for the microRNA of interest is subtracted from the geometric mean $C_t$ value of normalization targets. Fold change can be determined by subtracting the $dC_t$ normal reference (N) from the corresponding $dC_t$ sample being evaluated (T), producing a $ddC_t$ (T−N) value for each sample. The average $ddC_t$(T−N) value across all samples is converted to fold change by $2^{ddCt}$. The representative p-values are determined by a two-tailed paired Student's t-test from the $dC_t$ values of sample and normal reference.

C. Expression Measurement

The expression of one or more biomarkers may be measured by a variety of techniques that are well known in the art. In addition to the use of arrays and microarrays, it is contemplated that a number of different assays could be employed to analyze miRNAs, their activities, and their effects. Such assays include, but are not limited to, digital color-coded barcode technology analysis, microarray expression profiling, quantitative PCR, reverse transcriptase PCR, reverse transcriptase real-time PCR, quantitative real-time PCR, end-point PCR, multiplex end-point PCR, cold PCR, ice-cold PCR, in situ hybridization, Northern hybridization, hybridization protection assay (HPA), branched DNA (bDNA) assay, rolling circle amplification (RCA), single molecule hybridization detection, invader assay, and/or Bridge Litigation Assay.

A nucleic acid microarray may be used to quantify the differential expression of a plurality of biomarkers. Microarray analysis may be performed using commercially available equipment, following manufacturer's protocols, such as by using the Affymetrix GeneChip® technology (Santa Clara, Calif.) or the Microarray System from Incyte (Fremont, Calif.). For example, single-stranded nucleic acids (e.g., miRNAs, cDNAs or oligonucleotides) are plated, or arrayed, on a microchip substrate. The arrayed sequences may be then hybridized with specific nucleic acid probes from the cells of interest. Fluorescently labeled cDNA probes may be generated through incorporation of fluorescently labeled deoxynucleotides by reverse transcription of RNA extracted from the cells of interest.

Alternatively, the RNA may be amplified by in vitro transcription and labeled with a marker, such as biotin. The labeled probes may then be hybridized to the immobilized nucleic acids on the microchip under highly stringent conditions. After stringent washing to remove the non-specifically bound probes, the chip may be scanned by confocal laser microscopy or by another detection method, such as a CCD camera. The raw fluorescence intensity data in the hybridization files may be preprocessed with the robust multichip average (RMA) algorithm to generate expression values.

Quantitative real-time PCR (qRT-PCR) may also be used to measure the differential expression of a plurality of biomarkers. In qRT-PCR, the RNA template is generally reverse transcribed into cDNA, which is then amplified via a PCR reaction. The amount of PCR product is followed cycle-by-cycle in real time, which allows for determination of the initial concentrations of miRNA. To measure the amount of PCR product, the reaction may be performed in the presence of a fluorescent dye, such as SYBR Green, which binds to double-stranded DNA. The reaction may also be performed with a fluorescent reporter probe that is specific for the DNA being amplified.

A non-limiting example of a fluorescent reporter probe is a TaqMan® probe (Applied Biosystems, Foster City, Calif.). The fluorescent reporter probe fluoresces when the quencher is removed during the PCR extension cycle. Multiplex qRT-PCR may be performed by using multiple gene-specific reporter probes, each of which contains a different fluorophore. Fluorescence values are recorded during each cycle and represent the amount of product amplified to that point in the amplification reaction.

To minimize errors and reduce any sample-to-sample variation, qRT-PCR may be performed using a reference standard. The ideal reference standard is expressed at a constant level among different tissues, and is unaffected by the experimental treatment. The level of miRNA in the original sample or the fold change in expression of each biomarker may be determined using calculations well known in the art.

Luminex® multiplexing microspheres may also be used to measure the differential expression of a plurality of biomarkers. These microscopic polystyrene beads are internally color-coded with fluorescent dyes, such that each bead has a unique spectral signature (of which there are up to 100). Beads with the same signature are tagged with a specific oligonucleotide or specific antibody that will bind the target of interest (i.e., biomarker miRNA). The target, in turn, is also tagged with a fluorescent reporter. Hence, there are two sources of color, one from the bead and the other from the reporter molecule on the target. The beads are then incubated with the sample containing the targets, of which up 100 may be detected in one well. The small size/surface area of the beads and the three dimensional exposure of the beads to the targets allows for nearly solution-phase kinetics during the binding reaction. The captured targets are detected by high-tech fluidics based upon flow cytometry in which lasers excite the internal dyes that identify each bead and also any reporter dye captured during the assay. The data from the acquisition files may be converted into expression values using means known in the art.

In situ hybridization may also be used to measure the differential expression of a plurality of biomarkers. This method permits the localization of miRNAs of interest in the cells of a tissue section. For this method, the tissue may be frozen, or fixed and embedded, and then cut into thin sections, which are arrayed and affixed on a solid surface. The tissue sections are incubated with a labeled antisense probe that will hybridize with an miRNA of interest. The hybridization and washing steps are generally performed under highly stringent conditions. The probe may be labeled with a fluorophore or a small tag (such as biotin or digoxigenin) that may be detected by another protein or antibody, such that the labeled hybrid may be detected and visualized under a microscope. Multiple miRNAs may be detected simultaneously, provided each antisense probe has a distinguishable label. The hybridized tissue array is generally scanned under a microscope. Because a sample of tissue from a subject with cancer may be heterogeneous, i.e., some cells may be normal and other cells may be cancerous, the percentage of positively stained cells in the tissue may be determined. This measurement, along with a quantification of the intensity of staining, may be used to generate an expression value for each biomarker.

The number of biomarkers whose expression is measured in a sample of cells from a subject with cancer may vary. Since the risk score is based upon the differential expression of the biomarkers, a higher degree of accuracy should be attained when the expression of more biomarkers is measured; however, a large number of biomarkers in the gene signature would hamper the clinical usefulness. In a certain embodiment, the differential expression of at least, at most, or about 20, 15, 10, 8, 6, 5, 4, 3 or 2 biomarkers (or any ranges or values derivable therein) may be measured.

D. Nucleic Acid Arrays

Certain aspects concern the preparation and use of miRNA arrays or miRNA probe arrays, which are ordered macroarrays or microarrays of nucleic acid molecules (probes) that are fully or nearly complementary or identical to a plurality of miRNA molecules or precursor miRNA molecules and are positioned on a support or support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters.

Representative methods and apparatus for preparing a microarray have been described, for example, in U.S. Pat. Nos. 5,143,854; 5,202,231; 5,242,974; 5,288,644; 5,324, 633; 5,384,261; 5,405,783; 5,412,087; 5,424,186; 5,429, 807; 5,432,049; 5,436,327; 5,445,934; 5,468,613; 5,470, 710; 5,472,672; 5,492,806; 5,503,980; 5,510,270; 5,525, 464; 5,527,681; 5,529,756; 5,532,128; 5,545,531; 5,547, 839; 5,554,501; 5,556,752; 5,561,071; 5,571,639; 5,580, 726; 5,580,732; 5,593,839; 5,599,695; 5,599,672; 5,610, 287; 5,624,711; 5,631,134; 5,639,603; 5,654,413; 5,658, 734; 5,661,028; 5,665,547; 5,667,972; 5,695,940; 5,700, 637; 5,744,305; 5,800,992; 5,807,522; 5,830,645; 5,837, 196; 5,871,928; 5,847,219; 5,876,932; 5,919,626; 6,004, 755; 6,087,102; 6,368,799; 6,383,749; 6,617,112; 6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO 0138580; WO 0168255; WO 03020898; WO 03040410; WO 03053586; WO 03087297; WO 03091426; WO 03100012; WO 04020085; WO 04027093; EP 373 203; EP 785 280; EP 799 897 and UK 8,803 000; the disclosures of which are all herein incorporated by reference. Moreover, a person of ordinary skill in the art could readily analyze data generated using an array. Such protocols are disclosed above, and include information found in WO 9743450; WO 03023058; WO 03022421; WO 03029485; WO 03067217; WO 03066906; WO 03076928; WO 03093810; WO 03100448A1, all of which are specifically incorporated by reference.

Some embodiments involve the preparation and use of miRNA anays or miRNA probe arrays, which are ordered macroarrays or microarrays of nucleic acid molecules (probes) that are fully or nearly complementary or identical to a plurality of miRNA molecules or precursor miRNA molecules and that are positioned on a support or support material in a spatially separated organization. Macroarrays are typically sheets of nitrocellulose or nylon upon which probes have been spotted. Microarrays position the nucleic acid probes more densely such that up to 10,000 nucleic acid molecules can be fit into a region typically 1 to 4 square centimeters. Microarrays can be fabricated by spotting nucleic acid molecules, e.g., genes, oligonucleotides, etc., onto substrates or fabricating oligonucleotide sequences in situ on a substrate. Spotted or fabricated nucleic acid molecules can be applied in a high density matrix pattern of up to about 30 non-identical nucleic acid molecules per square centimeter or higher, e.g. up to about 100 or even 1000 per square centimeter. Microarrays typically use coated glass as the solid support, in contrast to the nitrocellulose-based material of filter arrays. By having an ordered array of miRNA-complementing nucleic acid samples, the position of each sample can be tracked and linked to the original sample. A variety of different array devices in which a plurality of distinct nucleic acid probes are stably associated with the surface of a solid support are known to those of skill in the art. Useful substrates for arrays include nylon, glass, metal, plastic, and silicon. Such arrays may vary in a number of different ways, including average probe length, sequence or types of probes, nature of bond between the probe and the array surface, e.g. covalent or non-covalent, and the like. The labeling and screening methods are not limited by with respect to any parameter except that the probes detect miRNA; consequently, methods and compositions may be used with a variety of different types of miRNA arrays.

Representative methods and apparatuses for preparing a microarray have been described, for example, in U.S. Pat. Nos. 5,143,854; 5,202,231; 5,242,974; 5,288,644; 5,324,633; 5,384,261; 5,405,783; 5,412,087; 5,424,186; 5,429,807; 5,432,049; 5,436,327; 5,445,934; 5,468,613; 5,470,710; 5,472,672; 5,492,806; 5,525,464; 5,503,980; 5,510,270; 5,525,464; 5,527,681; 5,529,756; 5,532,128; 5,545,531; 5,547,839; 5,554,501; 5,556,752; 5,561,071; 5,571,639; 5,580,726; 5,580,732; 5,593,839; 5,599,695; 5,599,672; 5,610,287; 5,624,711; 5,631,134; 5,639,603; 5,654,413; 5,658,734; 5,661,028; 5,665,547; 5,667,972; 5,695,940; 5,700,637; 5,744,305; 5,800,992; 5,807,522; 5,830,645; 5,837,196; 5,871,928; 5,847,219; 5,876,932; 5,919,626; 6,004,755; 6,087,102; 6,368,799; 6,383,749; 6,617,112; 6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO 0138580; WO 0168255; WO 03020898; WO 03040410; WO 03053586; WO 03087297; WO 03091426; WO 03100012; WO 04020085; WO 04027093; EP 373 203; EP 785 280; EP 799 897 and UK 8 803 000, which are each herein incorporated by reference.

It is contemplated that the arrays can be high density arrays, such that they contain 2, 20, 25, 50, 80, 100, or more, or any integer derivable therein, different probes. It is contemplated that they may contain 1000, 16,000, 65,000, 250,000 or 1,000,000 or more, or any interger or range derivable therein, different probes. The probes can be directed to targets in one or more different organisms or cell types. In some embodiments, the oligonucleotide probes may range from 5 to 50, 5 to 45, 10 to 40, 9 to 34, or 15 to 40 nucleotides in length. In certain embodiments, the oligonucleotide probes are 5, 10, 15, 20, 25, 30, 35, 40 nucleotides in length, including all integers and ranges there between.

Moreover, the large number of different probes can occupy a relatively small area providing a high density array having a probe density of generally greater than about 60, 100, 600, 1000, 5,000, 10,000, 40,000, 100,000, or 400,000 different oligonucleotide probes per $cm^2$. The surface area of the array can be about or less than about 1, 1.6, 2, 3, 4, 5, 6, 7, 8, 9, or 10 $cm^2$.

Moreover, a person of ordinary skill in the art could readily analyze data generated using an array. Such protocols are disclosed herein or may be found in, for example, WO 9743450; WO 03023058; WO 03022421; WO 03029485; WO 03067217; WO 03066906; WO 03076928; WO 03093810; WO 03100448A1, all of which are specifically incorporated by reference.

E. Hybridization

After an array or a set of miRNA probes is prepared and the miRNA in the sample is labeled, the population of target nucleic acids may be contacted with the array or probes under hybridization conditions, where such conditions can be adjusted, as desired, to provide for an optimum level of specificity in view of the particular assay being performed. Suitable hybridization conditions are well known to those of skill in the art and reviewed in Sambrook et al. (2001) and WO 95/21944. Of particular interest in many embodiments is the use of stringent conditions during hybridization. Stringent conditions are known to those of skill in the art.

F. Labels and Labeling Techniques

In some embodiments, methods concern miRNA that are directly or indirectly labeled. It is contemplated that miRNA may first be isolated and/or purified prior to labeling. This may achieve a reaction that more efficiently labels the miRNA, as opposed to other RNA in a sample in which the miRNA is not isolated or purified prior to labeling. In many embodiments, the label is non-radioactive. Generally, nucleic acids may be labeled by adding labeled nucleotides (one-step process) or adding nucleotides and labeling the added nucleotides (two-step process).

In some embodiments, nucleic acids are labeled by catalytically adding to the nucleic acid an already labeled nucleotide or nucleotides. One or more labeled nucleotides can be added to miRNA molecules. See U.S. Pat. No. 6,723,509, which is hereby incorporated by reference.

In other embodiments, an unlabeled nucleotide or nucleotides may be catalytically added to a miRNA, and the unlabeled nucleotide is modified with a chemical moiety that enables it to be subsequently labeled. In some embodiments, the chemical moiety is a reactive amine such that the nucleotide is an amine-modified nucleotide. Examples of amine-modified nucleotides are well known to those of skill in the art, many being commercially available such as from Ambion, Sigma, Jena Bioscience, and TriLink.

In contrast to labeling of cDNA during its synthesis, the issue for labeling miRNA is how to label the already existing molecule. In some methods, embodiments concern the use of an enzyme capable of using a di- or tri-phosphate ribonucleotide or deoxytibonucleotide as a substrate for its addition to a miRNA. Moreover, in specific embodiments, it involves using a modified di- or tri-phosphate ribonucleotide, which is added to the 3' end of a miRNA. The source of the enzyme is not limiting. Examples of sources for the enzymes include yeast, gram-negative bacteria such as *E. coli, Lactococcus lactis*, and sheep pox virus.

Enzymes capable of adding such nucleotides include, but are not limited to, poly(A) polymerase, terminal transferase, and polynucleotide phosphorylase. In specific embodiments, a ligase is contemplated as not being the enzyme used to add the label, and instead, a non-ligase enzyme is employed. Terminal transferase catalyzes the addition of nucleotides to the 3' terminus of a nucleic acid. Polynucleotide phosphorylase can polymerize nucleotide diphosphates without the need for a primer.

Labels on miRNA or miRNA probes may be colorimetric (includes visible and UV spectrum, including fluorescent), luminescent, enzymatic, or positron emitting (including radioactive). The label may be detected directly or indirectly. Radioactive labels include $^{125}$I, $^{32}$P, $^{33}$P, and $^{35}$S. Examples of enzymatic labels include alkaline phosphatase, luciferase, horseradish peroxidase, and β-galactosidase. Labels can also be proteins with luminescent properties, e.g., green fluorescent protein and phycoerythrin.

The colorimetric and fluorescent labels contemplated for use as conjugates include, but are not limited to, Alexa Fluor dyes, BODIPY dyes, such as BODIPY FL; Cascade Blue; Cascade Yellow; coumarin and its derivatives, such as 7-amino-4-methylcoumarin, aminocoumarin and hydroxycoumarin; cyanine dyes, such as Cy3 and Cy5; eosins and erythrosins; fluorescein and its derivatives, such as fluorescein isothiocyanate; macrocyclic chelates of lanthanide ions, such as Quantum Dye™; Marina Blue; Oregon Green; rhodamine dyes, such as rhodamine red, tetramethylrhodamine and rhodamine 6G; Texas Red; fluorescent energy transfer dyes, such as thiazole orange-ethidium heterodimer; and, TOTAB.

Specific examples of dyes include, but are not limited to, those identified above and the following: Alexa Fluor 350, Alexa Fluor 405, Alexa Fluor 430, Alexa Fluor 488, Alexa Fluor 500. Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and, Alexa Fluor 750; amine-reactive BODIPY dyes, such as BODIPY 493/503, BODIPY 530/550, BODIPY 558/568, BODIPY 564/570, BODIPY 576/589, BODIPY 581/591, BODIPY 630/650, BODIPY 650/655, BODIPY FL, BODIPY R6G, BODIPY TMR, and, BODIPY-TR; Cy3, Cy5, 6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, SYPRO, TAMRA, 2',4',5',7'-Tetrabromosulfonefluorescein, and TET.

Specific examples of fluorescently labeled ribonucleotides are available from Molecular Probes, and these include, Alexa Fluor 488-5-UTP, Fluorescein-12-UTP, BODIPY FL-14-UTP, BODIPY TMR-14-UTP, Tetramethylrhodamine-6-UTP, Alexa Fluor 546-14-UTP, Texas Red-5-UTP, and BODIPY TR-14-UTP. Other fluorescent ribonucleotides are available from Amersham Biosciences, such as Cy3-UTP and Cy5-UTP.

Examples of fluorescently labeled deoxyribonucleotides include Dinitrophenyl (DNP)-11-dUTP, Cascade Blue-7-dUTP, Alexa Fluor 488-5-dUTP, Fluorescein-12-dUTP, Oregon Green 488-5-dUTP, BODIPY FL-14-dUTP, Rhodamine Green-5-dUTP, Alexa Fluor 532-5-dUTP, BODIPY TMR-14-dUTP, Tetramethylrhodamine-6-dUTP, Alexa Fluor 546-14-dUTP, Alexa Fluor 568-5-dUTP, Texas Red-12-dUTP, Texas Red-5-dUTP, BODIPY TR-14-dUTP, Alexa Fluor 594-5-dUTP, BODIPY 630/650-14-dUTP, BODIPY 650/665-14-dUTP; Alexa Fluor 488-7-OBEA-dCTP, Alexa Fluor 546-16-OBEA-dCTP, Alexa Fluor 594-7-OBEA-dCTP, Alexa Fluor 647-12-OBEA-dCTP.

It is contemplated that nucleic acids may be labeled with two different labels. Furthermore, fluorescence resonance energy transfer (FRET) may be employed in methods (e.g., Klostermeier et al., 2002; Emptage, 2001; Didenko, 2001, each incorporated by reference).

Alternatively, the label may not be detectable per se, but indirectly detectable or allowing for the isolation or separation of the targeted nucleic acid. For example, the label could be biotin, digoxigenin, polyvalent cations, chelator groups and the other ligands, include ligands for an antibody.

A number of techniques for visualizing or detecting labeled nucleic acids are readily available. Such techniques include, microscopy, arrays, Fluorometry, Light cyclers or other real time PCR machines, FACS analysis, scintillation counters, Phosphoimagers, Geiger counters, MRI, CAT, antibody-based detection methods (Westerns, immunofluorescence, immunohistochemistry), histochemical techniques, HPLC (Griffey et al., 1997), spectroscopy, capillary gel electrophoresis (Cummins et al., 1996), spectroscopy; mass spectroscopy; radiological techniques; and mass balance techniques.

When two or more differentially colored labels are employed, fluorescent resonance energy transfer (FRET) techniques may be employed to characterize association of one or more nucleic acid. Furthermore, a person of ordinary skill in the art is well aware of ways of visualizing, identifying, and characterizing labeled nucleic acids, and accordingly, such protocols may be used as part of some embodiments. Examples of tools that may be used also include fluorescent microscopy, a BioAnalyzer, a plate reader, Storm (Molecular Dynamics), Array Scanner, FACS (fluorescent activated cell smier), or any instrument that has the ability to excite and detect a fluorescent molecule.

G. Differential Expression Analyses

Methods can be used to detect differences in miRNA expression or levels between two samples, or a sample and a reference (e.g., a tissue or other biological reference or a digital reference representative of a non-cancerous state). Specifically contemplated applications include identifying and/or quantifying differences between miRNA from a sample that is normal and from a sample that is not normal, between a cancerous condition and a non-cancerous condition, or between two differently treated samples (e.g., a pretreatment versus a posttreatment sample). Also, miRNA may be compared between a sample believed to be susceptible to a particular therapy, disease, or condition and one believed to be not susceptible or resistant to that therapy, disease, or condition. A sample that is not normal is one exhibiting phenotypic trait(s) of a disease or condition or one believed to be not normal with respect to that disease or condition. It may be compared to a cell that is normal relative to that disease or condition. Phenotypic traits include symptoms of a disease or condition of which a component is or may or may not be genetic or caused by a hyperproliferative or neoplastic cell or cells, such as nodules or tumors.

Phenotypic traits also include characteristics such as longevity, morbidity, appearance (e.g., baldness, obesity), strength, speed, endurance, fertility, susceptibility or receptivity to particular drugs or therapeutic treatments (drug efficacy), and risk of drug toxicity.

In certain embodiments, miRNA profiles may be generated to evaluate and correlate those profiles with pharmacokinetics. For example, miRNA profiles may be created and evaluated for patient tumor and blood samples prior to the patient's being treated or during treatment to determine if there are miRNAs whose expression correlates with the outcome of treatment. Identification of differential miRNAs can lead to a diagnostic assay involving them that can be used to evaluate tumor and/or blood samples to determine what drug regimen the patient should be provided. In addition, it can be used to identify or select patients suitable for a particular clinical trial. If a miRNA profile is determined to be correlated with drug efficacy or drug toxicity that determination may be relevant to whether that patient is an appropriate patient for receiving the drug or for a particular dosage of the drug.

In addition to the above assay, blood samples from patients can be evaluated to identify a disease or a condition based on miRNA levels, such as primary CRC, dysplasia or a metastatic disease. A diagnostic assay can be created based on the profiles that doctors can use to identify individuals with a disease or a prognostic assay to determine or identify those individuals that who are at risk to develop a disease or condition such as metastasis. Alternatively, treatments can be designed based on miRNA profiling. Examples of such methods and compositions are described in the U.S. Provisional Patent Application entitled "Methods and Compositions Involving miRNA and miRNA Inhibitor Molecules" filed on May 23, 2005, which is hereby incorporated by reference in its entirety.

In certain aspects, this invention entails measuring expression of one or more biomarkers in a sample of cells from a subject with cancer. The expression information may be obtained by testing cancer samples by a lab, a technician, a device, or a clinician.

The pattern or signature of expression in each sample may then be used to generate a risk score for cancer prognosis or classification, such as predicting cancer survival or recurrence. The level of expression of a biomarker may be increased or decreased in a subject relative to other subjects with cancer. The expression of a biomarker may be higher in long-term survivors than in short-term survivors. Alternatively, the expression of a biomarker may be higher in short-term survivors than in long-term survivors.

Expression of one or more of biomarkers identified herein could be assessed to predict or report prognosis or prescribe treatment options for cancer patients, especially colorectal cancer patients.

V. CANCERS AND SIGNALING PATHWAYS

It is specifically contemplated that embodiments can be used to evaluate differences between stages of disease, such as between hyperplasia, dysplasia, neoplasia, pre-cancer and cancer, or between a primary tumor and a metastasized tumor.

As used herein, the terms "neoplastic cells" and "neoplasia" may be used interchangeably and refer to cells which exhibit relatively autonomous growth, so that they exhibit an aberrant growth phenotype characterized by a significant loss of control of cell proliferation. Neoplastic cells can be malignant or benign. In particular aspects, a neoplasia includes both dysplasia and cancer. Neoplasms may be benign, pre-malignant (carcinoma in situ or dysplasia) or malignant (cancer). Neoplastic cells may form a lump (i.e., a tumor) or not.

The term "dysplasia" may be used when the cellular abnormality is restricted to the originating tissue, as in the case of an early, in-situ neoplasm. Dysplasia may be indicative of an early neoplastic process. The term "cancer" may refer to a malignant neoplasm, including a broad group of various diseases involving unregulated cell growth.

Metastasis, or metastatic disease, may refer to the spread of a cancer from one organ or part to another non-adjacent organ or part. The new occurrences of disease thus generated may be referred to as metastases.

Cancers that may be evaluated by the disclosed methods and compositions include cancer cells particularly from the pancreas, including pancreatic ductal adenocarcinoma (PDAC), but may also include cells and cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; cerummous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma;

adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. Moreover, miRNAs can be evaluated in precancers, such as metaplasia, dysplasia, and hyperplasia.

It is specifically contemplated that the disclosed methods and compositions can be used to evaluate differences between stages of disease, such as between hyperplasia, neoplasia, pre-cancer and cancer, or between a primary tumor and a metastasized tumor.

Moreover, it is contemplated that samples that have differences in the activity of certain pathways may also be compared. These pathways include the following and those involving the following factors: antibody response, apoptosis, calcium/NFAT signaling, cell cycle, cell migration, cell adhesion, cell division, cytokines and cytokine receptors, drug metabolism, growth factors and growth factor receptors, inflammatory response, insulin signaling, $NF_K$-B signaling, angiogenesis, adipogenesis, cell adhesion, viral infection, bacterial infection, senescence, motility, glucose transport, stress response, oxidation, aging, telomere extension, telomere shortening, neural transmission, blood clotting, stem cell differentiation, G-Protein Coupled Receptor (GPCR) signaling, and p53 activation.

Cellular pathways that may be profiled also include but are not limited to the following: any adhesion or motility pathway including but not limited to those involving cyclic AMP, protein kinase A, G-protein couple receptors, adenylyl cyclase, L-selectin, E-selectin, PECAM, VCAM-1, α-actinin, paxillin, cadherins, AKT, integrin-α, integrin-β, RAF-1, ERK, PI-3 kinase, vinculin, matrix metalloproteinases, Rho GTPases, p85, trefoil factors, profilin, FAK, MAP kinase, Ras, caveolin, calpain-1, calpain-2, epidermal growth factor receptor, ICAM-1, ICAM-2, cofilin, actin, gelsolin, RhoA, RAC1, myosin light chain kinase, platelet-derived growth factor receptor or ezrin; any apoptosis pathway including but not limited to those involving AKT, Fas ligand, $NF_KB$, caspase-9, PI3 kinase, caspase-3, caspase-7, ICAD, CAD, EndoG, Granzyme B, Bad, Bax, Bid, Bak, APAF-1, cytochrome C, p53, ATM, Bcl-2, PARP, Chk1, Chk2, p21, c-Jun, p73, Rad51, Mdm2, Rad50, c-Abl, BRCA-1, perforin, caspase-4, caspase-8, caspase-6, caspase-1, caspase-2, caspase-10, Rho, Jun kinase, Jun kinase kinase, Rip2, lamin-A, lamin-B1, lamin-B2, Fas receptor, $H_2O_2$, Granzyme A, NADPH oxidase, HMG2, CD4, CD28, CD3, TRADD, IKK, FADD, GADD45, DR3 death receptor, DR4/5 death receptor, FLIPs, APO-3, GRB2, SHC, ERK, MEK, RAF-1, cyclic AMP, protein kinase A, E2F, retinoblastoma protein, Smac/Diablo, ACH receptor, 14-3-3, FAK, SODD, TNF receptor, RIP, cyclin-D1, PCNA, Bcl-XL, PIP2, PIP3, PTEN, ATM, Cdc2, protein kinase C, calcineurin, IKKα, IKKβ, IKKγ, SOS-1, c-FOS, Traf-1, Traf-2, Iκβ or the proteasome; any cell activation pathway including but not limited to those involving protein kinase A, nitric oxide, caveolin-1, actin, calcium, protein kinase C, Cdc2, cyclin B, Cdc25, GRB2, SRC protein kinase, ADP-ribosylation factors (ARFs), phospholipase D, AKAP95, p68, Aurora B, CDK1, Eg7, histone H3, PKAc, CD80, PI3 kinase, WASP, Arp2, Arp3, p16, p34, p20, PP2A, angiotensin, angiotensin-converting enzyme, protease-activated receptor-1, protease-activated receptor-4, Ras, RAF-1, PLCβ, PLCγ, COX-1, G-protein-coupled receptors, phospholipase A2, IP3, SUMO 1, SUMO 2/3, ubiquitin, Ran, Ran-GAP, Ran-GEF, p53, glucocorticoids, glucocorticoid receptor, components of the SWI/SNF complex, RanBP1, RanBP2, importins, exportins, RCCI, CD40, CD40 ligand, p38, IKKα, IKKβ, NFκB, TRAF2, TRAF3, TRAFS, TRAF6, IL-4, IL-4 receptor, CDKS, AP-I transcription factor, CD45, CD4, T cell receptors, MAP kinase, nerve growth factor, nerve growth factor receptor, c-Jun, c-Fos, Jun kinase, GRB2, SOS-1, ERK-1, ERK, JAK2, STAT4, IL-12, IL-12 receptor, nitric oxide synthase, TYK2, IFNγ, elastase, IL-8, epithelins, IL-2, IL-2 receptor, CD28, SMAD3, SMAD4, TGFβ or TGFβ receptor; any cell cycle regulation, signaling or differentiation pathway including but not limited to those involving TNFs, SRC protein kinase, Cdc2, cyclin B, Grb2, Sos-1, SHC, p68, Aurora kinases, protein kinase A, protein kinase C, Eg7, p53, cyclins, cyclin-dependent kinases, neural growth factor, epidermal growth factor, retinoblastoma protein, ATF-2, ATM, ATR, AKT, CHK1, CHK2, 14-3-3, WEE1, CDC25 CDC6, Origin Recognition Complex proteins, p15, p16, p2'7, p21, ABL, c-ABL, SMADs, ubiquitin, SUMO, heat shock proteins, Wnt, GSK-3, angiotensin, p73 any PPAR, TGFα, TGFβ, p300, MDM2, GADD45, Notch, cdc34, BRCA-1, BRCA-2, SKPI, the proteasome, CUL1, E2F, p107, steroid hormones, steroid hormone receptors, 1κBα, 1κBβ, Sin3A, heat shock proteins, Ras, Rho, ERKs, IKKs, PI3 kinase, Bcl-2, Bax, PCNA, MAP kinases, dynein, RhoA, PKAc, cyclin AMP, FAK, PIP2, PIP3, integrins, thrombopoietin, Fas, Fas ligand, PLK3, MEKs, JAKs, STATs, acetylcholine, paxillin calcineurin, p38, importins, exportins, Ran, Rad50, Rad51, DNA polymerase, RNA polymerase, Ran-GAP, Ran-GEF, NuMA, Tpx2, RCC1, Sonic Hedgehog, Crm1, Patched (Ptc-1), MPF, CaM kinases, tubulin, actin, kinetochore-associated proteins, centromere-binding proteins, telomerase, TERT, PP2A, c-MYC, insulin, T cell receptors, B cell receptors, CBP, IKβ, NFκB, RAC1, RAFI, EPO, diacylglycerol, c-Jun, c-Fos, Jun kinase, hypoxia-inducible factors, GATA4, β-catenin, α-catenin, calcium, arrestin, survivin, caspases, procaspases, CREB, CREM, cadherins, PECAMs, corticosteroids, colony-stimulating factors, calpains, adenylyl cyclase, growth factors, nitric oxide, transmembrane receptors, retinoids, G-proteins, ion channels, transcriptional activators, transcriptional coactivators, transcriptional repressors, interleukins, vitamins, interferons, transcriptional corepressors, the nuclear pore, nitrogen, toxins, proteolysis, or phosphorylation; or any metabolic pathway including but not limited to those involving the biosynthesis of amino acids, oxidation of fatty acids, biosynthesis of neurotransmitters and other cell signaling molecules, biosynthesis of polyamines, biosynthesis of lipids and sphingolipids, catabolism of amino acids and nutrients, nucleotide synthesis, eicosanoids, electron transport reactions, ER-associated degradation, glycolysis, fibrinolysis, formation of ketone bodies, formation of phagosomes, cholesterol metabolism, regulation of food intake, energy homeostasis, prothrombin activation, synthesis of lactose and other sugars, multi-drug resistance, biosynthesis of phosphatidylcholine, the proteasome, amyloid precursor protein, Rab GTPases, starch synthesis, glycosylation, synthesis of phoshoglycerides, vitamins, the citric acid cycle, IGF-1 receptor, the urea cycle, vesicular transport, or salvage pathways. It is further contemplated that the disclosed nucleic acids molecules can be employed in diagnostic and therapeutic methods with respect to any of the above pathways or factors. Thus, in some embodiments, a miRNA may be differentially expressed with respect to one or more of the above pathways or factors.

VI. MARKER-BASED PROGNOSIS OR DIAGNOSIS

A. Evaluation of Expression Levels

A variety of different models can be employed to evaluate expression levels and/or other comparative values based on expression levels of miRNAs (or their precursors or targets). One model is a logistic regression model (see the Wikipedia entry on the World Wide Web at en.wikipedia.com, which is hereby incorporated by reference).

Other examples of models include but are not limited to Decision Tree, Linear Disciminant Analysis, Neural Network, Support Vector Machine, and k-Nearest Neighbor Classifier. In certain embodiments, a scoring algorithm comprises a method selected from the group consisting of: Linear Discriminate Analysis (LDA), Significance Analysis of Microarrays, Tree Harvesting, CART, MARS, Self Organizing Maps, Frequent Item Set, Bayesian networks, Prediction Analysis of Microarray (PAM), SMO, Simple Logistic Regression, Logistic Regression, Multilayer Perceptron, Bayes Net, Naive Bayes, Naive Bayes Simple, Naive Bayes Up, IB1, Ibk, Kstar, LWL, AdaBoost, ClassViaRegression, Decorate, Multiclass Classifier, Random Committee, j48, LMT, NBTree, Part, Random Forest, Ordinal Classifier, Sparse Linear Programming (SPLP), Sparse Logistic Regression (SPLR), Elastic NET, Support Vector Machine, Prediction of Residual Enor Sum of Squares (PRESS), and combinations thereof.

A person of ordinary skill in the art could use these different models to evaluate expression level data and comparative data involving expression levels of one or more miRs (or their precursors or their targets). In some embodiments, the underlying classification algorithm is linear discriminate analysis (LDA). LDA has been extensively studied in the machine learning literature, for example, Hastie et al. (2009) and Venables & Ripley (2002), which are both incorporated by reference.

Models may take into account one or more different comparison values or they may also take into account differential expression of one or more additional biomarkers. A diagnostic or risk score may be based on 1, 2, 3, 4, 5, 6, 7, 8 or more biomarkers (or any range derivable therein), but in some embodiments, it takes into account additionally or alternatively, 1, 2, 3, 4, 5, 6, 7, 8, 9, 10 or more miRNA expression levels (or any range derivable therein), wherein the miRNA expression level delectably differs between metastatic cells and cells that are not metastatic.

B. Risk Scores

In some embodiments, a score is prepared. The score may involve numbers such as 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, (or any range or a subset therein) in some embodiments.

For example, since use of hierarchical clustering methods in clinical practice may be difficult (Abdullah-Sayani et al., 2006), Risk Score (RS) methods using Cox regression coefficient of each gene (Chen et al., 2007) may be applied. For example, patients in independent cohort were dichotomized according to their RS.

The biomarkers are related to cancer diagnosis or prognosis, for example, prediction of dysplasia, early stage CRC, primary CRC, metastasis risk, survival, recurrence, or therapy response. In a particular embodiment, the differential patterns of expression of a plurality of these biomarkers may be used to predict the survival outcome of a subject with cancer. Certain biomarkers tend to be over-expressed in long-term survivors, whereas other biomarkers tend to be over-expressed in short-term survivors. The unique pattern of expression of a plurality of biomarkers in a subject (i.e., the gene signature) may be used to generate a risk score of survival. Subjects with a high risk score may have a short survival time (e.g., less than about 2 years) after surgical resection. Subjects with a low risk score may have a longer survival time (e.g., more than about 3 years) after resection.

In particular aspects, there may be provided biomarkers associated with early stage detection of CRC, prognostic or diagnostic biomarkers associated with colorectal cancer that may be used to identify subjects at risk associated with colorectal cancer or and/or identify subjects with a favorable or poor prognosis. Still further, certain aspects also included metastasis-associated biomarkers that may be used for identifying cells with metastatic potential within the primary tumor and hope for improving the prognosis of these metastatic-associated cancers. Additionally, by identifying the metastasis-associated biomarkers whose expression is changed in metastasis offers potential targets to inhibit metastasis.

Regardless of the technique used to measure the differential expression of a plurality of biomarkers, the expression of each biomarker may be converted into an expression value. These expression values then will be used to calculate a risk score of survival for a subject with cancer using statistical methods well known in the art. The risk scores may be calculated using a principal components analysis.

The risk scores may also be calculated using a partial Cox regression analysis. In a preferred embodiment, the risk scores may be calculated using a univariate Cox regression analysis.

The scores generated may be used to classify patients into high or low risk signature, wherein a high risk score is associated with a poor diagnosis, metastasis risk or prognosis, such as a short survival time or a poorer survival, and a low risk score is associated with a good diagnosis, metastasis risk, or prognosis, such as a long survival time or a better survival. The cut-off value may be derived from a control group of cancer patients as a median risk score.

In a particular embodiment of this method, a tissue sample may be collected from a subject with a cancer, for example, a colorectal cancer. The collection step may comprise surgical resection. The sample of tissue may be stored in RNA later or flash frozen, such that RNA may be isolated at a later date. miRNA may be isolated from the tissue and used to generate labeled probes for a nucleic acid microarray analysis. The miRNA may also be used as template for qRT-PCR in which the expression of a plurality of biomarkers is analyzed. The expression data generated may be used to derive a risk score, e.g., using the Cox regression classification method. The risk score may be used to predict whether the subject will be have a risk for developing cancer or metastasis or a short-term or a long-term cancer survivor.

VII. CANCER MANAGEMENT AND TREATMENT

Methods may involve the determination or selection of an appropriate cancer "management regimen" and predicting the outcome of the same. As used herein the phrase "management regimen" refers to a management plan that specifies the type of examination, screening, diagnosis, surveillance, care, and treatment (such as dosage, schedule and/or duration of a treatment) provided to a subject in need thereof (e.g., a subject diagnosed with cancer).

The selected treatment regimen can be an aggressive one which is expected to result in the best clinical outcome (e.g., complete cure of the disease) or a more moderate one which may relieve symptoms of the disease yet results in incomplete cure of the disease. The type of treatment can include a surgical intervention, administration of a therapeutic drug, an exposure to radiation therapy and/or any combination thereof. The dosage, schedule and duration of treatment can vary, depending on the severity of disease and the selected type of treatment, and those of skill in the art are capable of adjusting the type of treatment with the dosage, schedule and duration of treatment.

Biomarkers and a new "Risk Score" system that can predict the likelihood of tumor or cancer recurrence or overall survival in cancer patients can be used to identify patients who will get benefit of conventional single or combined modality therapy before treatment begins. In the same way, the invention can identify those patients who do not get much benefit from such conventional single or combined modality therapy and can offer them alternative treatment(s).

In certain aspects, further cancer or metastasis examination or screening such as fecal occult blood testing, flexible sigmoidoscopy and colonoscopy for colorectal cancer, or further diagnosis such as contrast enhanced computed tomography (CT), positron emission tomography-CT (PET-CT), and magnetic resonance imaging (MRI) may be performed for the detection of CRC or cancer metastasis in patients determined to at high risk based on the miRNA expression levels. In alternative aspects, there may be no need for further metastasis detection for patients determined to be at low risk based on the miRNA expression levels.

Non-limiting examples of screening tests include fecal occult blood testing, flexible sigmoidoscopy and colonoscopy. Sigmoidoscopy may not screen the right side of the colon where 42% of malignancies are found. Virtual colonoscopy via a CT scan appears as good as standard colonoscopy for detecting cancers and large adenomas but is expensive, associated with radiation exposure, and cannot remove any detected abnormal growths like standard colonoscopy can. A new screening method is the M2-PK Test. The enzyme biomarker M2-PK has been identified as a key enzyme in colorectal cancers and polyps. M2-PK does not depend on blood in the stool and is specifically related to changes in the tumour metabolism. It does not require any special preparation prior to testing. Only a small stool sample is needed. M2-PK features a high sensitivity for colorectal cancer and polyps and is able to detect bleeding and non-bleeding colorectal cancer and polyps. In the event of a positive result people would be asked to undergo further examination e.g. colonoscopy.

Fecal occult blood testing of the stool may be recommended every two years and can be either guaiac based or immunochemical. For those at high risk, screenings may be more frequent or more early as compared with recommended guidelines for people with average risk. For people with average risk who have had a high-quality colonoscopy with normal results, the American Gastroenterological Association does not recommend any type of screening in the 10 years following the colonoscopy. For people over 75 or those with a life expectancy of less than 10 years, screening may not be recommended.

In certain aspects of the present invention, conventional cancer therapy or therapy for early cancer may be applied to a subject wherein the subject is identified or reported as having a good prognosis or low risk of metastasis based on the assessment of the biomarkers as disclosed. In further embodiments, normal, low or moderate surveillance may be provided for patients with a favorable prognosis or biomarker profile or low risk of cancer or metastasis.

On the other hand, at least an alternative cancer therapy or metastasis therapy or care may be prescribed, as used alone or in combination with conventional cancer therapy, if a poor prognosis or high risk of metastasis is determined by the disclosed methods or kits. In further embodiments, intensive or aggressive surveillance may be provided for patients with an unfavorable prognosis or biomarker profile or high risk of cancer or metastasis.

Conventional cancer therapies include one or more selected from the group of chemical or radiation based treatments and surgery. Chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

Radiation therapy that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection m which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

Alternative cancer therapy include any cancer therapy other than surgery, chemotherapy and radiation therapy in the present invention, such as immunotherapy, gene therapy, hormonal therapy or a combination thereof. Subjects identified with poor prognosis using the present methods may not have favorable response to conventional treatment(s) alone and may be prescribed or administered one or more alternative cancer therapy per se or in combination with one or more conventional treatments.

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Gene therapy is the insertion of polynucleotides, including DNA or RNA, into an individual's cells and tissues to treat a disease. Antisense therapy is also a form of gene therapy in the present invention. A therapeutic polynucleotide may be administered before, after, or at the same time of a first cancer therapy. Delivery of a vector encoding a variety of proteins is encompassed within the invention. For example, cellular expression of the exogenous tumor suppressor oncogenes would exert their function to inhibit excessive cellular proliferation, such as p53, p16 and C-CAM.

Additional agents to be used to improve the therapeutic efficacy of treatment include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1 beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

Once the patient has been identified as being at high risk for metastasis, intensive or frequent surveillance of metastasis may be provided for monitoring metastasis. The high risk of metastasis usually correlates with a patient's likelihood of survival (e.g. the "prognosis").

Once a cancer has metastasized or is determined to be at high risk for metastasis, it may still be treated with radiosurgery, chemotherapy, radiation therapy, biological therapy, hormone therapy, surgery, or a combination of these interventions ("multimodal therapy"). The choice of treatment depends on a large number of factors, including the type of primary cancer, the size and location of the metastases, the patient's age and general health, and the types of treatments used previously, among others. The treatment options currently available are rarely able to cure metastatic cancer, though some tumors, such as testicular cancer and thyroid cancer, are usually still curable

VIII. KITS

The present invention also encompasses kits for performing the diagnostic and prognostic methods of the invention. Such kits can be prepared from readily available materials and reagents. For example, such kits can comprise any one or more of the following materials: enzymes, reaction tubes, buffers, detergent, primers and probes. In a particular embodiment, these kits allow a practitioner to obtain samples of neoplastic cells in blood, tears, semen, saliva, urine, tissue, serum, stool, sputum, cerebrospinal fluid and supernatant from cell lysate. In another preferred embodiment these kits include the needed apparatus for performing RNA extraction, RT-PCR, and gel electrophoresis. Instructions for performing the assays can also be included in the kits.

In a particular aspect, these kits may comprise a plurality of agents for assessing the differential expression of a plurality of biomarkers, wherein the kit is housed in a container. The kits may further comprise instructions for using the kit for assessing expression, means for converting the expression data into expression values and/or means for analyzing the expression values to generate scores that predict survival or prognosis. The agents in the kit for measuring biomarker expression may comprise a plurality of PCR probes and/or primers for qRT-PCR and/or a plurality of antibody or fragments thereof for assessing expression of the biomarkers. In another embodiment, the agents in the kit for measuring biomarker expression may comprise an array of polynucleotides complementary to the miRNA biomarkers. Possible means for converting the expression data into expression values and for analyzing the expression values to generate scores that predict survival or prognosis may be also included. For example, probes for detecting miRNAs are commercially available. Probes from Applied Biosystems were used for the expression assays that are described in the Examples. The probes of Applied Biosystems may be used to detect the miRNAs discussed herein.

Any of the compositions or components described herein may be comprised in a kit. In a non-limiting example, reagents for isolating miRNA, labeling miRNA, and/or evaluating a miRNA population using an array, nucleic acid amplification, and/or hybridization can be included in a kit, as well reagents for preparation of samples from colon samples. The kit may further include reagents for creating or synthesizing miRNA probes. The kits will thus comprise, in suitable container means, an enzyme for labeling the miRNA by incorporating labeled nucleotide or unlabeled nucleotides that are subsequently labeled. In certain aspects, the kit can include amplification reagents. In other aspects, the kit may include various supports, such as glass, nylon, polymeric beads, magnetic beads, and the like, and/or reagents for coupling any probes and/or target nucleic acids. It may also include one or more buffers, such as reaction buffer, labeling buffer, washing buffer, or a hybridization buffer, compounds for preparing the miRNA probes, and components for isolating miRNA. Other kits of the invention may include components for making a nucleic acid array comprising miRNA, and thus, may include, for example, a solid support.

Kits for implementing methods described herein are specifically contemplated. In some embodiments, there are kits for preparing miRNA for multi-labeling and kits for preparing miRNA probes and/or miRNA anays. In these embodiments, kit comprise, in suitable container means, 1, 2, 3, 4, 5, 6, 7, 8, 9, 10, 11, 12 or more of the following: (1) poly(A) polymerase; (2) unmodified nucleotides (G, A, T, C, and/or U); (3) a modified nucleotide (labeled or unlabeled); (4) poly(A) polymerase buffer; and, (5) at least one microfilter; (6) label that can be attached to a nucleotide; (7) at least one miRNA probe; (8) reaction buffer; (9) a miRNA array or components for making such an array; (10) acetic acid; (11) alcohol; (12) solutions for preparing, isolating, enriching, and purifying miRNAs or miRNA probes or arrays. Other reagents include those generally used for manipulating RNA, such as formamide, loading dye, ribonuclease inhibitors, and DNase.

In specific embodiments, kits may include an array containing miRNA probes, as described in the application. An array may have probes corresponding to all known miRNAs of an organism or a particular tissue or organ in particular conditions, or to a subset of such probes. The subset of probes on arrays of the invention may be or include those identified as relevant to a particular diagnostic, therapeutic, or prognostic application. For example, the array may contain one or more probes that is indicative or suggestive of (1) a disease or condition (thyroid cancer), (2) susceptibility or resistance to a particular drug or treatment; (3) susceptibility to toxicity from a drug or substance; (4) the stage of development or severity of a disease or condition (prognosis); and (5) genetic predisposition to a disease or condition.

For any kit embodiment, including an array, there can be nucleic acid molecules that contain or can be used to amplify a sequence that is a variant of, identical to or complementary to all or part of any of the sequences described herein. Any nucleic acid discussed above may be implemented as part of a kit.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly preferred.

However, the components of the kit may be provided as dried powder(s). When reagents and/or components are provided as a dry powder, the powder can be reconstituted by the addition of a suitable solvent. It is envisioned that the solvent may also be provided in another container means. In some embodiments, labeling dyes are provided as a dried power. It is contemplated that 10, 20, 30, 40, 50, 60, 70, 80, 90, 100, 120, 120, 130, 140, 150, 160, 170, 180, 190, 200, 300, 400, 500, 600, 700, 800, 900, 1000 µg or at least or at most those amounts of dried dye are provided in kits of the invention. The dye may then be resuspended in any suitable solvent, such as DMSO.

The container means will generally include at least one vial, test tube, flask, bottle, syringe and/or other container means, into which the nucleic acid formulations are placed, preferably, suitably allocated. The kits may also comprise a second container means for containing a sterile, pharmaceutically acceptable buffer and/or other diluent.

The kits may include a means for containing the vials in close confinement for commercial sale, such as, e.g., injection and/or blow-molded plastic containers into which the desired vials are retained.

Such kits may also include components that facilitate isolation of the labeled miRNA. It may also include components that preserve or maintain the miRNA or that protect against its degradation. Such components may be RNase-free or protect against RNases. Such kits generally will comprise, in suitable means, distinct containers for each individual reagent or solution.

A kit may also include instructions for employing the kit components as well the use of any other reagent not included in the kit. Instructions may include variations that can be implemented.

Kits may also include one or more of the following: Control RNA; nuclease-free water; RNase-free containers, such as 1.5 ml tubes; RNase-free elution tubes; PEG or dextran; ethanol; acetic acid; sodium acetate; ammonium acetate; guanidinium; detergent; nucleic acid size marker; RNase-free tube tips; and RNase or DNase inhibitors.

It is contemplated that such reagents are embodiments of kits. Such kits, however, are not limited to the particular items identified above and may include any reagent used for the manipulation or characterization of miRNA.

IX. TANGIBLE COMPUTER-READABLE MEDIUM

There may be provided Tangible computer-readable medium having computer usable program code executable to perform operations related to early detection, diagnosis or prognosis of cancer. A processor or processors can be used in performance of the operations driven by the example tangible computer-readable media disclosed herein. Alternatively, the processor or processors can perform those operations under hardware control, or under a combination of hardware and software control. For example, the processor may be a processor specifically configured to carry out one or more those operations, such as an application specific integrated circuit (ASIC) or a field programmable gate array (FPGA). The use of a processor or processors allows for the processing of information (e.g., data) that is not possible without the aid of a processor or processors, or at least not at the speed achievable with a processor or processors. Some embodiments of the performance of such operations may be achieved within a certain amount of time, such as an amount of time less than what it would take to perform the operations without the use of a computer system, processor, or processors, including no more than one hour, no more than 30 minutes, no more than 15 minutes, no more than 10 minutes, no more than one minute, no more than one second, and no more than every time interval in seconds between one second and one hour.

Some embodiments of the present tangible computer-readable media may be, for example, a CD-ROM, a DVD-ROM, a flash drive, a hard drive, or any other physical storage device. Some embodiments of the present methods may include recording a tangible computer-readable medium with computer-readable code that, when executed by a computer, causes the computer to perform any of the operations discussed herein, including those associated with the present tangible computer-readable media. Recording the tangible computer-readable medium may include, for example, burning data onto a CD-ROM or a DVD-ROM, or otherwise populating a physical storage device with the data.

X. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Identification of Metastasis-Related miRNAs

Materials and Methods.

A commercially available kit for miRNA extraction from cell lines, Formalin-Fixed, Paraffin-Embedded (FFPE) tissue, and human serum samples with some modifications. To compare miRNAs expression status between primary CRC and distant metastasized CRC, expression of fourteen metastasis-related miRNAs (let-7i, miR-10b, miR-30b, miR-34a, miR-141, miR-200b, miR-200c, miR-203, miR-221, miR-320a, miR-373, miR-429, miR-518d, and miR-520c) was analyzed in matched primary colorectal cancer and corresponding liver metastasis tissues from 59 patients. MicroRNA expression levels were determined by quantitative real-time PCR (qRT-PCR) and the data were normalized relative to miR-16 expression. The skilled artisan will recognize, however, that many different methods for determining expression can be used with certain aspects of the present invention, e.g., thin layer chromatography (TLC), high performance liquid chromatography (HPLC), mass spectrometry (MS), nanopore amperometry, nanopore sequencing, single-molecule, real-time (SM-RT) sequencing, endonuclease digestion, microarrays, matrix-assisted laser desorption ionization time-of-flight (MALDI-TOF) mass spectrometry, and next-generation sequencing (Laird, Peter W., "Principles and Challenges of Genomewide DNA Expression Analysis," Nature Review Genetics, Vol. 11, March 2010, pgs 191-203, relevant portions incorporated herein by reference).

The present example may include the use of digital color-coded barcode technology analysis (e.g., NANOSTRING® technology (such as the nCounter Analysis System, NanoString Technologies, Inc., Seattle, Wash.). The NANOSTRING® protocol includes the following steps: (1) Hybridization: two ~50 base probes per mRNA that hybridize in solution, a reporter probe that carries the signal, while a capture probe allows the complex to be immobilized for data collection. (2) Purification and Immobilization: following hybridization, excess probes are removed and the probe/target complexes are aligned and immobilized in, e.g., an nCounter Cartridge; and (3) Data is collected from the sample cartridges, which can be placed in the digital analyzer instrument for data acquisition using color codes on the surface of the cartridge that are counted and tabulated for each target molecule.

Cell lines and 5-aza-2-deoxy-cytidine treatment. Seven CRC cell lines, HCT116, RKO, SW48, Caco-2, HT29, SW480, and SW620 were obtained from the American Type Culture Collection (ATCC, Rockville, Md.). Cell lines were treated with 2.5 μM 5-Aza-2'-deoxycytidine (5-aza-dC; Sigma-Aldrich) for 72 hours, and fresh medium containing 5-aza-dC was replaced every 24 hours.

Tissue Specimens.

A total of 59 formalin-fixed, paraffin-embedded (FFPE) matched corresponding normal cololectal mucosa (NM), primary CRC tissues (PC), and liver metastasis tissues (LM)

were enrolled in this study. Written informed consent was obtained from all patients and the study was approved by the institutional review boards of all participating institutions. Careful microdissection was performed in order to enrich for tumor cells.

Isolation of RNA and DNA.

Total RNA (including miRNAs) from CRC cell lines was extracted using miRNeasy® Mini Kits (Qiagen). For RNA extraction from FFPE specimens, a Total Nucleic Acid Isolation Kit for FFPE tissues (Ambion, Austin, Tex., USA) was used according to the manufacturer's instructions. DNA was extracted from CRC cell lines using a QIAamp® DNA Mini Kit (Qiagen) and from FFPE specimens using a QIAamp® DNA FFPE Tissue Kit (Qiagen).

miRNA Expression Analysis.

Expression of fourteen metastasis-related miRNAs (let-7i, miR-10b, miR-30b, miR-34a, miR-141, miR-200b, miR-200c, miR-203, miR-221, miR-320a, miR-373, miR-429, miR-518d, and miR-520c) was analyzed using TaqMan miRNA assays (Applied Biosystems Inc., Foster City, Calif.). Expression of RNU6B (Applied Biosystems Inc., Foster City, Calif.) and miR-16 were used as endogenous controls for cell lines and FFPE tissues, respectively.

DNA Expression Analysis.

Expression levels of repetitive sequences (global Alu and local Alu) were analyzed by quantitative bisulfite pyrosequencing using the PSQ HS 96A pyrosequencing system (Qiagen) following bisulfite modification of genomic DNA using EZ DNA expression Gold Kits (Zymo Research), as described previously.

Statistical Analysis.

Data were analyzed with GraphPad Prism 5.0 software. To evaluate significant differences between two matched pair groups of samples, paired t-tests was used, whereas the difference between two independent groups of samples was analyzed using the Mann-Whitney U test.

Additional Materials and Methods.

CRC Cell line: CACO2, HCT116, RKO, SW48, SW480, and SW620. Tissue specimens: A total of 59 formalin-fixed, paraffin-embedded (FFPE) primary CRC tissues and corresponding liver metastasis tissues were analyzed. 5-Aza-2'-deoxycytidine (5-aza-dC) treatment: CRC cell lines were treated with 2.5 µM 5-aza-dC for 72 hours. α-amanitin treatment: CRC cell lines were treated with 50 µg/ml α-amanitin, a RNA pol II inhibitor, for 7 hours. Expression analysis: Expression levels were analyzed by bisulfite pyrosequencing for quantitative expression analysis using PSQ HS 96A pyrosequencing system (Qiagen) on bisulfite modified genomic DNA template. microRNAs expression analysis: Expression of miR-373 and miR-520c was analyzed using TaqMan miRNA assays.

FIG. 1 shows a metastasis predictive microRNAs expression colorectal cancer (CRC). Briefly, all 10 metastasis predictive candidate miRNAs expression status in matched corresponding primary CRC (PC) and liver metastasized CRC (LM) human tissues by qRT-PCR. Five miRNAs (let7i, miR-10b, miR-200b, miR-221, and miR-320) were significantly down-regulated in LM compared to PC. On the contrary, three miRNAs (miR-141, miR-200c, and miR-203) were significantly up-regulated in LM compared to PC.

Figure 2:
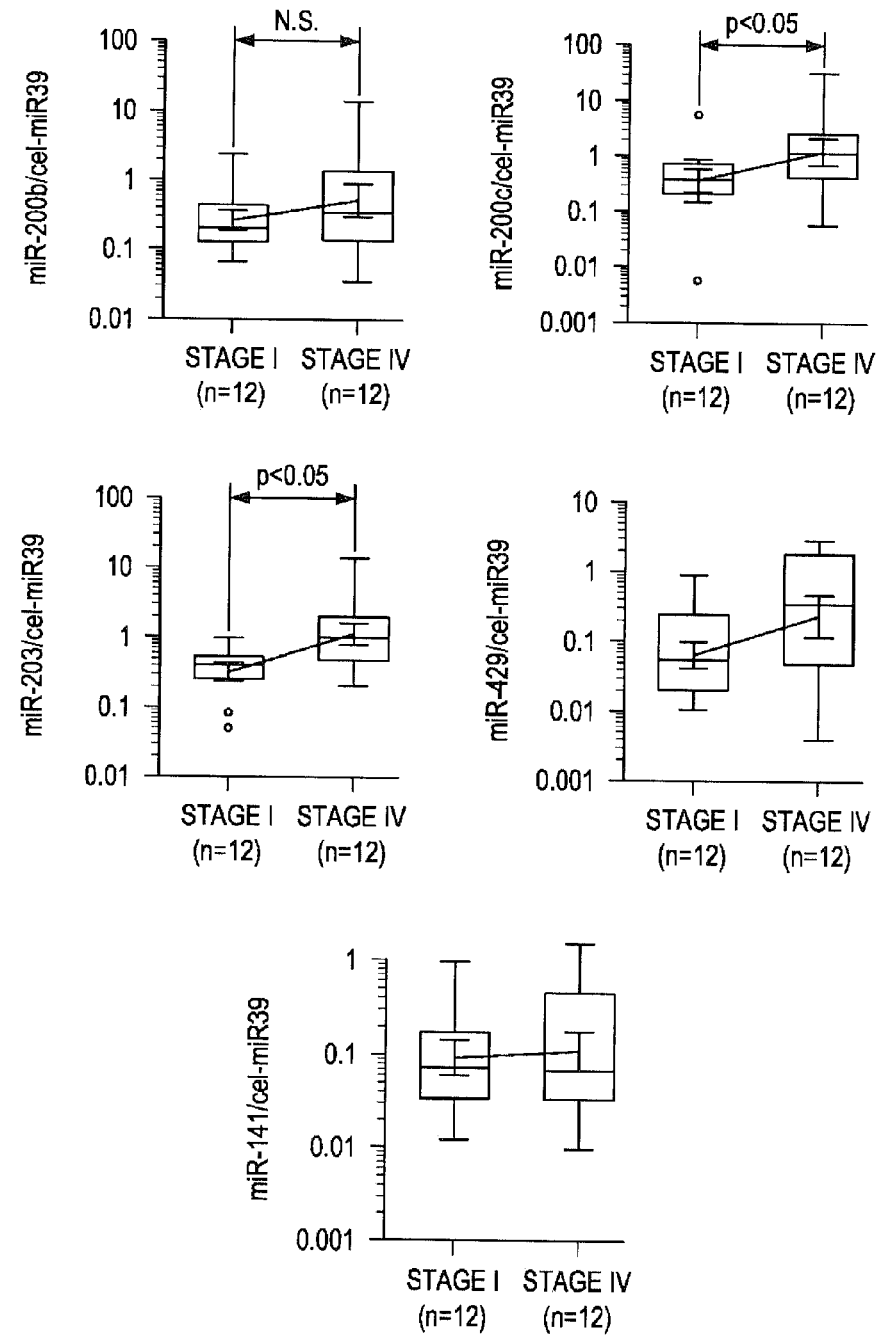
FIG. 2—FIG. 2 is an analysis of the expression of the miR-200 family (-200b, -200c, -141 and -429), and miR-203 in serum samples from CRC patients with metastasis (Stage IV) and without metastasis (Stage I) by qRT-PCR. The expression of mir-200c and miR-203 were significantly elevated in serum samples from CRC patients with metastasis (Stage IV) compared to patients without metastasis (Stage I).

FIG. 2 is an analysis of the expression of the miR-200 family (-200b, -200c, -141 and -429), and miR-203 in serum samples from CRC patients with metastasis (Stage IV) and without metastasis (Stage I) by qRT-PCR. The expression of mir-200c and miR-203 were significantly elevated in serum samples from CRC patients with metastasis (Stage IV) compared to patients without metastasis (Stage I). These data strongly indicate that the invented miRNAs are useful biomarker for CRC metastasis prediction.

Figure 3:
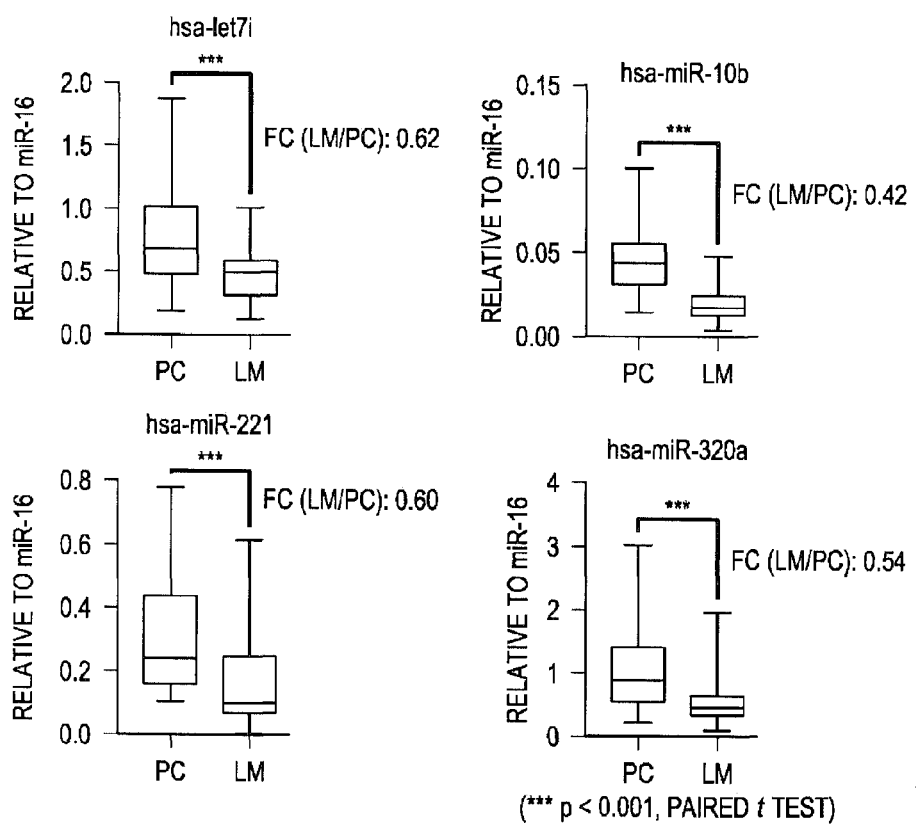
FIG. 3—shows the results of the qRT-PCR validation for selected miRNAs in 58 PCs and LMs.
Figure 4:
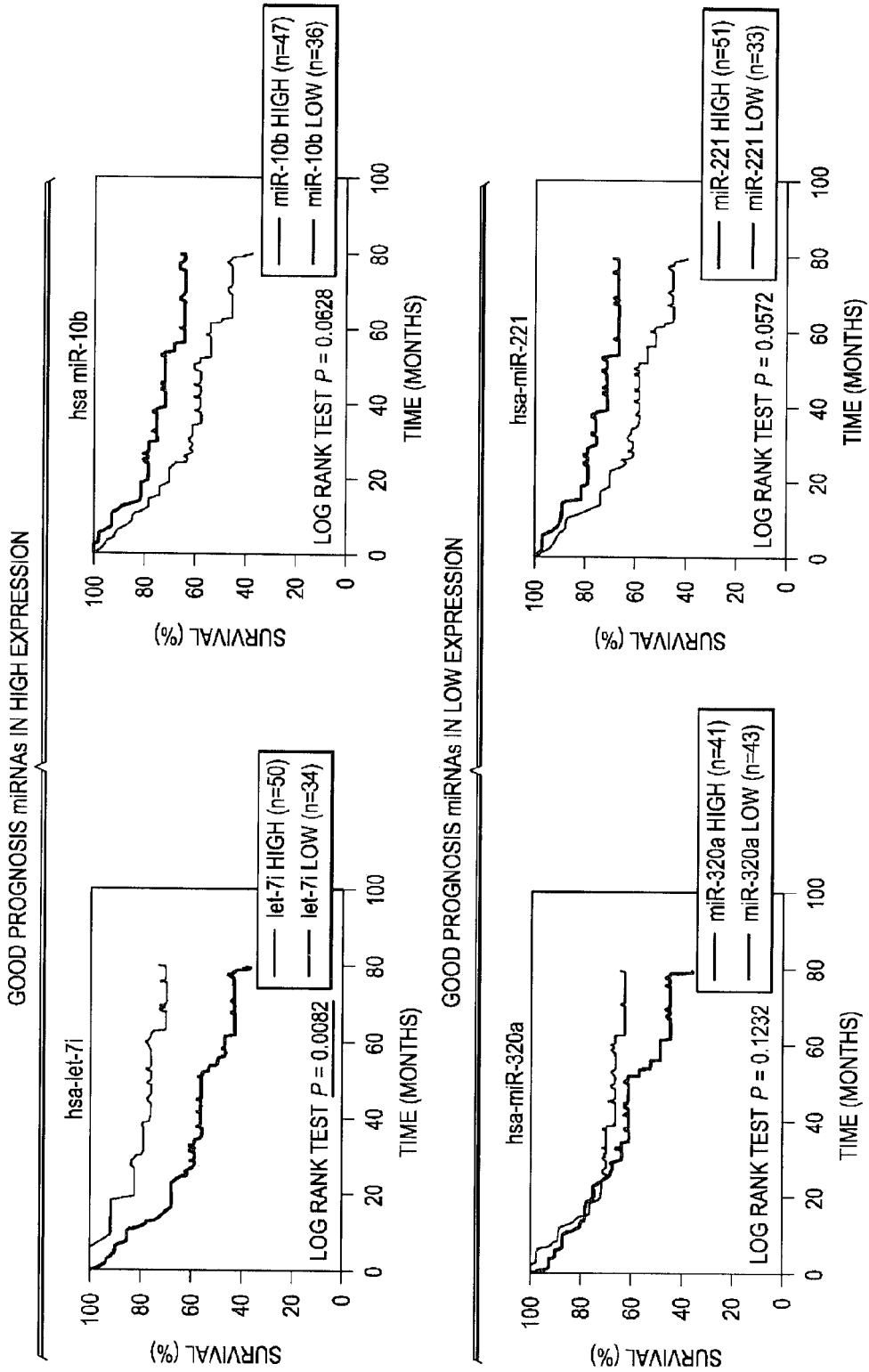
FIG. 4—shows the results from the microarray validation for selected miRNAs in 84 PCs.

FIG. 3 shows the Results—qRT-PCR validation for selected miRNAs in 58 PCs and LMs. FIG. 4 shows the results from the microarray validation for selected miRNAs in 84 PCs (Kaplan-Meier survival curves), in which high expression of has-let-7i and has-miR-320a indicated a good prognosis, which a low expression of has-miR-10b and has-miR-221 indicated a good prognosis.

These figures show that a miRNA signature can be used to distinguish between primary CRC and liver metastasis. It was found that a subset of miRNAs, including: let-7i, miR-10b, miR-30b, miR-200b, miR-320a, and miR-518d were significantly downregulated in liver metastasis tissues compared to primary CRC. In contrast, miRNAs such as miR-141, miR-200c, and miR-203 were significantly overexpressed in liver metastasis tissues. In a further evaluation step using serum samples from CRC patients, it was found that the serum expression levels of miR-200c and miR-203 were upregulated in CRC patients with distant metastasis compared to CRC patients without metastasis.

Next, additional studies were conducted to identify the specific subsets of miRNAs that may serve as diagnostic and therapeutic biomarkers for patients with metastatic CRC. A recent and accurate technology to identify novel metastasis related miRNA biomarkers (NANOSTRING®), plus additional studies were conducted to validate screened miRNA biomarkers using two different assay techniques in a large number of CRC tissues.

The screening step included the following materials: 9 pairs of primary CRC (PC) and matched liver metastasis (LM), Frozen tissue, Not-microdissected, method used: NANOSTRING®.

The validation step in matched PCs and LMs included the following materials: 58 pairs of PC and matched LM, formalin-fixed, paraffin-embedded (FFPE) tissue, Microdissected. The method for analysis was TaqMan miRNA assays, miR-16 was used as endogenous control.

A microarray validation step included the following materials: 84 pairs of PC and corresponding normal mucosa (NM), frozen tissue, not-microdissected. The method used was MicroRNA microarray (quadruplicates of 389 human miRNAs) as published in JAMA. 2008 Jan. 30; 299(4):425-36.

A qRT-PCR Validation step included the following materials: 175 PCs, FFPE tissue, microdissected. The method for analysis was TaqMan miRNA assays, with miR-16 used as endogenous control.

Table 1 is a summary of the clinicopathology characteristics of the colorectal cancer patients.

| Characteristics | NanoString cohort Patients n = 9 | matched PC and LM validation cohort Patients n = 58 | microarray validation cohort Patients n = 84 | qRT-PCR validation cohort Patients n = 175 |
|---|---|---|---|---|
| Clinicopathological characteristics of the colorectal cancer patients |||||
| Age (Years) |||||
| ≤65 | 6 | 34 | 38 | 74 |
| >65 | 3 | 24 | 46 | 101 |

| Clinicopathological characteristics of the colorectal cancer patients | | | | |
|---|---|---|---|---|
| Characteristics | NanoString cohort Patients n = 9 | matched PC and LM validation cohort Patients n = 58 | microarray validation cohort Patients n = 84 | qRT-PCR validation cohort Patients n = 175 |
| Sex | | | | |
| Male | 4 | 32 | 66 | 102 |
| Female | 5 | 26 | 18 | 73 |
| Adenocarcinoma histology | | | | |
| Adenocarcinoma* | — | 58 | 75 | 162 |
| Mucinous | — | 0 | 8 | 10 |
| Tumor location | | | | |
| Proximal | — | 12 | 34 | 58 |
| Distal | — | 18 | 48 | 49 |
| Rectum | — | 28 | | 68 |
| TNM stage | | | | |
| I | 0 | 0 | 8 | 38 |
| II | 0 | 7 | 29 | 53 |
| III | 0 | 17 | 36 | 44 |
| IV | 9 | 34 | 10 | 39 |

Table 2 shows the 10 miRNAs differentially expressed in matched PCs and LMs using the NANOSTRING® screening step.

| Probe from NanoString | Geometric mean | | Fold Change (LM/PC) | FDR (%) | P-value |
|---|---|---|---|---|---|
| | PC (n = 9) | LM (n = 9) | | | |
| hsa-miR-199b-5p | 360.77 | 70.81 | 0.2 | 0.01 | 6.E−05 |
| hsa-let-7i | 2154.94 | 1133.07 | 0.53 | 0.14 | 2.E−03 |
| hsa-miR-484 | 69.79 | 39.14 | 0.56 | 0.14 | 2.E−03 |
| hsa-miR-490-3p | 47.13 | 21.67 | 0.46 | 0.21 | 4.E−03 |
| hsa-miR-122 | 27.01 | 507.91 | 18.8 | 0.26 | 8.E−03 |
| hsa-miR-320a | 33.94 | 22.05 | 0.65 | 0.26 | 8.E−03 |
| hsa-miR-520e | 53.73 | 13.01 | 0.24 | 0.26 | 8.E−03 |
| hsa-miR-10b | 64.28 | 19.67 | 0.31 | 0.27 | 1.E−02 |
| hsa-miR-337-5p | 20.81 | 11.8 | 0.57 | 0.39 | 2.E−02 |
| hsa-miR-485-3p | 89.95 | 50.39 | 0.56 | 0.39 | 2.E−02 |
| hsa-miR-145 | 2915.38 | 1267.64 | 0.43 | 0.39 | 2.E−02 |
| hsa-miR-144 | 294.09 | 116.61 | 0.4 | 0.39 | 2.E−02 |
| hsa-miR-25 | 688.42 | 405.21 | 0.59 | 0.39 | 3.E−02 |
| hsa-miR-221 | 294.27 | 209.8 | 0.71 | 0.39 | 3.E−02 |
| hsa-miR-216a | 59.45 | 34.54 | 0.58 | 0.39 | 3.E−02 |
| hsa-miR-92b | 44.38 | 32.31 | 0.73 | 0.39 | 3.E−02 |
| hsa-miR-365 | 56.55 | 29.25 | 0.52 | 0.39 | 3.E−02 |
| hsa-miR-708 | 269.88 | 155.4 | 0.58 | 0.39 | 3.E−02 |
| hsa-miR-143 | 2652.88 | 1338.82 | 0.5 | 0.39 | 3.E−02 |

Table 3 shows the results from the microarray validation for 4 miRNAs in 84 PCs, briefly, it was found that The expression of let-7i, miR-10b and miR-320a m PC was significantly associated with the distant metastasis, while the expression of let-7i and miR-10b was significantly associated with the TNM stage.

| | hsa-let-7i | | | hsa-miR-10b | | | hsa-miR-221 | | | hsa-miR-320a | | |
|---|---|---|---|---|---|---|---|---|---|---|---|---|
| | n | mean ± SD | P value | n | mean ± SD | P value | n | mean ± SD | P value | n | mean ± SD | P value |
| Sex | | | 0.1502 | | | 0.3887 | | | 0.6947 | | | 0.173 |
| Male | 66 | 0.02407 ± 0.2635 | | 65 | −0.3092 ± 1.1328 | | 66 | 0.2713 ± 0.8388 | | 66 | 0.04704 ± 0.3012 | |
| Female | 18 | −0.06910 ± 0.2418 | | 18 | −0.4715 ± 0.9354 | | 18 | 0.3753 ± 0.6618 | | 18 | −0.1026 ± 0.3935 | |
| Age (Years) | | | 0.7279 | | | 0.7932 | | | 0.8397 | | | 0.8019 |
| ≤50 | 7 | −0.02879 ± 0.2321 | | 7 | −0.3526 ± 1.0560 | | 7 | 0.3691 ± 0.7193 | | 7 | 0.03658 ± 0.1627 | |
| >50 | 77 | 0.007094 ± 0.2641 | | 76 | −0.3436 ± 1.0995 | | 77 | 0.2867 ± 0.8126 | | 77 | 0.01302 ± 0.3380 | |
| T stage | | | 0.3125 | | | 0.1248 | | | 0.8359 | | | 0.3187 |
| T1/T2 | 12 | 0.07144 ± 0.2190 | | 12 | −0.8053 ± 1.0168 | | 12 | 0.3131 ± 0.7537 | | 12 | 0.09735 ± 0.2206 | |
| T3/T4 | 71 | −0.006089 ± 0.2682 | | 70 | −0.2755 ± 1.0942 | | 71 | 0.2900 ± 0.8200 | | 71 | 0.005285 ± 0.3409 | |
| N stage | | | 0.6085 | | | 0.1037 | | | 0.293 | | | 0.1925 |
| N0 | 38 | 0.03021 ± 0.2648 | | 38 | −0.5572 ± 1.2224 | | 38 | 0.1865 ± 0.7953 | | 38 | 0.06200 ± 0.2960 | |
| N1/N2/N3 | 46 | −0.01746 ± 0.2578 | | 45 | −0.1647 ± 0.9403 | | 46 | 0.3820 ± 0.8046 | | 46 | −0.02386 ± 0.3481 | |
| M stage | | | 0.0055 | | | 0.0243 | | | 0.0868 | | | 0.0498 |
| M0 | 74 | 0.03081 ± 0.2563 | | 73 | −0.4470 ± 1.0561 | | 74 | 0.2436 ± 0.7895 | | 74 | 0.03904 ± 0.3240 | |
| M1 | 10 | −0.1935 ± 0.2090 | | 10 | 0.4043 ± 1.0896 | | 10 | 0.6632 ± 0.8350 | | 10 | −0.1630 ± 0.3022 | |
| TNM stage | | | 0.0397 | | | 0.0498 | | | 0.3629 | | | 0.1623 |
| I | 8 | 0.08200 ± 0.2585 | | 8 | −1.0788 ± 1.1221 | | 8 | 0.1901 ± 0.8263 | | 8 | 0.1268 ± 0.2359 | |
| II | 29 | 0.02817 ± 0.2658 | | 29 | −0.4334 ± 1.2465 | | 29 | 0.1778 ± 0.8144 | | 29 | 0.06401 ± 0.2979 | |
| III | 36 | 0.02464 ± 0.2571 | | 35 | −0.3369 ± 0.8350 | | 36 | 0.3065 ± 0.7903 | | 36 | 0.008416 ± 0.3614 | |
| IV | 10 | −0.1935 ± 0.2090 | | 10 | 0.4043 ± 1.0896 | | 10 | 0.6632 ± 0.8350 | | 10 | −0.1630 ± 0.3022 | |

Table 4 shows the results of microarray validation for 4 miRNAs in 84 PCs, using a Cox proportional hazards model. It was found that low expression of let-7i was an independent prognostic factor.

| Variables | Univariate | | |
|---|---|---|---|
| | HR | 95% CI | P |
| Good prognosis mRNAs in high expression | | | |
| Age (>50 vs. ≤50) | 0.7523 | 0.2291 to 2.4704 | 0.6528 |
| Sex (Male vs. Female) | 1.3423 | 0.5605 to 3.2147 | 0.4974 |
| T stage (T3/4 vs. T1/2) | 2.278 | 0.7021 to 7.3914 | 0.1262 |
| N stage (N1/2/3 vs. N0) | 2.9984 | 1.4477 to 6.2100 | 0.0018 |
| M stage (M1 vs. M0) | 8.4586 | 3.6184 to 19.7731 | 0.0001 |
| hsa-let-7i (Low vs. High) | 2.6706 | 1.2577 to 5.6710 | 0.0066 |
| hsa-miR-320a (Low vs. High) | 1.6783 | 0.8655 to 3.2545 | 0.1239 |
| Good prognosis mRNAs in low expression | | | |
| Age (>50 vs. ≤50) | 0.7523 | 0.2291 to 2.4704 | 0.6528 |
| Sex (Male vs. Female) | 1.3423 | 0.5605 to 3.2147 | 0.4974 |
| T stage (T3/4 vs. T1/2) | 2.278 | 0.7021 to 7.3914 | 0.1262 |
| N stage (N1/2/3 vs. N0) | 2.9984 | 1.4477 to 6.2100 | 0.0018 |
| M stage (M1 vs. M0) | 8.4586 | 3.6184 to 19.7731 | <0.0001 |
| hsa-miR-10b (High vs. Low) | 1.9156 | 0.9581 to 3.8300 | 0.0599 |
| hsa-miR-221 (High vs. Low) | 2.0042 | 0.9687 to 4.1466 | 0.0515 |

HR, hazard ratio;
CI, confidence interval

Table 5 shows the results of microarray validation for 4 miRNAs in 84 PCs, using a logistic regression model. It was found that all 4 miRNAs (let-7i, miR-320a, miR-10b and miR-221) expression in PCs was significantly associated with the distant metastasis. It was also found that low expression of let-7i and high expression of miR-10b in PCs were an independent metastasis prediction marker, respectively.

| Variables | Univariate | | |
|---|---|---|---|
| | OR | 95% CI | P |
| Good prognosis mRNAs in high expression | | | |
| Age (>50 vs. ≤50) | 0.7941 | 0.0855 to 7.3728 | 0.8428 |
| Sex (Male vs. Female) | 1.1034 | 0.2129 to 5.7192 | 0.906 |
| T stage (T3/4 vs. T1/2) | 2.05E+07 | 0.0000 to 0.0000 | 0.0673 |
| N stage (N1/2/3 vs. N0) | 9 | 1.0850 to 74.6570 | 0.0102 |
| hsa-let-7i (Low vs. High) | 19.25 | 4.1320 to 89.6808 | 0.0001 |
| hsa-miR-320a (Low vs. High) | 5.5152 | 1.3048 to 23.3120 | 0.0144 |
| Good prognosis mRNAs in low expression | | | |
| Age (>50 vs. ≤50) | 0.7941 | 0.0855 to 7.3728 | 0.8428 |
| Sex (Male vs. Female) | 1.1034 | 0.2129 to 5.7192 | 0.906 |
| T stage (T3/4 vs. T1/2) | 205E+07 | 0.0000 to 0.0000 | 0.0673 |
| N stage (N1/2/3 vs. N0) | 9 | 1.0850 to 74.6570 | 0.0102 |
| hsa-miR-10b (High vs. Low) | 7.625 | 1.8645 to 31.1838 | 0.0044 |
| hsa-miR-221 (High vs. Low) | 9 | 1.0850 to 74.6570 | 0.0102 |

OR, odds ratio;
CI, confidence interval

Figure 5:
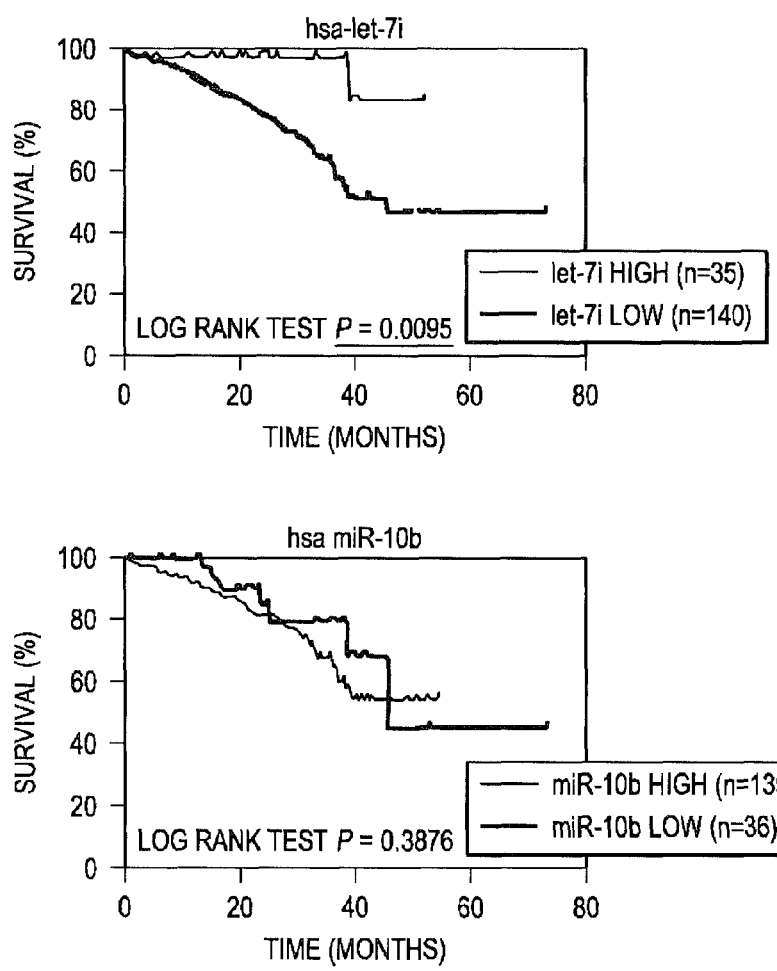
FIG. 5—shows the results of qRT-PCR validation for miR-7i (left graph) and miR-10b (right graph) in 175 PCs.

FIG. 5 shows the results of qRT-PCR validation for miR-7i and miR-10b in 175 PCs. Survival analysis of 2 microarray validated miRNAs is shown.

Table 6 shows the results of qRT-PCR validation for miR-7i and miR-10b in 175 PCs. It was found that the expression of let-7i, miR-10b and miR-320a in PC was significantly associated with the distant metastasis (using the Kreskal-Wallis test). The expression of let-7i and miR-10b was significantly associated with the TNM stage.

| | hsa-let-7i | | | hsa-miR-10b | | |
|---|---|---|---|---|---|---|
| | n | mean ± SD | P value | n | mean ± SD | P value |
| Sex | | | 0.9441 | | | 0.1311 |
| Male | 78 | 0.7862 ± 0.2881 | | 78 | 0.05870 ± 0.02865 | |
| Female | 60 | 0.7956 ± 0.2960 | | 60 | 0.05391 ± 0.03159 | |
| Age (Years) | | | 0.6466 | | | 0.5857 |
| ≤Median | 68 | 0.7938 ± 0.2804 | | 68 | 0.05588 ± 0.03143 | |
| >Median | 70 | 0.7875 ± 0.3012 | | 70 | 0.05734 ± 0.02864 | |
| T stage | | | 0.6927 | | | 0.0183 |
| T1/T2 | 47 | 0.7441 ± 0.1990 | | 47 | 0.04823 ± 0.02788 | |
| T3/T4 | 90 | 0.8081 ± 0.3183 | | 90 | 0.06036 ± 0.02983 | |
| N stage | | | 0.0407 | | | 0.6505 |
| N0 | 85 | 0.8375 ± 0.3025 | | 85 | 0.05571 ± 0.03017 | |
| N1/N2/N3 | 53 | 0.7235 ± 0.2608 | | 53 | 0.05808 ± 0.02981 | |
| M stage | | | <0.0001 | | | 0.0486 |
| M0 | 114 | 0.8517 ± 0.3013 | | 114 | 0.05443 ± 0.02938 | |
| M1 | 24 | 0.6133 ± 0.1562 | | 24 | 0.06701 ± 0.03105 | |
| TNM stage | | | 0.0002 | | | 0.0208 |
| I | 38 | 0.7513 ± 0.2090 | | 38 | 0.04884 ± 0.03021 | |
| II | 43 | 0.8889 ± 0.3261 | | 43 | 0.06255 ± 0.03029 | |
| III | 33 | 0.8896 ± 0.3245 | | 33 | 0.05029 ± 0.02540 | |
| IV | 24 | 0.6133 ± 0.1562 | | 24 | 0.06701 ± 0.03105 | |

Table 7 shows the results from qRT-PCR validation for miR-7i and miR-10b in 175 PCs using the Cox proportional hazards model. It was found that Low expression of let-7i was significantly associated with CRC patient's prognosis, which was an independent prognostic factor.

| Variables | Univariate | | |
|---|---|---|---|
| | HR | 95% CI | P |
| Good prognosis mRNAs in high expression | | | |
| Age (>Median vs. ≤Median) | 0.8034 | 0.4370 to 1.4772 | 0.4816 |
| Sex (Male vs. Female) | 1.1504 | 0.6133 to 2.1576 | 0.662 |
| T stage (T3/4 vs. T1/2) | 7.9376 | 1.9318 to 32.6160 | 0.0001 |
| Lymph node metastasis (Yes vs. No) | 15.179 | 5.4217 to 42.4966 | <0.0001 |
| Liver metastasis (Yes vs. No) | 12.0601 | 6.0761 to 23.9370 | <0.0001 |
| Pathology (Poor diff. vs. Well/Mod diff.) | 1.8409 | 0.7747 to 4.3745 | 0.2005 |
| CEA (>Median vs. ≤Median) | 5.4597 | 2.2795 to 13.0769 | <0.0001 |
| hsa-let-7i (Low vs. High) | 5.3525 | 1.3009 to 22.0225 | 0.0026 |
| Good prognosis mRNAs in low expression | | | |
| Age (>Median vs. ≤Median) | 0.8034 | 0.4370 to 1.4772 | 0.4816 |
| Sex (Male vs. Female) | 1.1504 | 0.6133 to 2.1576 | 0.662 |
| T stage (T3/4 vs. T1/2) | 7.9376 | 1.9318 to 32.6160 | 0.0001 |
| Lymph node metastasis (Yes vs. No) | 15.179 | 5.4217 to 42.4966 | <0.0001 |
| Liver metastasis (Yes vs. No) | 12.0601 | 6.0761 to 23.9370 | <0.0001 |
| Pathology (Poor diff. vs. Well/Mod diff.) | 1.8409 | 0.7747 to 4.3745 | 0.2005 |
| CEA (>Median vs. ≤Median) | 5.4597 | 2.2795 to 13.0769 | <0.0001 |
| hsa-miR-10b (High vs. Low) | 1.7849 | 0.7283 to 4.3747 | 0.1946 |

HR, hazard ratio;
CI, confidence interval

Table 8 shows the results from qRT-PCR validation for miR-7i and miR-10b in 175 PCs using a logistic regression model. It was found that expression of let-7i and miR-10b in PCs was significantly associated with the distant metastasis. Low expression of let-7i and high expression of miR-10b in PCs were an independent metastasis prediction marker, respectively.

| Variables | Univariate | | |
|---|---|---|---|
| | OR | 95% CI | P |
| Good prognosis mRNAs in high expression | | | |
| Age (>Median vs. ≤Median) | 0.5152 | 0.2486 to 1.0677 | 0.0711 |
| Sex (Male vs. Female) | 1.0505 | 0.5094 to 2.1662 | 0.8938 |
| T stage (T3/4 vs. T1/2) | 6.07E+00 | 1.7714 to 20.7823 | 0.0005 |
| N stage (N1/2/3 vs. N0) | 25.6744 | 7.4879 to 88.0324 | 0.0001 |
| hsa-let-7i (Low vs. High) | 5.9853 | 1.3679 to 26.1892 | 0.0031 |
| Good prognosis mRNAs in low expression | | | |
| Age (>Median vs. ≤Median) | 0.5152 | 0.2486 to 1.0677 | 0.0711 |
| Sex (Male vs. Female) | 1.0505 | 0.5094 to 2.1662 | 0.8938 |
| T stage (T3/4 vs. T1/2) | 6.07E+00 | 1.7714 to 20.7823 | 0.0005 |
| N stage (N1/2/3 vs. N0) | 25.6744 | 7.4879 to 88.0324 | <0.0001 |
| hsa-miR-10b (High vs. Low) | 2.8624 | 0.8176 to 10.0217 | 0.05 |

OR, odds ratio;
CI, confidence interval

Figure 6:
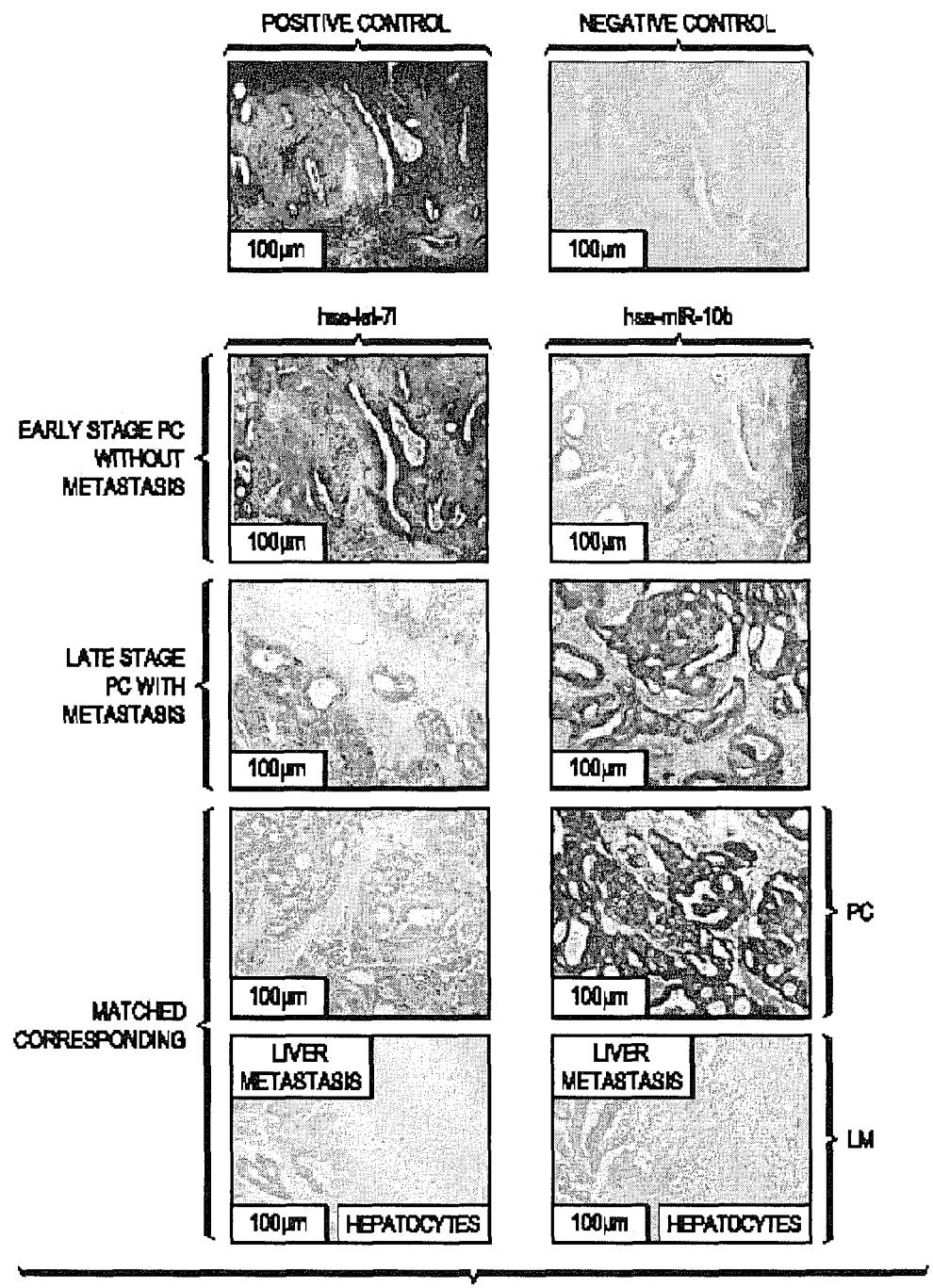
FIG. 6—shows the ISH validation for the expression of miR-7i and miR-10b in CRC tissues and liver metastasis.

FIG. 6 shows the ISH validation for the expression of miR-7i and miR-10b in CRC tissues and liver metastasis.

As such, it was found that 19 metastasis specific miRNAs were identified through screening step using NANOSTRING® analysis. Among 19 screened miRNAs, 4 miRNAs were validated in a large number of matched PC and LM tissues (58 pairs). High expression of let-7i was significantly associated with better survival, which was an independent prognostic marker in CRC patients. Low expression of let-7i and high expression of miR-10b were independent metastasis prediction markers in PCs, respectively. Finally, it was found that let-7i and miR-10b expression was successfully validated through ISH analysis in CRC tissues.

It is contemplated that any embodiment discussed in this specification can be implemented with respect to any method, kit, reagent, or composition of the invention, and vice versa. Furthermore, compositions of the invention can be used to achieve methods of the invention.

Example 2—Identification of a Metastasis-Specific miRNA Signature in Human Colorectal Cancer A metastasis-specific miRNA biomarker discovery approach was developed that involved comprehensive miRNA expression profiling of both primary CRC (pCRC) and matched liver metastasis (LM) tissues, followed by validation of these newly discovered miRNA biomarkers in multiple, large, independent cohorts of tissues. The expression patterns of these miRNAs was correlated with important clinicopathological parameters related to CRC metastasis. The feasibility of these miRNAs as tissue-based and serum-based metastasis-specific biomarkers was also evaluated.

Methods

Patient Samples.

This study utilized 477 tissue specimens including 326 pCRCs, 67 matched corresponding LMs, and 84 adjacent non-tumor colonic tissues from 5 different CRC patient cohorts that are described in Table 9. In addition, 169 serum samples from CRC patients were also analyzed

TABLE 9

| Characteristics of All Patients from each CRC Cohort | | | | | |
|---|---|---|---|---|---|
| Characteristics | NanoString cohort Patients n = 9 | NanoString validation cohort Patients n = 58 | Microarray cohort Patients n = 84 | Microarray validation cohort Patients n = 175 | Serum cohort Patients n = 169 |
| Age (years) | | | | | |
| ≤65 | 6 | 34 | 38 | 74 | 69 |
| >65 | 3 | 24 | 46 | 101 | 100 |
| Sex | | | | | |
| Male | 4 | 32 | 66 | 102 | 96 |
| Female | 5 | 26 | 18 | 73 | 73 |

TABLE 9-continued

Characteristics of All Patients from each CRC Cohort

| Characteristics | NanoString cohort Patients n = 9 | NanoString validation cohort Patients n = 58 | Microarray cohort Patients n = 84 | Microarray validation cohort Patients n = 175 | Serum cohort Patients n = 169 |
|---|---|---|---|---|---|
| Adenocarcinoma histology | | | | | |
| Adenocarcinoma* | — | 58 | 75 | 162 | 152 |
| Mucinous | — | 0 | 8 | 10 | 10 |
| Tumor location | | | | | |
| Proximal | — | 12 | 34 | 58 | 54 |
| Distal | — | 18 | 48 | 49 | 44 |
| Rectum | — | 28 | | 68 | 71 |
| TNM stage | | | | | |
| I | 0 | 0 | 8 | 38 | 37 |
| II | 0 | 7 | 29 | 53 | 58 |
| III | 0 | 17 | 36 | 44 | 42 |
| IV | 9 | 34 | 10 | 40 | 30 |

*Adenocarcinoma includes well, moderately, and poorly differentiated.

For the NanoString screening analysis, 9 pairs of frozen pCRC tissues and LM tissues were used. For validation, 58 pairs of formalin-fixed, paraffin-embedded (FFPE) pCRC tissues and matched corresponding LM tissues from Okayama University and Toho University, Japan were used.

For miRNA microarray analysis, 84 pairs of frozen pCRC and adjacent non-tumor tissues were obtained from the University of Maryland Medical Center or Baltimore Veterans Affairs Medical Center, as described previously (Schetter 2008). The validation cohort for this analysis included 175 FFPE pCRC tissues from Mie University Medical Hospital, Japan.

For miRNA analysis in blood, 169 serum samples from CRC patients enrolled at the Mie University Medical Hospital, Japan were also included. The CEA expression levels in 169 serum samples were measured by standard enzyme immunoassay.

Both tissue- and serum-based studies were approved by the Institutional Review Boards (IRB) of all involved institutions, and written informed consent was obtained from all patients.

Nanostring Assay and miRNA Microarray Analysis.

100 ng of total RNA from frozen tissues were analyzed using NanoString human miRNA v1 assays (NanoString Technologies, Seattle, USA) according to the manufacturer's instructions (NCBIGEO GSE44121). After background subtraction, data was normalized to the geometric mean of the top 75 miRNAs. Paired Student's t-test was used to calculate statistical significance. The miRNA microarray expression data (NCBIGEO GSE7828) (Schetter 2008) were analyzed for miRNA expression in primary tumors that were associated with distant metastases.

MiRNA Isolation and Quantitative Real-Time Polymerase Chain Reaction (qRT-PCR).

Total RNA (including miRNA) was extracted from FFPE specimens using the Total Nucleic Acid Isolation Kit for FFPE tissues (Ambion, Austin, Tex., USA). RNA was extracted from frozen tissue specimens using standard Trizol protocols (Invitrogen). Expression of let-7i, miR-10b, miR-30b, miR-221, miR-320a, and miR-885-5p were analyzed using TaqMan miRNA assays (Applied Biosystems, Foster City, Calif.), and miR-16 expression was used as an endogenous control for data normalization, as previously described (Hur 2012).

Small RNAs were isolated from 250 >μL serum samples from CRC patients using the Qiagen miRNAeasy Kit (Qiagen, Valencia, Calif.). For normalization of sample-to-sample variation during RNA isolation, 25 fmol of synthetic C. elegans miRNA (cel-miR-39, Applied Biosystems) was added to each serum sample. Expression of miR-885-5p was analyzed using TaqMan miRNA assays (Applied Biosystems) as described previously (Hur 2012).

The average expression levels of serum and tissue miRNAs were normalized against cel-miR-39 and miR-16 using the $2^{-\Delta Ct}$ method. Differences between groups were presented as ΔCt, which indicate the difference between Ct values of the miRNA of interest and the Ct value of the normalizer miRNA.

In Situ Hybridization (ISH) Analysis.

Five micrometer thick FFPE tissue sections were hybridized with the let-7i, miR-10b, and miR-885-5p probes (LNA-modified and 5'- and 3'-DIG-labeled oligonucleotide, Exiqon, Woburn, Mass., USA), respectively, as described previously (Hur 2012). Positive controls (U6 snRNA, LNA-modified and 5'- and 3'-DIG-labeled oligonucleotide, Exiqon) and negative controls (scrambled miRNA control, LNA-modified and 5'- and 3'-DIG-labeled oligonucleotide, Exiqon) were included in each hybridization procedure as previously described (Hur 2010).

Statistical Analysis:

Paired t-test, Mann-Whitney test, and $\chi 2$ tests were used to analyze microRNA expression. Kaplan-Meier analysis and the log-rank test were used for survival analysis. The miRNA expression values from the miRNA microarray cohmi, miRNA microarray validation cohort, and serum cohort were dichotomized into high- and low-expression based on receiver operating characteristic (ROC) curves established for predicting distant metastasis. Univariate and multivariate Cox's propmiional hazards models were used to identify independent prognostic factors dictating patient survival. Univariate and multivariate logistic regression models identified independent predictive factors for distant metastasis and lymph node (LN) metastasis. Data are presented as mean±S.D. (standard deviation) and all statistical analyses were conducted using the Medcalc version 12.3 (Broekstraat, Belgium) and the GraphPad Prism version 5.0 (GraphPad Software, San Diego, Calif.).

Results

Profiling and validation of CRC metastasis-specific miRNAs in paired pCRC and LM tissues. To discover miRNAs that are involved in CRC metastasis, NanoString-based miRNA expression profiling was performed in 9 pairs of matched pCRC and LM frozen tissues (Table 10). Twenty three miRNAs were found to be differentially expressed between pCRC and matched LM tissues (p<0.001). All but 3 miRNAs (miR-122, miR-30b, and miR-885-5p) were down-regulated in LM. Since miR-122 is a conserved liver-specific miRNA and is required for normal hepatic biology and function (Chang 2004), this miRNA was excluded from further analysis.

TABLE 10

Differentially Expressed CRC Metastasis-Specific microRNAs between Matched Primary CRC (pCRC) and Liver metastasis (LM) in NanoString Analysis

| Probe from NanoString | Geometric mean pCRC (n = 9) | Geometric mean LM (n = 9) | Fold Change LM/pCRC | FDR | P-value |
|---|---|---|---|---|---|
| hsa-miR-199b-5p | 360.77 | 70.81 | 0.2 | 0.01 | 6.E-05 |
| hsa-let-7i | 2154.94 | 1133.07 | 0.53 | 0.14 | 2.E-03 |
| hsa-miR-484 | 69.79 | 39.14 | 0.56 | 0.14 | 2.E-03 |
| hsa-miR-490-3p | 47.13 | 21.67 | 0.46 | 0.21 | 4.E-03 |
| hsa-miR-122 | 27.01 | 507.91 | 18.8 | 0.26 | 8.E-03 |
| hsa-miR-320a | 33.94 | 22.05 | 0.65 | 0.26 | 8.E-03 |
| hsa-miR-520e | 53.73 | 13.01 | 0.24 | 0.26 | 8.E-03 |
| hsa-miR-10b | 64.28 | 19.67 | 0.31 | 0.27 | 1.E-02 |
| hsa-miR-337-5p | 20.81 | 11.8 | 0.57 | 0.39 | 2.E-02 |
| hsa-miR-485-3p | 89.95 | 50.39 | 0.56 | 0.39 | 2.E-02 |
| hsa-miR-145 | 2915.38 | 1267.64 | 0.43 | 0.39 | 2.E-02 |
| hsa-miR-144 | 294.09 | 116.61 | 0.4 | 0.39 | 2.E-02 |
| hsa-miR-25 | 688.42 | 405.21 | 0.59 | 0.39 | 3.E-02 |
| hsa-miR-221 | 294.27 | 209.8 | 0.71 | 0.39 | 3.E-02 |
| hsa-miR-216a | 59.45 | 34.54 | 0.58 | 0.39 | 3.E-02 |
| hsa-miR-92b | 44.38 | 32.31 | 0.73 | 0.39 | 3.E-02 |
| hsa-miR-365 | 56.55 | 29.25 | 0.52 | 0.39 | 3.E-02 |
| hsa-miR-708 | 269.88 | 155.4 | 0.58 | 0.39 | 3.E-02 |
| hsa-miR-143 | 2652.88 | 1338.82 | 0.5 | 0.39 | 3.E-02 |
| has-miR-196a | 112.84 | 45.6 | 0.4 | 0.42 | 4.E-02 |
| has-miR-451 | 2174.72 | 623.91 | 0.29 | 0.46 | 4.E-02 |
| has-miR-30b | 1092.95 | 1864.19 | 1.71 | 0.46 | 5.E-02 |
| has-miR-885-5p | 24.46 | 64.95 | 2.65 | 0.46 | 5.E-02 |

FDR, False discovery rate

Figure 7:
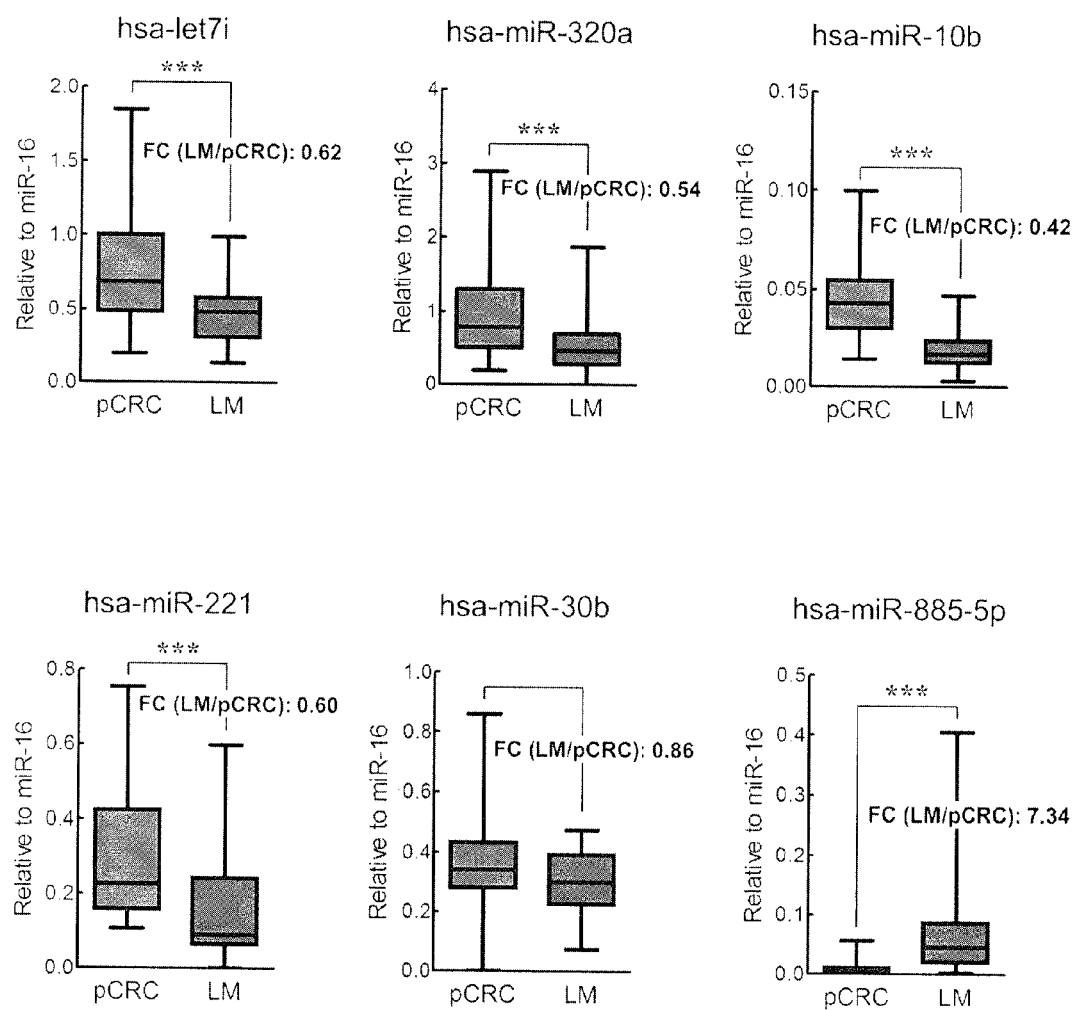
FIG. 7—Expression status of candidate miRNAs as CRC metastasis-specific biomarkers. Among the unique subset of 23 newly identified CRC metastasis-specific miRNAs, 4 were down-regulated (let-7i, miR-320a, miR-10b and miR-221) and 2 were up-regulated (miR-30b and miR-885-5p) in liver metastasis (LM) compared to primary CRC (pCRC) in an independent validation cohort of 59 pairs of matching pCRC and LM tissues. ***p<0.0001, paired t-test.
Figure 12:
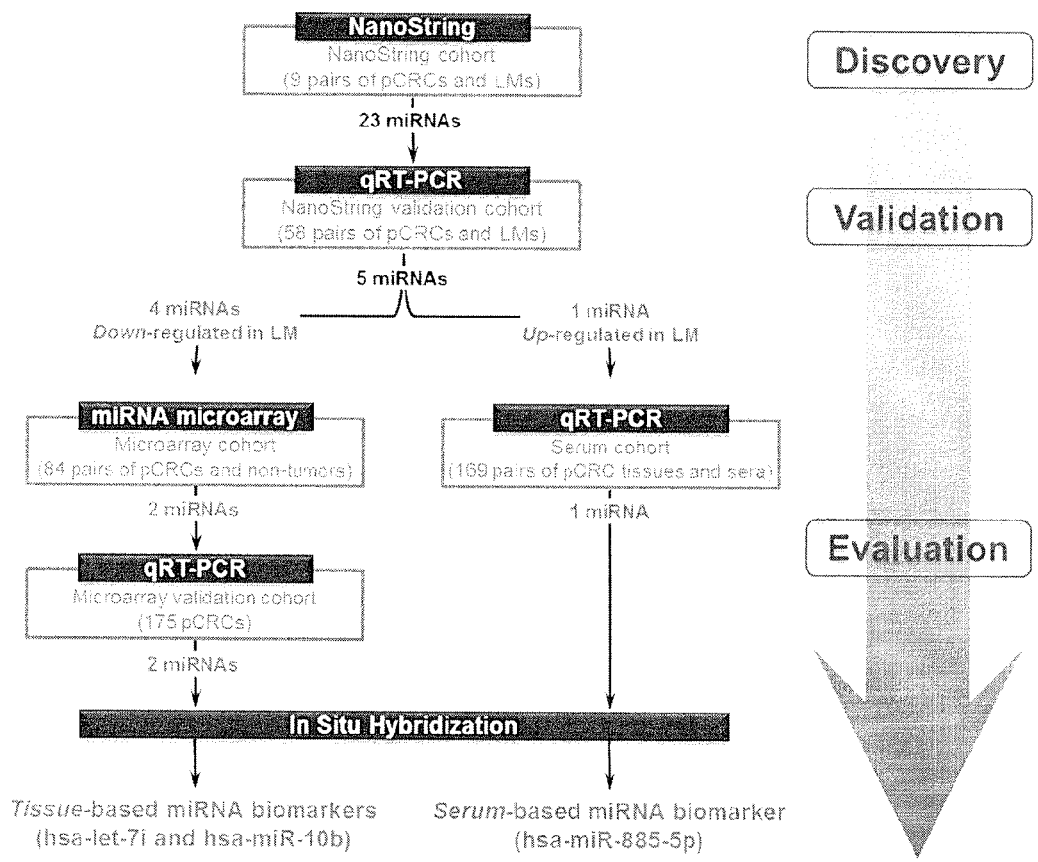
FIG. 12—Study Process Flow Chart

Four miRNAs down-regulated in LM compared to pCRC (let-7i, miR-320a, miR-10b, and miR-221) and 2 up-regulated miRNAs (miR-30b and miR-885-5p) were selected for validation by qRT-PCR in an independent cohort of 59 matched pCRC and LM tissues (FIG. 7). All but one miRNA was validated, including all of the down-regulated miRNAs (let-7i, 0.62 fold; miR-320a, 0.54 fold; miR-10b, 0.42 fold; miR-221, 0.6 fold) and one of the up-regulated miRNAs miR-885-5p (7.34 fold) in LMs compared to pCRCs. These data suggest that the specific miRNA expression patterns can distinguish between primary CRC cells and cancer cells metastatic to liver.

Expression Patterns of Metastasis-Specific miRNAs in Primary CRC Tissues.

To investigate the clinical relevance of metastasis-specific miRNAs in CRC development, it was determined whether these miRNAs were altered in the primary tumors that had given rise to later metastasis compared to pCRCs that did not. Previous miRNA microarray data were validated on 84 pairs of frozen tumor and adjacent non-tumor tissues (Schetter 2008). miRNA expression in pCRCs was normalized to paired nontumor tissue by subtracting the log 2 nontumor from the $\log_2$ tumor expression for let-7i, miR-320a, miR-19b, and miR-221. MiR-885-5p expression data was not available. Let-7i (P=0.0055) and miR-320a (P=0.0498) were significantly reduced, and miR-10b was significantly increased (P=0.0498) in the pCRCs of patients who suffered later distant metastases compared to pCRCs of patients who did not develop metastases (Table 11). MiR-221 was non-significantly increased (P=0.0868) in pCRCs of patients with distant metastases (eTable 3). Based on these data, the miRNAs were classified as tumor suppressor (let-7i and miR-320a) or oncogenic (miR-10b, miR-221) miRNAs. In addition, decreased let-7i expression (P=0.0397) and increased miR-10b expression (P=0.0498) were significantly associated with more advanced TNM stage in pCRC tissues (Table 11).

TABLE 11

Clinical Relevance of 4 miRNAs (let-7i, miR-10b, miR-221, and miR-320a) in miRNA Microarray Cohort (Kruskal-Wallis Test)

| | hsa-let-7i | | | hsa-miR-10b | | | hsa-miR-221 | | | hsa-miR-320a | | |
|---|---|---|---|---|---|---|---|---|---|---|---|---|
| | n | mean ± SD | P value | n | mean ± SD | P value | n | mean ± SD | P value | n | mean ± SD | P value |
| Sex | | | 0.1502 | | | 0.3887 | | | 0.6947 | | | 0.173 |
| Male | 66 | 0.02407 ± 0.2635 | | 65 | -0.3092 ± 1.1328 | | 66 | 0.2713 ± 0.8388 | | 66 | 0.04704 ± 0.3012 | |
| Female | 18 | -0.06910 ± 0.2418 | | 18 | -0.4715 ± 0.9354 | | 18 | 0.3753 ± 0.6618 | | 18 | -0.1026 ± 0.3935 | |
| Age (Years) | | | 0.7279 | | | 0.7932 | | | 0.8397 | | | 0.8019 |
| ≤50 | 7 | -0.02879 ± 0.2321 | | 7 | -0.3526 ± 1.0560 | | 7 | 0.3691 ± 0.7193 | | 7 | 0.3658 ± 0.1627 | |
| >50 | 77 | 0.007094 ± 0.2641 | | 76 | -0.3436 ± 1.0995 | | 77 | 0.2867 ± 0.8126 | | 77 | 0.01302 ± 0.3380 | |
| T stage | | | 0.3125 | | | 0.1248 | | | 0.8359 | | | 0.3187 |
| T1/T2 | 12 | 0.07144 ± 0.2190 | | 12 | -0.8053 ± 1.0168 | | 12 | 0.3131 ± 0.7537 | | 12 | 0.09735 ± 0.2206 | |
| T3/T4 | 71 | -0.006089 ± 0.2682 | | 70 | -0.2755 ± 1.0942 | | 71 | 0.2900 ± 0.8200 | | 71 | 0.005285 ± 0.3409 | |
| N stage | | | 0.6085 | | | 0.1037 | | | 0.293 | | | 0.1925 |
| N0 | 38 | 0.03021 ± 0.2648 | | 38 | -0.5572 ± 1.2224 | | 38 | 0.1865 ± 0.7953 | | 38 | 0.06200 ± 0.2960 | |

TABLE 11-continued

Clinical Relevance of 4 miRNAs (let-7i, miR-10b, miR-221, and miR-320a) in miRNA Microarray Cohort (Kruskal-Wallis Test)

| | hsa-let-7i | | | hsa-miR-10b | | | hsa-miR-221 | | | hsa-miR-320a | | |
|---|---|---|---|---|---|---|---|---|---|---|---|---|
| | n | mean ± SD | P value | n | mean ± SD | P value | n | mean ± SD | P value | n | mean ± SD | P value |
| N1/N2/N3 | 46 | −0.01746 ± 0.2578 | | 45 | −0.1647 ± 0.9403 | | 46 | 0.3820 ± 0.8046 | | 46 | −0.02386 ± 0.3481 | |
| M stage | | | 0.0055 | | | 0.0243 | | | 0.0868 | | | 0.0498 |
| M0 | 74 | 0.03081 ± 0.2563 | | 73 | −0.4470 ± 1.0561 | | 74 | 0.2436 ± 0.7895 | | 74 | 0.03904 ± 0.3240 | |
| M1 | 10 | −0.1935 ± 0.2090 | | 10 | 0.4043 ± 1.0896 | | 10 | 0.6632 ± 0.8350 | | 10 | −0.1630 ± 0.3022 | |
| TNM stage | | | 0.0397 | | | 0.0498 | | | 0.3629 | | | 0.1623 |
| I | 8 | 0.08200 ± 0.2585 | | 8 | −1.0788 ± 1.1221 | | 8 | 0.1901 ± 0.8263 | | 8 | 0.1268 ± 0.2359 | |
| II | 29 | 0.02817 ± 0.2658 | | 29 | −0.4334 ± 1.2465 | | 29 | 0.1778 ± 0.8144 | | 29 | 0.06401 ± 0.2979 | |
| III | 36 | 0.02464 ± 0.2571 | | 35 | −0.3369 ± 0.8350 | | 36 | 0.3065 ± 0.7903 | | 36 | 0.008416 ± 0.3614 | |
| IV | 10 | 0.1935 ± 0.2090 | | 10 | 0.4043 ± 1.0896 | | 10 | 0.6632 ± 0.8350 | | 10 | −0.1630 ± 0.3022 | |

Logistic regression was used to examine the potential of these miRNAs to predict metastases (Table 12). In univariate models, low let-7i expression (OR, 19.3; 95% CI, 4.1 to 89.7; P=0.0001), low miR-320a expression (OR, 5.5; 95% CI, 1.3 to 23.3; P=0.0144), high miR-10b expression (OR, 7.6; 95% CI, 1.9 to 31.2; P=0.0044), and high miR-221 expression (OR, 9.0; 95% CI, 1.1 to 74.7; P=0.0102) significantly associated with distant metastasis from CRC. Multivariate logistic regression models revealed that low let-7i expression (OR, 21.7; 95% CI, 2.9 to 163.4; P=0.0028) and high miR-10b expression (OR, 7.2; 95% CI, 1.2 to 44.1; P=0.0328) were associated with CRC distant metastasis independent of other clinical covariates

TABLE 12

Univariate and Multivariate analysis for Prognosis in CRC in the miRNA Microarray Cohort Association between miRNA expression and CRC prognosis (Cox proportional hazards model)

| | Univariate | | | Multivariate | | |
|---|---|---|---|---|---|---|
| Characteristics | HR | 95% CI | P | HR | 95% CI | P |
| Tumor Suppressor-miRNAs | | | | | | |
| Age (>50 vs. ≤50) | 0.7523 | 0.2291 to 2.4704 | 0.6528 | 0.6902 | 0.1957 to 2.4340 | 0.5662 |
| Sex (Male vs. Female) | 1.3423 | 0.5605 to 3.2147 | 0.4974 | 1.6101 | 0.6343 to 4.0870 | 0.3187 |
| T stage (T3/4 vs. T1/2) | 2.278 | 0.7021 to 7.3914 | 0.1262 | 1.7466 | 0.5217 to 5.8481 | 0.3682 |
| N stage (N1/2/3 vs. N0) | 2.9984 | 1.4477 to 6.2100 | 0.0018 | 2.5046 | 1.1697 to 5.3628 | 0.0187 |
| M stage (M1 vs. M0) | 8.4586 | 3.6184 to 19.7731 | <0.0001 | 4.5868 | 1.8137 to 11.6000 | 0.0014 |
| hsa-let-7i (Low vs. High) | 2.6706 | 1.2577 to 5.6710 | 0.0066 | 2.2797 | 1.0147 to 5.1218 | 0.0471 |
| hsa miR-320a (Low vs. High) | 1.6783 | 0.8655 to 3.2545 | 0.1239 | 1.0312 | 0.5069 to 2.0980 | 0.9327 |
| Oncogenic-miRNAs | | | | | | |
| Age (>50 vs. ≤50) | 0.7523 | 0.2291 to 2.4704 | 0.6528 | 0.674 | 0.1935 to 2.3483 | 0.5377 |
| Sex (Male vs. Female) | 1.3423 | 0.5605 to 3.2147 | 0.4974 | 1.7547 | 0.6982 to 4.4100 | 0.2341 |
| T stage (T3/4 vs. T1/2) | 2.278 | 0.7021 to 7.3914 | 0.1262 | 1.9205 | 0.5675 to 6.4999 | 0.2966 |
| N stage (N1/2/3 vs. N0) | 2.9984 | 1.4477 to 6.2100 | 0.0018 | 2.4331 | 1.1368 to 5.2078 | 0.0227 |
| M stage (M1 vs. M0) | 8.4586 | 3.6184 to 19.7731 | <0.0001 | 4.7717 | 1.8904 to 12.0445 | 0.001 |
| hsa-miR-10b (Low vs. High) | 1.9156 | 0.9581 to 3.8300 | 0.0599 | 1.2171 | 0.5715 to 2.5918 | 0.6123 |
| hsa miR-221 (Low vs. High) | 2.0042 | 0.9687 to 4.1466 | 0.0515 | 1.6422 | 0.7260 to 3.7148 | 0.236 |

HR, hazard ratio;
CI, confidence interval

Association between miRNA expression and CRC distant metastasis (Logistic regression model)

| | Univariate | | | Multivariate | | |
|---|---|---|---|---|---|---|
| Characteristics | OR | 95% CI | P | OR | 95% CI | P |
| Tumor Suppressor-miRNAs | | | | | | |
| Age (>50 vs. ≤50) | 0.7941 | 0.0855 to 7.3728 | 0.8428 | 0.9606 | 0.0515 to 17.9084 | 0.9785 |
| Sex (Male vs. Female) | 1.1034 | 0.2129 to 5.7192 | 0.906 | 1.7938 | 0.1980 to 16.2543 | 0.6033 |
| T stage (T3/4 vs. T1/2) | 2.05E+07 | 0.0000 to 0.0000 | 0.0673 | 6.76E+06 | 0.0000 to 0.0000 | 0.9933 |
| N stage (N1/2/3/ vs. N0) | 9 | 1.0850 to 74.6570 | 0.0102 | 9.4862 | 0.7958 to 113.760 | 0.0752 |
| hsa-let-7i (Low vs. High) | 19.25 | 4.1320 to 89.6808 | 0.0001 | 21.6846 | 2.8783 to 163.3687 | 0.0028 |
| hsa-miR-320a (Low vs. High) | 5.5152 | 1.3048 to 23.3120 | 0.0144 | 1.278 | 0.1682 to 9.7117 | 0.8126 |
| Oncogenic-miRNAs | | | | | | |
| Age (>50 vs. ≤50) | 0.7941 | 0.0855 to 7.3728 | 0.8428 | 0.3696 | 0.0251 to 5.4427 | 0.4682 |
| Sex (Male vs. Female) | 1.1034 | 0.2129 to 5.7192 | 0.906 | 0.7354 | 0.0898 to 6.0226 | 0.7745 |
| T stage (T3/4 vs. T1/2) | 2.05E+7 | 0.0000 to 0.0000 | 0.0673 | 3.06E+07 | 0.0000 to 0.0000 | 0.9954 |

TABLE 12-continued

Univariate and Multivariate analysis for Prognosis in CRC in the miRNA Microarray Cohort

| | | | | | | |
|---|---|---|---|---|---|---|
| N stage (N1/2/3 vs. N0) | 9 | 1.0850 to 74.6570 | 0.0102 | 10.1931 | 0.8934 to 116.2990 | 0.0616 |
| hsa-miR-10b (High vs. Low) | 7.625 | 1.8645 to 31.1838 | 0.0044 | 7.2025 | 1.1757 to 44.1224 | 0.0328 |
| hsa-miR-221 (High vs. Low) | 9 | 1.0850 to 74.6570 | 0.0102 | 8.5366 | 0.8788 to 82.9198 | 0.0645 |

OR, odds ratio;
CI, confidence interval

The expression of these 4 miRNAs was associated with survival in CRC patients. Low expression of let-7i was significantly associated with poor survival in CRC patients (P=0.0082, Kaplan-Meier log-rank test; FIG. 9). Significant associations with survival were not observed for the other miRNAs. Univariate Cox regression analysis revealed that low let-7i expression (HR, 2.7; 95% CI, 1.3 to 5.7; P=0.0066) was significantly associated with poor prognosis (Table 12). In the multivariate model, low let-7i expression (HR, 2.3; 95% CI, 1.0 to 5.1; P=0.0471) was significantly associated with poor survival, independent of other clinical factors.

Validation of Metastasis Specific miRNAs (Let-7i and miR-10b) in Primary CRC.

While microarray analysis can detect differential miRNA expression for thousands of miRNAs simultaneously, it is limited in that it is less accurate than more targeted approaches to measure gene expression. Therefore, the expression of let-7i and miR-10b was measured using qRT-PCR analysis in an independent cohort of 175 CRCs (Table 14 and Table 13). Reduced let-7i expression was significantly associated with lymph node metastasis (P=0.0407), distant metastasis (P<0.0001), and advanced TNM stage (P=0.0002; Table 14). In contrast, increased miR-10b expression was significantly associated with higher T stage (P=0.0183), distant metastasis (P=0.0486), and advanced TNM stage (P=0.0208; Table 14). Univariate logistic regression models provided similar results that low let-7i expression (OR, 6.0; 95% CI, 1.4 to 26.2; P=0.0175) and high miR-10b expression (OR, 2.9; 95% CI, 0.8 to 10.0; P=0.05) were significantly associated with CRC distant metastasis (Table 13). The multivariate logistic regression model showed that low let-7i expression (OR, 5.5; 95% CI, 1.1 to 26.8; P=0.0334) and high miR-10b expression (OR, 4.9; 95% CI, 1.2 to 19.7; P=0.0248) were independently associated with CRC distant metastasis (Table 2).

TABLE 13

Univariate and Multivariate analysis for Prognosis in the miRNA Microarray Validation Cohort Association between miRNA expression and CRC prognosis (Cox proportional hazards model)

| | Univariate | | | Multivariate | | |
|---|---|---|---|---|---|---|
| Characteristics | HR | 95% CI | P | HR | 95% CI | P |
| Tumor Suppressor-miRNA | | | | | | |
| Age (>50 vs. ≤50) | 0.8034 | 0.4370 to 1.4772 | 0.4816 | 1.5292 | 0.7667 to 3.0497 | 0.2302 |
| Sex (Male vs. Female) | 1.1504 | 0.6133 to 2.1576 | 0.662 | 1.7865 | 0.8779 to 3.6351 | 0.1112 |
| T stage (T3/4 vs. T1/2) | 7.9376 | 1.9318 to 32.6160 | 0.0001 | 1.7132 | 0.3924 to 7.4801 | 0.4763 |
| N stage (N1/2/3 vs. N0) | 15.179 | 5.4217 to 42.4966 | <0.0001 | 6.4354 | 2.1295 to 19.4484 | 0.001 |
| Liver metastasis (Present vs. Absent) | 12.0601 | 6.0761 to 23.9370 | <0.0001 | 6.6859 | 2.9471 to 15.1679 | <0.0001 |
| Pathology (Poor diff. vs. Well/Mod diff.) | 1.8409 | 0.7747 to 4.3745 | 0.2005 | 4.1071 | 1.3989 to 12.0579 | 0.105 |
| CEA (>5 vs. ≤5) | 5.4597 | 2.2795 to 13.0769 | <0.0001 | 1.5946 | 0.6224 to 4.0854 | 0.3335 |
| hsa-let-7i (Low vs. High) | 5.3525 | 1.3009 to 22.0225 | 0.0026 | 4.9928 | 1.0236 to 24.3539 | 0.0479 |
| Oncogenic-miRNA | | | | | | |
| Age (>50 vs. ≤50) | 0.8034 | 0.4370 to 1.4772 | 0.4816 | 1.1385 | 0.5793 to 2.2373 | 0.7082 |
| Sex (Male vs. Female) | 1.1504 | 0.6133 to 2.1576 | 0.662 | 1.4498 | 0.7408 to 2.8372 | 0.2807 |
| T stage (T3/4 vs. T1/2) | 7.9376 | 1.9318 to 32.6160 | 0.0001 | 1.958 | 0.4413 to 8.6885 | 0.3792 |
| N stage (N1/2/3 vs. N0) | 15.179 | 5.4217 to 42.4966 | <0.0001 | 6.2874 | 2.0393 to 19.3844 | 0.0015 |
| Liver metastasis (Present vs. Absent) | 12.0601 | 6.0761 to 23.9370 | <0.0001 | 5.947 | 2.5832 to 13.6912 | <0.0001 |
| Pathology (Poor diff. vs. Well/Mod diff.) | 1.8409 | 0.7747 to 4.3745 | 0.2005 | 2.4743 | 0.9038 to 6.7735 | 0.0794 |
| CEA (>5 vs. ≤5) | 5.4597 | 2.2795 to 13.0769 | <0.0001 | 1.6744 | 0.6299 to 4.4506 | 0.3039 |
| hsa miR-10b (High vs. Low) | 1.5655 | 0.6622 to 3.7008 | 0.3097 | 0.8235 | 0.3461 to 1.9597 | 0.6623 |

HR, hazard ratio;
CI, confidence interval

Association between miRNA expression and CRC distant metastasis (Logistic regression model)

| | Univariate | | | Multivariate | | |
|---|---|---|---|---|---|---|
| Characteristics | OR | 95% CI | P | OR | 95% CI | P |
| Tumor Suppressor-miRNA | | | | | | |
| Age (>50 vs. ≤50) | 0.5635 | 0.2869 to 1.1067 | 0.0958 | 0.5413 | 0.2217 to 1.3217 | 0.1778 |
| Sex (Male vs. Female) | 1.0833 | 0.5508 to 2.1306 | 0.8166 | 1.2078 | 0.4896 to 2.9798 | 0.682 |

TABLE 13-continued

Univariate and Multivariate analysis for Prognosis in the miRNA Microarray Validation Cohort

| | | | | | | |
|---|---|---|---|---|---|---|
| T stage (T3/4 vs. T1/2) | 5.38E+00 | 1.8281 to 15.8255 | 0.0022 | 2.04E+00 | 0.4865 to 8.5711 | 0.3294 |
| N stage (N1/2/3 vs. N0) | 33.1739 | 9.7845 to 112.4748 | <0.0001 | 23.3729 | 6.5455 to 83.4610 | <0.0001 |
| hsa-let-7i (Low vs. High) | 5.9853 | 1.3679 to 26.1892 | 0.0175 | 5.5371 | 1.1441 to 26.7989 | 0.0334 |
| Oncogenic-miRNA | | | | | | |
| Age (>50 vs. ≤50) | 0.5635 | 0.2869 to 1.1067 | 0.0958 | 0.4126 | 0.1681 to 1.0127 | 0.0533 |
| Sex (Male vs. Female) | 1.0833 | 0.5508 to 2.1306 | 0.8166 | 1.2263 | 0.4921 to 3.0563 | 0.6615 |
| T stage (T3/4 vs. T1/2) | 5.38E+00 | 1.8281 to 15.8255 | 0.0022 | 2.41E+00 | 0.5730 to 10.1297 | 0.2301 |
| N stage (N1/2/3 vs. N0) | 25.6744 | 7.4879 to 88.0324 | <0.0001 | 25.3355 | 7.0170 to 91.4763 | <0.0001 |
| hsa miR-10b (High vs. Low) | 2.8624 | 0.8176 to 10.0217 | 0.05 | 4.9134 | 1.2237 to 19.7286 | 0.0248 |

OR, odds ratio;
CI, confidence interval

TABLE 14

Clinical Relevance of 3 miRNAs (let-7i, miR-10b, and miR-885-5p) in miRNA Microarray Validation Cohort (Kruskal-Wallis Test)

| | hsa-let-7i | | | hsa-miR-10b | | | hsa-miR-885-5p | | |
|---|---|---|---|---|---|---|---|---|---|
| | n | mean ± SD | P value | n | mean ± SD | P value | n | mean ± SD | P value |
| Sex | | | 0.9441 | | | 0.1311 | | | 0.5311 |
| Male | 102 | 0.7862 ± 0.2881 | | 102 | 0.05870 ± 0.02865 | | 102 | 0.0006554 ± 0.0007500 | |
| Female | 73 | 0.7956 ± 0.2960 | | 73 | 0.05391 ± 0.03159 | | 73 | 0.0005863 ± 0.0004942 | |
| Age (Years) | | | 0.6466 | | | 0.5857 | | | 0.4619 |
| ≤50 | 86 | 0.7938 ± 0.2804 | | 86 | 0.05588 ± 0.03143 | | 86 | 0.0005798 ± 0.0004904 | |
| >50 | 89 | 0.7875 ± 0.3012 | | 89 | 0.05734 ± 0.02864 | | 89 | 0.0006717 ± 0.0007817 | |
| T stage | | | 0.6927 | | | 0.0183 | | | 0.3976 |
| T1/T2 | 50 | 0.7441 ± 0.1990 | | 50 | 0.04823 ± 0.02788 | | 50 | 0.0005246 ± 0.0003865 | |
| T3/T4 | 125 | 0.8081 ± 0.3183 | | 125 | 0.06036 ± 0.02983 | | 125 | 0.0006675 ± 0.0007339 | |
| N stage | | | 0.0407 | | | 0.6505 | | | 0.3597 |
| N0 | 95 | 0.8375 ± 0.3025 | | 95 | 0.05571 ± 0.03017 | | 95 | 0.0006975 ± 0.0008064 | |
| N1/N2/N3 | 80 | 0.7235 ± 0.2608 | | 80 | 0.05808 ± 0.02981 | | 80 | 0.0005445 ± 0.0003985 | |
| M stage | | | <0.0001 | | | 0.0486 | | | 0.3175 |
| M0 | 135 | 0.8517 ± 0.3013 | | 135 | 0.05443 ± 0.02938 | | 135 | 0.0006501 ± 0.0006979 | |
| M1 | 40 | 0.6133 ± 0.1562 | | 40 | 0.06701 ± 0.03105 | | 40 | 0.0005515 ± 0.0004856 | |
| TNM stage | | | 0.0002 | | | 0.0208 | | | 0.7954 |
| I | 38 | 0.7513 ± 0.2090 | | 38 | 0.04884 ± 0.03021 | | 38 | 0.0005713 ± 0.0004014 | |
| II | 53 | 0.8889 ± 0.3261 | | 53 | 0.06255 ± 0.03029 | | 53 | 0.0007243 ± 0.0009604 | |
| III | 44 | 0.8896 ± 0.3245 | | 44 | 0.05029 ± 0.02540 | | 44 | 0.0006289 ± 0.0005012 | |
| IV | 40 | 0.6133 ± 0.1562 | | 40 | 0.06701 ± 0.03105 | | 40 | 0.0005515 ± 0.0004856 | |

Kaplan-Meier survival analysis revealed that low expression of let-7i was significantly associated with poor survival in CRC patients (P=0.0095), validating the findings from the microarray validation cohort (FIG. 10). MiR-10b expression was not associated with survival. Using univariate Cox proportional hazard models (Table 13), low let-7i expression (HR, 5.4; 95% CI, 1.3 to 22.0; P=0.0026) was significantly associated with poor prognosis. In the multivariate Cox regression model, low let-7i expression (HR, 5.0; 95% CI, 1.0 to 24.4; P=0.0479) was significantly associated with poor patient survival independent of other clinical covariates.

miR-885-5p Expression Pattern in Primary CRC Tissue and Serum Specimens.

As described previously, miR-885-5p was the only miRNA to be elevated in LM compared to pCRC in two cohorts. Since this miRNA is elevated in LM, it was envisaged that circulating levels of this miRNA would be associated with the presence of metastasis. Therefore, the association of miR-885-5p was examined in matched pCRC tissue and serum samples in the context of various clinico-pathological factors (Table 15). This is the first study to interrogate the role of miR-885-5p in CRC and cancer metastasis. Serum miR-885-5p expression was significantly correlated with lymph node metastasis (P=0.0327), distant metastasis (P=0.0069), TNM stage (P=0.0235), liver metastasis (P=0.0011), and lymphatic invasion (P=0.0141). Tissue expression of miR-885-5p expression was not associated with clinico-pathological factors.

TABLE 15

Clinical Relevance of Tissue- and Serum-miR-885-5p Expression in Matched CRC Tissue and Serum Cohort

| | Tissue miR-885-5p | | | Serum miR-885-5p | | |
|---|---|---|---|---|---|---|
| | Low (n = 123) | High (n = 52) | P value ($\chi^2$ test) | Low (n = 94) | High (n = 75) | P value ($\chi^2$ test) |
| Sex | | | 0.4623 | | | 0.5533 |
| Male | 69 | 33 | | 51 | 45 | |
| Female | 54 | 19 | | 43 | 30 | |
| Age (Years) | | | 0.9857 | | | 0.0011 |
| ≤68 | 61 | 25 | | 34 | 47 | |
| >68 | 62 | 27 | | 60 | 28 | |
| Histological Grade | | | 0.2475 | | | 0.6393 |
| well/mod. | 110 | 50 | | 85 | 66 | |

TABLE 15-continued

Clinical Relevance of Tissue- and Serum-miR-885-5p Expression in Matched CRC Tissue and Serum Cohort

| | Tissue miR-885-5p | | | Serum miR-885-5p | | |
|---|---|---|---|---|---|---|
| | Low (n = 123) | High (n = 52) | P value ($\chi^2$ test) | Low (n = 94) | High (n = 75) | P value ($\chi^2$ test) |
| poor/mucin. | 13 | 2 | | 8 | 9 | |
| T-stage | | | 0.2785 | | | 0.0733 |
| T1/T2 | 37 | 11 | | 31 | 15 | |
| T3/T4 | 84 | 41 | | 60 | 59 | |
| N stage | | | 0.1717 | | | 0.0327 |
| N0 | 62 | 33 | | 61 | 36 | |
| N1/N2/N3 | 60 | 19 | | 31 | 38 | |
| M stage | | | 0.3921 | | | 0.0069 |
| M0 | 92 | 43 | | 83 | 54 | |
| M1 | 30 | 9 | | 9 | 20 | |
| TNM stage | | | 0.4479 | | | 0.0235 |
| I | 28 | 10 | | 26 | 11 | |
| II | 33 | 20 | | 34 | 24 | |
| III | 31 | 13 | | 23 | 19 | |
| IV | 30 | 9 | | 10 | 20 | |
| Liver Metastasis | | | 0.473 | | | 0.0011 |
| Absent | 101 | 46 | | 89 | 59 | |
| Present | 21 | 6 | | 3 | 15 | |
| Lymphatic Invasion | | | 0.8579 | | | 0.0141 |
| Absent | 25 | 12 | | 30 | 11 | |
| Present | 97 | 40 | | 62 | 63 | |

Logistic regression was used to further analyze the association between miR-855-5p and lymph node metastasis and distant metastasis, respectively (Table 16). Univariate logistic regression showed that high serum miR-885-5p expression was significantly associated with lymph node metastasis (OR, 2.1; 95% CI, 1.1 to 3.9; P=0.0226) and distant metastasis (OR, 3.4; 95% CI, 1.4 to 8.1; P=0.005). Multivariate models demonstrated that these associations were significant independent of other clinical factors.

TABLE 16

Univariate and Multivariate analysis of miR-885-5p for Prognosis and Predicting Metastasis in the CRC Tissue and Matching Serum Cohort Association between miRNA expression and CRC prognosis (Cox proportional hazards model)

| | Univariate | | | Multivariate | | |
|---|---|---|---|---|---|---|
| Characteristics | HR | 95% CI | P | HR | 95% CI | P |
| Age (>68 vs. ≤68) | 0.7616 | 0.4299 to 1.3494 | 0.3533 | 1.1699 | 0.4961 to 2.7586 | 0.7213 |
| Sex (Male vs. Female) | 1.085 | 0.6016 to 1.9568 | 0.7875 | 1.3956 | 0.5947 to 3.2751 | 0.4461 |
| Tumor size (>40 mm vs. ≥40 mm) | 2.3542 | 1.2735 to 4.3520 | 0.0066 | 0.7836 | 0.2918 to 2.1044 | 0.6302 |
| Lymph node metastasis (Present vs. Absent) | 17.0534 | 6.1307 to 47.4364 | <0.0001 | 7.8017 | 1.5470 to 39.3444 | 0.0133 |
| Distant metastasis (Present vs. Absent) | 35.9342 | 14.7708 to 87.4199 | <0.0001 | 15.094 | 4.7369 to 48.0965 | <0.0001 |
| CEA (>5 vs. ≤5) | 5.1397 | 2.2864 to 11.5539 | 0.0001 | 0.865 | 0.2627 to 2.8482 | 0.8125 |
| Tissue miR-885-5p (High vs. Low) | 0.9545 | 0.4793 to 1.9006 | 0.895 | 0.8698 | 0.3293 to 2.2971 | 0.7793 |
| Serum miR-885-5p (High vs. Low) | 3.9389 | 1.9139 to 8.1064 | 0.0002 | 2.8715 | 1.0985 to 7.5065 | 0.0323 |

| | Univariate | | | Multivariate | | |
|---|---|---|---|---|---|---|
| Characteristics | OR | 95% CI | P | OR | 95% CI | P |

Association between miRNA expression and CRC lymph node metastasis (Logistic regression model)

| | | | | | | |
|---|---|---|---|---|---|---|
| Age (>68 vs. ≤68) | 0.8584 | 0.4909 to 1.5010 | 0.5922 | 1.4775 | 0.6497 to 3.3599 | 0.3518 |
| Sex (Male vs. Female) | 0.813 | 0.4615 to 1.4323 | 0.4736 | 0.5447 | 0.2496 to 1.1890 | 0.1272 |
| Tumor size (>40 mm vs. ≤40 mm) | 2.2631 | 1.2759 to 4.0139 | 0.0052 | 1.8862 | 0.8232 to 4.3220 | 0.1336 |
| Pathology (poor diff. vs. diff.) | 2.1429 | 0.7945 to 5.7798 | 0.1322 | 1.6497 | 0.4090 to 6.6534 | 0.4817 |
| Venous Invasion (Present vs. Absent) | 3.9899 | 2.2057 to 7.2172 | <0.0001 | 2.0285 | 0.9105 to 4.5195 | 0.0835 |
| CEA (>5 vs. ≤5) | 3.6033 | 1.8993 to 6.8358 | 0.0001 | 2.1167 | 0.9228 to 4.8550 | 0.0767 |
| Tissue miR-885-5p (High vs. Low) | 0.5949 | 0.3054 to 1.1589 | 0.1269 | 0.4712 | 0.2036 to 1.0906 | 0.0788 |
| Serum miR-885-5p (High vs. Low) | 2.0771 | 1.1082 to 3.8931 | 0.0226 | 3.0334 | 1.2821 to 7.1769 | 0.0116 |

TABLE 16-continued

Univariate and Multivariate analysis of miR-885-5p for Prognosis and
Predicting Metastasis in the CRC Tissue and Matching Serum Cohort Association between miRNA expression and CRC distant metastasis (Logistic regression model)

| | | | | | | |
|---|---|---|---|---|---|---|
| Tumor size (>40 mm vs. ≤40 mm) | 3.3237 | 1.5934 to 6.9329 | 0.0014 | 1.8114 | 0.5150 to 6.3706 | 0.3545 |
| Lymph node metastasis (Present vs. Absent) | 33.1739 | 9.7845 to 112.4748 | <0.0001 | 34.7324 | 4.3232 to 279.0353 | 0.0008 |
| Venous Invasion (Present vs. Absent) | 5.7811 | 2.7147 to 12.3112 | <0.0001 | 4.8212 | 1.3647 to 17.0316 | 0.0146 |
| Tissue miR-885-5p (High vs. Low) | 0.6419 | 0.2804 to 1.4694 | 0.2941 | 0.5726 | 0.1639 to 2.0008 | 0.3824 |
| Serum miR-885-5p (High vs. Low) | 3.4156 | 1.4481 to 8.0564 | 0.005 | 3.1241 | 0.9731 to 10.0299 | 0.0456 |

HR, hazard ratio;
CI, confidence interval
OR, odds ratio;

Kaplan-Meier survival analysis showed that high expression of serum miR-885-5p was significantly associated with poor survival (P<0.0001) (FIG. 11), while tissue miR-885-5p expression was not (P=0.9556). Similarly, univariate Cox regression revealed that high serum miR-885-5p expression (HR, 3.9; 95% CI, 1.9 to 8.1; P=0.0002) was significantly associated with poor prognosis (Table 16). In the multivariate model, high serum miR-885-5p expression (HR, 2.9; 95% CI, 1.1 to 7.5; P=0.0323) was significantly associated with poor survival independent of other clinical characteristics including tumor size, venous invasion, and levels of CEA expression.

Expression of CRC Metastasis Specific miRNAs (Let-7i, miR-10b, and miR-885-5p).

To further confirm the pathologic expression patterns of let-7i, miR-10b, and miR-885-5p, in situ hybridization (ISH) staining was performed on pCRCs with and without metastasis (FIG. 8A), and in matched pCRC and LM tissues (FIG. 8B). Consistent with the quantitative PCR (qPRC) results, ISH analysis showed low let-7i and high miR-10b expression in late stage pCRCs with metastasis compared to early stage pCRCs without metastasis, while miR-885-5p expression was comparable between early stage pCRCs without metastasis and late stage pCRCs with metastasis. Downregulated expression of let-7i and miR-10b and up-regulated miR-885-5p expression was observed in LM compared to pCRC. Interestingly, adjacent hepatocytes barely expressed any of the 3 CRC metastasis-specific miRNAs.

Example 3—Serum miR-21 as a Promising Biomarkers for the Early Detection and Prognosis of Colorectal Cancer Materials and Methods Study Design—

The present study included analysis of 568 serum and tissue specimens that were obtained from healthy volunteers and consecutively enrolled patients with colorectal adenomas and cancers, at the Mie University Medical Hospital, Japan, between Jan. 1, 2005 and Dec. 31, 2010. This study was designed as an initial screening phase and a subsequent validation phase. In the screening phase, oncogenic miR-21 and miR-31 were selected (Meng 2007; Zhu 2007; Asangani 2008; Wang 2009; Cottonham 2008), and their expression was measured using TaqMan-based quantitative RT-PCR (qRT-PCR) using cell culture medium and matched serum and tissue samples. To determine the secretory potential of these miRNAs, two CRC cell lines, HCT 116 and SW620, were cultured and a fraction of culture medium was collected at 0, 24 and 48 h after the initial seeding of cells in 10 cm dishes. In addition, a small set of pre-operative serum samples were collected from 12 CRC patients and from 12 gender- and age-matched healthy subjects as controls. To further assess the specificity of miRNA expression in serum, CRC and adjacent normal tissues were analyzed from 8 of the 12 CRC patients, from whom both matched normal and neoplastic tissues were available.

In the validation phase, changes in miRNA expression patterns in serum and tissues from CRC patients were validated in a large, independent cohmi of patients where preoperative sera (n=186) and matched surgical tissues (n=166) were collected from a pool of 200 CRC patients. Additionally, post-operative sera (day 7 post-operation) were collected from an independent set of 60 patients where matching pre-operative sera were available to determine whether miRNA expression was altered subsequent to tumor resection. To better appreciate the diagnostic utility of these miRNAs, sera from 43 patients with advanced adenomas and 53 healthy controls were also collected. The serum specimens from healthy subjects were age- and gender matched, and each volunteer had a negative colonoscopic examination and no prior diagnosis of any other malignancy. All CRC patients who underwent surgery were followed up for tumor recurrence at regular intervals for up to 5 years. During each annual hospital visit, all patients underwent a chest X-ray, colonoscopy and abdominal Computerized Tomography. Survival time was calculated from date of diagnosis to the date of death or last of follow up. Patients treated with radiotherapy or chemotherapy prior to surgery were excluded from the study. Patients with stage III/IV disease received 5-fluorouracil-based chemotherapy, whereas no adjuvant therapy was given to stage I/II CRC patients.

Ethics Statement—

Both serum- and tissue-based specimen collection and studies were approved by the Institutional Review Boards (IRB) of the Mie University Hospital, Japan and Baylor University Medical Centre, Dallas, USA. All participants provided written consent and willingness to donate their blood and tissue samples for research.

RNA Isolation and qRT-PCR—

MiRNA extraction from serum and culture media samples was performed with miRNeasy RNA isolation Kit (Qiagen, Valencia, Calif.), while those from FFPE samples using RecoverAll Total Nucleic Acid Isolation Kit (Ambion Inc., Austin, Tex.). TaqMan miRNA real-time RT-PCRs (Applied Biosystems, Foster City, Calif.) were employed to detect and quantify the miRNAs expression using the $2^{-\Delta Ct}$ method.

Statistical Analyses—

Results were expressed as mean±SD (standard deviation). Mann-Whitney U and Kruskal-Wallis tests of variance (ANOVA) were used to evaluate statistical differences in serum or tissue miRNA expression between unpaired groups, and multiple comparison groups, respectively. Wilcoxon test was used to compare miR-21 expression in paired serum samples obtained pre- and 7 day post-surgical tumor resection. The Spearman's correlation test was used to examine correlation between miRNA expression in serum and matched CRC tissues. Receiver operating characteristic (ROC) analysis was performed to determine the diagnostic performance of miR-21 expression levels in distinguishing patients with colorectal adenomas or cancers from the healthy controls. Sensitivity against 1-specificity was plotted at each cut-off threshold, and the area under the curve (AUC) values that reflect the probability of correctly identifying adenoma or CRC patients from controls were computed. The optimal cut-off threshold for diagnosis were obtained by Youden Index (Ruopp 2008). In brief, the optimal cut-off threshold values were determined at the point on ROC curve at which Youden's Index (sensitivity+specificity−1) was maximal. By using these optimal cut-off values, sensitivity, specificity, Positive and Negative Predictive Values (PPV and NPV) were calculated.

To validate the accuracy estimates of ROC curves and optimal cut-off threshold values and to adjust for optimism bias in discriminating CRC or adenoma patients from controls, the bootstrap bias-correction and accelerated (BCa) bootstrap methods were performed (Efron 1987). In general, there are no standard recommended methods for adjusting bias. However, BCa bootstrap method was selected because it adjusts for both bias and skewness in the bootstrap distribution of data. For this analysis, data were randomly included from the original serum samples, followed by sensitivity and 1-specificity determination for various cut-off thresholds. This process was repeated 1000 times, and resultant mean values (95% confidence interval) for sensitivity and specificity were computed. In addition, ROC convex hull (ROCCH) curves were generated using approaches that allowed hull segment to be viewed as being generated by a tie between the plots of sensitivity and specificity for various cutoffs from the original data and adjusted data by BCa bootstrap methods. Thereafter, the AUCs of ROCCH curves were calculated by Trapezoidal rule. Finally, a two-sided z-test was used to compare the AUCs of two ROC curves (Hanley 1983). Multivariate logistic regression model was used to calculate odds ratios (ORs) for age and gender adjusted cases being associated with CRC or adenoma according to serum miRNA levels.

It was estimated that 154 patients were needed to achieve 80% power to substantiate more that 20% differences in prognostic outcome, a number that was much smaller than the cohort of 200 CRC patients. Survival analyses were performed using the Kaplan-Meier method and the differences in survival were examined using log-rank tests. ROC curves were established to discriminate the patients with or without death, and the Youden Index (Ruopp 2008) was used to determine the optimal cut-off threshold of serum or tissue miRNAs levels to predict the overall survival. Cox's proportional hazard regression analyses were used to estimate hazard ratios of death according to serum and tumor miRNA levels, unadjusted and adjusted for potential confounding factors for death including age, gender, pathological differentiation, T stage, N stage, M stage and serum CEA levels. All P-values are two-sided; P<0.05 was considered significant. All statistical analyses were carried out using Medcalc v12.3.0 (Broekstraat 52, 9030, Mariakerke, Belgium).

Results

MiR-21 Expression in Colorectal Cancer Cell Culture Medium—

In this initial experiment, it was determined whether miR-21 and miR-31 act as secretory miRNAs and are excreted into the culture media by HCT116 and SW620 CRC cell lines. miR-21 expression in the culture media from both cell lines increased with time (24 and 48 hours; P<0.05), and with increasing numbers of tumor cells (P<0.05); (FIG. 1A: HCT116, FIG. 1B: SW620). However, miR-31 expression levels did not show significant changes in either cell line (FIG. 1C: HCT116, FIG. 1D: SW620), suggesting that miR-21 but not miR-31, is a secretory miRNA.

Tissue and Serum miR-21 Expression During Screening Phase—

Figures 13A, 13B, 13C, 13D, 13E, 13F, 13G, 13H:
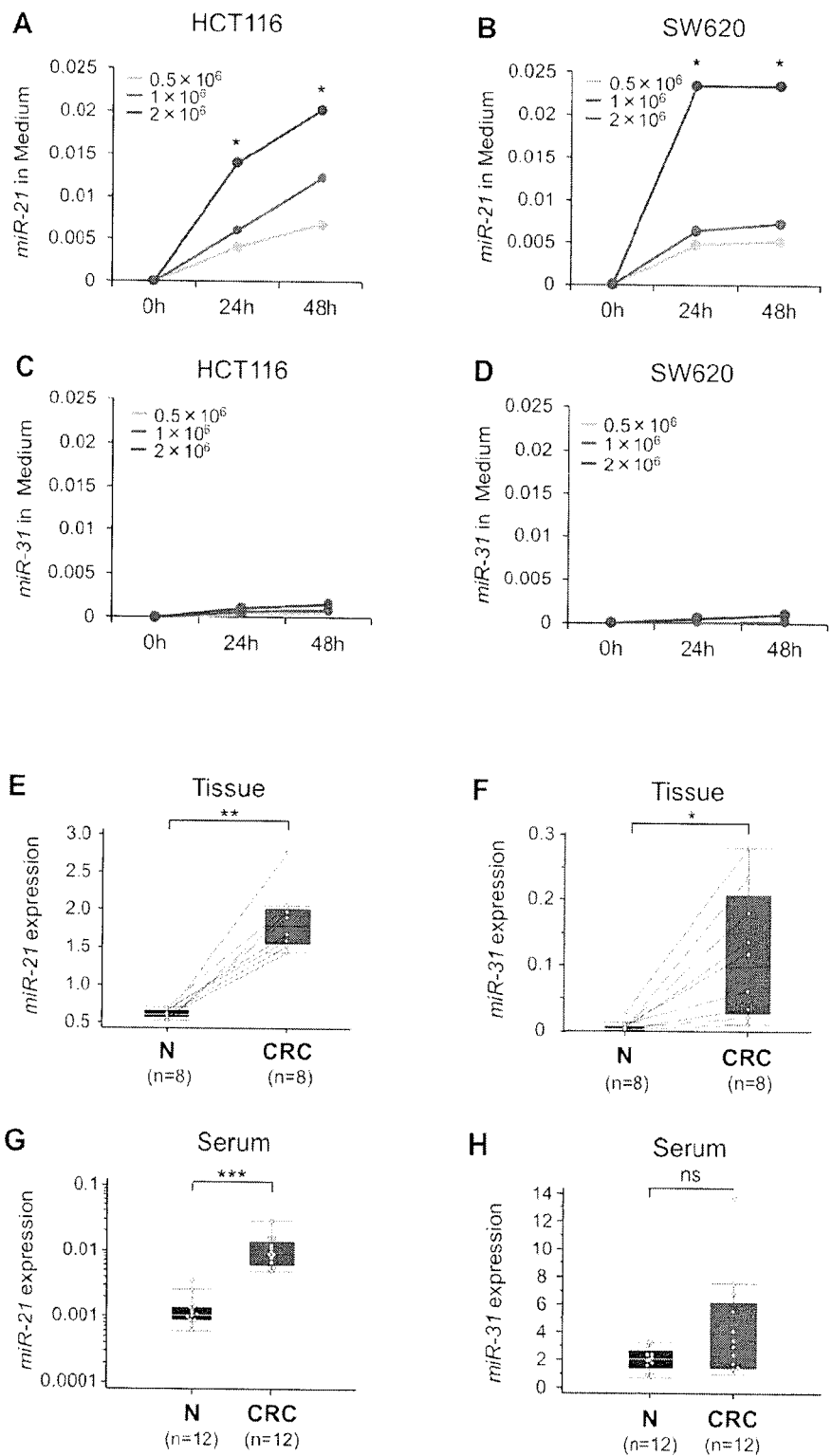
FIGS. 13A-13H—Expression of miR-21 and miR-31 in culture media of CRC cell lines (HCT116 and SW620). MiR-21 levels in media of both HCT116 (A) and SW620 (B) increased with increased cell counts (0.5-2×10$^6$ cells/well) and longer incubation intervals, while MiR-31 levels did not change in either cell line (C, D). Y-axis represents relative expression of miR-21 and miR-31 normalized to cel-miR-39. Initial screening for miR-21 and miR-31 expression in the screening phase, using a small subset of tissue and serum specimens from CRC patients. Box plots for miR-21 expression (E) and miR-31 expression (F) levels in primary tumor tissues (CRC) and adjacent normal mucosa (N) from 8 CRC patients. Box plots for serum levels of miR-21 (G) and miR-31 (H) in mucosa from normal control patients (N; n=12) and CRC patients (n=12). Boxes represent interquartile range and the horizontal line across each box indicates median value. Y-axis represents relative expression of miR-21 and miR-31 and data were normalized to cel-miR-39 and miR-16 expression in sera and tissue, respectively. Statistical analysis was performed using Wilcoxon and Mann-Whitney U tests. *, P<0.05; , P<0.01; *, P<0.0001; ns, not significant.

In the screening phase of the study, miR-21 and miR-31 expression was determined in a small set of 8 CRCs and the adjacent normal mucosa. Both miR-21 and miR-31 levels were significantly elevated in CRC tissues compared to adjacent normal control tissues (miR-21: P<0.01; miR-31; P<0.05; FIG. 13E, FIG. 13F). The feasibility of detecting the expression of circulating miR-21 and miR-31 was examined in 24 serum samples from CRC patients (n=12) and healthy controls (n=12). miR-21 levels were significantly elevated in the sera of CRC patients (P<0.0001; FIG. 13G), while no significant differences were noted in serum miR-31 expression between CRC patients and controls (P>0.05; FIG. 13H). Based on the results that only miR-21 acts a secretory miRNA the next study focused on miR-21 for further assessment of its efficacy as a diagnostic and prognostic biomarker in patients with colorectal neoplasia.

Tissue and Serum miR-21 Expression During Validation Phase—Patient Characteristics—

The clinicopathological and other patient characteristics are summarized in Table 17. There were no significant differences in age between healthy controls (mean, 64 years; SD, 12.9 years) and patients with adenomas (mean, 66 years; SD, 9.8 years) or CRCs (mean, 67 years; SD, 7.5 years; P>0.05). Likewise, there were no gender differences between different groups which comprised of 27 males and 26 females in the control group, 30 males and 13 females in the adenoma group and 106 males and 80 females in the CRC group (P>0.05). The median follow-up time period for CRC patients was 44 months (range: 2-84 months).

TABLE 17

Patient characteristics for serum and tissue miR-21 expression analysis in the validation set

| Characteristics | All CRC patients n = 200 | Patients analyzed for serum analysis n = 186 | Patients analyzed for tissue analysis n = 166 | Patients with adenomas n = 43 | Healthy controls n = 53 | P-value |
|---|---|---|---|---|---|---|
| Age (years) | | | | | | |
| Mean ± SD | 67.5 ± 7.5 | — | — | 66 ± 9.8 | 64 ± 12.9 | ns |
| Gender | | | | | | |
| Male | 117 | 106 | 100 | 30 | 27 | ns |
| Female | 83 | 80 | 66 | 13 | 26 | |
| TNM stage | | | | | | |
| I | 46 | 45 | 37 | — | — | |
| II | 62 | 57 | 51 | — | — | |
| III | 48 | 43 | 43 | — | — | |
| IV | 44 | 41 | 35 | — | — | |

CRC: colorectal cancer;
TNM: tumor-node-metastasis staging system;
DS: Standard Deviation;
ns: not significance Serum miR-21 Expression in Patients with Colorectal Adenomas and Cancers—

To evaluate the diagnostic potential of miR-21, a total of 282 serum samples, including those from patients with CRC (n=186), adenomatous polyps (n=43) and normal controls (n=53) were examined. In comparison to healthy controls, the expression levels of serum miR-21 demonstrated a stepwise increase in patients with adenomatous polyps (P<0.0001; FIG. 13A) and CRC (P<0.0001; FIG. 13A). Furthermore, when all CRC patients were segregated based upon TNM stage, the gradual increase in serum miR-21 levels was clearly discernible with significantly higher expression levels in stage IV patients compared to stage I or II patients (P<0.05 or P<0.05, respectively; FIG. 13B).

Next, ROC curves were generated to assess the potential usefulness of serum miR-21 as a noninvasive biomarker for the early diagnosis of colorectal neoplasia. The ROC analyses revealed that serum miR-21 levels were robust in discriminating patients with CRC from control subjects, with AUC value of 0.927 (95% CI: 0.886-0.956; FIG. 14A). Using a cutoff value of 0.0019, the sensitivity, specificity, PPV and NPV were 82.8%, 90.6%, 96.3% and 60.8%, respectively to identify a patient with CRC (Table 18). Even more important from a screening perspective, serum miR-21 levels could reliably differentiate patients with advanced adenomatous polyps from healthy controls, as evidenced by AUC value of 0.803 (95% CI: 0.669-0.869; FIG. 14B). With a cutoff value of 0.0013, the sensitivity, specificity, PPV and NPV were 76.8% and 81.1%, 76.7% and 81.1%, respectively (Table 18).

TABLE 18

Actual Numbers divided by optimal cutoff value and the associated values for sensitivity, specificity, PPV and NPV Colorectal Cancer (CRC) vs. Controls

| | CRC | Controls | Total |
|---|---|---|---|
| serum miR-21 >0.0019 (cutoff) | 154 | 5 | 160 |
| serum miR-21 ≤0.0019 (cutoff) | 32 | 48 | 79 |
| Total | 186 | 53 | 239 |
| PPV (%) | 96.3 | Sensitivity (%) | 82.8 |
| NPV (%) | 60.8 | Specificity (%) | 90.6 |

Adenoma vs. Controls

| | Adenoma | Controls | Total |
|---|---|---|---|
| serum miR-21 >0.0013 (cutoff) | 33 | 10 | 43 |
| serum miR-21 ≤0.0013 (cutoff) | 10 | 43 | 53 |
| Total | 43 | 53 | 96 |
| PPV (%) | 76.7 | Sensitivity (%) | 76.7 |
| NPV (%) | 81.1 | Specificity (%) | 81.1 |

To validate the accuracy estimates of ROC curves and optimal cut-off values for discriminating patients with colorectal adenoma or cancer from healthy controls, an internal validation was performed by BCa bootstrap methods. The results obtained with the original and the BCa bootstrap samples were in good agreement (Table 18 & 19). With serum miR-21 at 0.0013 (95% CI: 0.0009-0.00134), the sensitivity and specificity was 91.9% and 81.1% respectively to identify a patient with CRC, and 81.13% and 76.74% for a patient with colorectal adenoma using a cutoff value of 0.0013 (95% CI: 0.0010-0.00134) (Table 19).

TABLE 19

Sensitivity and Specificity after ROC analysis using Bootstrap Methods*

| CRC vs. Controls | | | | Adenoma vs. Controls | | | |
|---|---|---|---|---|---|---|---|
| Sensitivity | Specificity | optimal cutoff | 95% CI | Sensitivity | Specificity | optimal cutoff | 95% CI |
| 91.94 | 81.13 | >0.0013 | 0.0009-0.00134 | 81.13 | 76.74 | >0.0013 | 0.0010-0.00134 |
| Estimated specificity at fixed sensitivity | | | | Estimated specificity at fixed sensitivity | | | |
| Specificity | Sensitivity | 95% CI | cutoff | Specificity | Sensitivity | 95% CI | cutoff |
| 80 | 92.45 | 79.25-98.11 | >0.002 | 80 | 58.49 | 15.03-84.91 | >0.0012 |
| 90 | 83.02 | 50.94-92.45 | >0.0015 | 90 | 35.85 | 5.66-64.15 | >0.0009 |
| 95 | 45.28 | 19.27-73.58 | >0.001 | 95 | 15.09 | 0.53-52.83 | >0.0006 |
| 97.5 | 24.53 | 3.53-45.28 | >0.0007 | 97.5 | 9.43 | 0.87-35.85 | >0.0004 |
| 80 | 91.94 | 84.41-96.39 | >0.0013 | 80 | 76.74 | 58.14-90.70 | >0.0013 |
| 90 | 82.8 | 68.82-92.47 | >0.0019 | 90 | 60.47 | 25.58-76.74 | >0.0019 |
| 95 | 73.66 | 57.23-84.41 | >0.0026 | 95 | 34.88 | 13.54-65.12 | >0.0026 |
| 97.5 | 64.15 | 53.83-79.57 | >0.0033 | 97.5 | 25.58 | 7.24-51.16 | >0.0032 |

CI: Confidence Interval
*Bootstrap bias-correction and accelerated bootstrap methods used. Repeating times: 1000

ROCCH curves with BCa bootstrap bias-correction data in both CRC vs. controls and adenoma vs. controls were very similar to those without bias-correction (FIGS. 14D and 14E). In addition, AUC values obtained from ROCCH analysis from the original and bootstrap bias-corrected samples for identifying a patient with CRC were statistically non-significant (original AUC=0.935 (95% CI: 0.812-0.982) and BCa connected AUC=0.919 (95% CI: 0.867-0.958) P=0.80; Table 20). In a similar manner, no significant differences in ROCCH-derived AUC values for discriminating between two samples with colorectal adenomas (original AUC=0.838 (95% CI: 0.619-0.964) and BCa bootstrap AUC=0.813 (95% CI: 0.691-0.910) P=0.84; Table 20).

TABLE 20

Comparison between ROCCH and adjusted ROCCH by Bootstrap Methods*

| | | AUC | SE | 95% CI | P-value |
|---|---|---|---|---|---|
| CRC vs. Controls | ROCCH | 0.935 | 0.06 | 0.812-0.982 | 0.80 ** |
| | adjusted* ROCCH | 0.919 | 0.02 | 0.867-0.958 | |
| Adenoma vs. Controls | ROCCH | 0.838 | 0.11 | 0.619-0.964 | 0.84 ** |
| | adjusted* ROCCH | 0.813 | 0.06 | 0.691-0.910 | |

CRC: Colorectal Cancer;
ROCCH: Receiver Operating Characteristic Convex Hull;
AUC: Area under the ROC curve;
SE: Standard Error
CI: Confidence Intervals
*Bootstrap bias-correction and accelerated bootstrap methods used for adjusting. Repeating times: 1000
** A two-sided z-test was used to compare the AUCs of two ROC curves In addition, multivariate logistic regression analyses revealed that serum miR-21 could be used as a potential diagnostic biomarker for the identification of patients with CRC or adenomas after adjusted for patients' age and gender (P<0.0001 and P=0.0001, respectively; Table 21). The ORs for patients with serum miR-21 was 43.3 (95% CI: 17.53-107.13), and for cases with adenomas was 6.62 (95% CI: 2.63-16.88; Table 21).

TABLE 21

Multivariate logistic analyses for serum miR-21 levels and various diagnostic factors in patients with CRC and adenomas diagnostic factors in patients with CRC and adenomas

| Variables | OR | 95% CI | P-value |
|---|---|---|---|
| CRC vs. Controls | | | |
| Age (>67 vs. ≤67) ** | 1.69 | 0.73-3.92 | 0.22 |
| Gender (female vs. male) | 1.81 | 0.78-4.22 | 0.17 |
| miR-21 in serum (>0.0019 vs. ≤0.0019)† | 43.3 | 17.53-107.13 | 0.0001* |
| Adenoma vs. Controls | | | |
| Age (>67 vs. ≤67) ** | 0.54 | 0.21-1.39 | 0.2 |
| Gender (female vs. male) | 1.32 | 0.53-3.34 | 0.55 |
| miR-21 in serum (>0.0013 vs. ≤0.0013)† | 6.62 | 2.63-16.88 | 0.0001* |

CRC: colorectal cancer; OR: Odds ratio;
CI: Confidence Interval
*P < 0.05;
** Median age (year) is 67.
†The cutoff values of serum miR-21 in CRC vs. Controls and Adenoma vs. Controls are derived by ROC curves with Youden's index.

Correlation Between Serum and Tissue miR-21 Expression in CRC Patients—

Figures 15A, 15B:
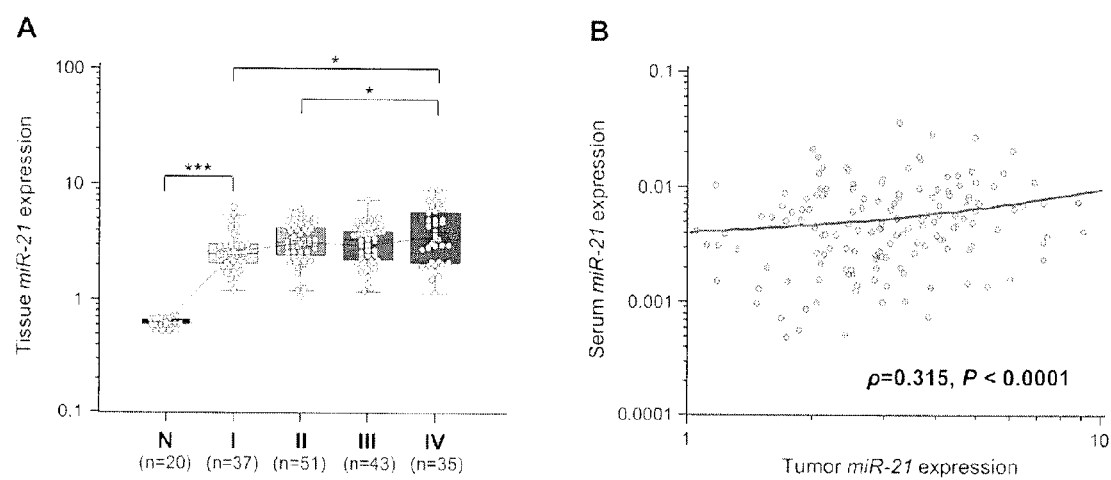
FIGS. 15A-15B—Validation of miR-21 expression in matched tissue samples (n=186). (A) Box plots illustrating tissue miR-21 levels in different TNM stages (I, II, III and IV) of CRCs (n=166) and adjacent normal mucosa (N; n=20). Y-axis (log 10 scale) represents relative expression of miR-21 normalized to miR-16 in tissue samples. Boxes represent the interquartile range and the horizontal line across each box indicates median value. Statistically significant differences were determined using the Mann-Whitney U test and Kruskal-Wallis tests. *, P<0.05; ***, P<0.0001. (B) Scatter plots showing the correlation between relative expression of miR-21 levels in serum (Y-axis: log 10 scale) and matched tumor tissues (X-axis: log 10 scale) obtained from 154 CRC patients. Positive correlation was found by Spearman correlation; p=0.315 (95% CI: 0.17-0.45; P<0.0001).

Next, Table 22 illustrates that miR-21 levels in both tumor tissues and matched serum were significantly higher in CRC patients with larger tumor size (P=0.014 and P=0.004, respectively) and those with distant metastases (P=0.02 and P=0.01, respectively). Tissue levels of miR-21 expression correlated with CRC clinical stage (stage I vs. IV, P<0.05; stage II vs. IV, P<0.05; FIG. 15A). However, miR-21 levels in both tumor tissues and matched serum samples did not correlate with specific tumor location within the colorectum.

TABLE 22

Clinical significance of miR-21 expression in serum and tissue specimens from CRC patients specimens from CRC patients

| Variables | | Serum miR-21 expression mean ± SD (n = 186) | P-value | Tissue miR-21 expression mean ± SD (n = 166) | P-value |
|---|---|---|---|---|---|
| Age** | ≤67 | 0.0062 ± 0.0047 (n = 88) | 0.22 | 3.16 ± 1.46 (n = 80) | 0.07 |
| | >67 | 0.0059 ± 0.0052 (n = 98) | | 3.64 ± 1.73 (n = 86) | |
| Gender | Male | 0.0059 ± 0.0053 (n = 106) | 0.30 | 3.23 ± 1.46 (n = 100) | 0.36 |
| | Female | 0.0062 ± 0.0044 (n = 80) | | 3.52 ± 1.72 (n = 66) | |
| Tumor location | Right side | 0.0073 ± 0.0065 (n = 59) | 0.16 | 3.38 ± 1.45 (n = 56) | 0.70 |
| | Left side | 0.0058 ± 0.0048 (n = 127) | | 3.33 ± 1.57 (n = 110) | |
| Tumor type | Colon cancer | 0.0063 ± 0.0055 (n = 110) | 0.89 | 3.50 ± 1.51 (n = 101) | 0.07 |
| | Rectal cancer | 0.0062 ± 0.0054 (n = 76) | | 3.11 ± 1.52 (n = 65) | |
| Tumor size** | ≤5 | 0.0048 ± 0.0035 (n = 91) | 0.004* | 3.13 ± 1.47 (n = 78) | 0.014* |
| | >5 | 0.0070 ± 0.0056 (n = 95) | | 3.67 ± 1.71 (n = 88) | |
| Serosal Invasion | negative | 0.0051 ± 0.0041 (n = 58) | 0.08 | 2.82 ± 1.37 (n = 47) | 0.004* |
| | positive | 0.0064 ± 0.0052 (n = 128) | | 3.64 ± 1.66 (n = 119) | |
| Lymphatic Invasion | negative | 0.0058 ± 0.0041 (n = 46) | 0.83 | 3.04 ± 1.52 (n = 39) | 0.02* |
| | positive | 0.0061 ± 0.0051 (n = 140) | | 3.53 ± 1.64 (n = 127) | |
| Venous Invasion | negative | 0.0058 ± 0.0045 (n = 108) | 0.53 | 3.36 ± 1.53 (n = 91) | 0.6 |
| | positive | 0.0064 ± 0.0054 (n = 78) | | 3.47 ± 1.73 (n = 75) | |
| Lymph node metastasis | negative | 0.0055 ± 0.0042 (n = 106) | 0.12 | 3.24 ± 1.48 (n = 92) | 0.11 |
| | positive | 0.0068 ± 0.0057 (n = 80) | | 3.62 ± 1.76 (n = 74) | |
| Distant Metastasis | negative | 0.0055 ± 0.0045 (n = 45) | 0.01* | 3.21 ± 1.37 (n = 131) | 0.02* |
| | positive | 0.0078 ± 0.0060 (n = 41) | | 4.18 ± 2.19 (n = 35) | |

CRC: colorectal cancer;
SD: Standard Deviation
*P < 0.05;
**The median age and tumor size are 67 (years) and 5 (cm), respectively.

To further enhance the specificity of the assay and validate that circulating miR-21 expression accurately reflects concentrations found in CRC tissues, the relationship between miR-21 levels was determined in primary CRC tissues and matched serum from individual CRC patients. Interestingly, a significantly positive correlation between miR-21 expression was observed in primary CRC lesions and matched serum samples from these patients (p=0.315; 95% CI: 0.17-0.45; P<0.0001; Spearman's correlation analysis; FIG. 15B).

Figures 16A, 16B, 16C:
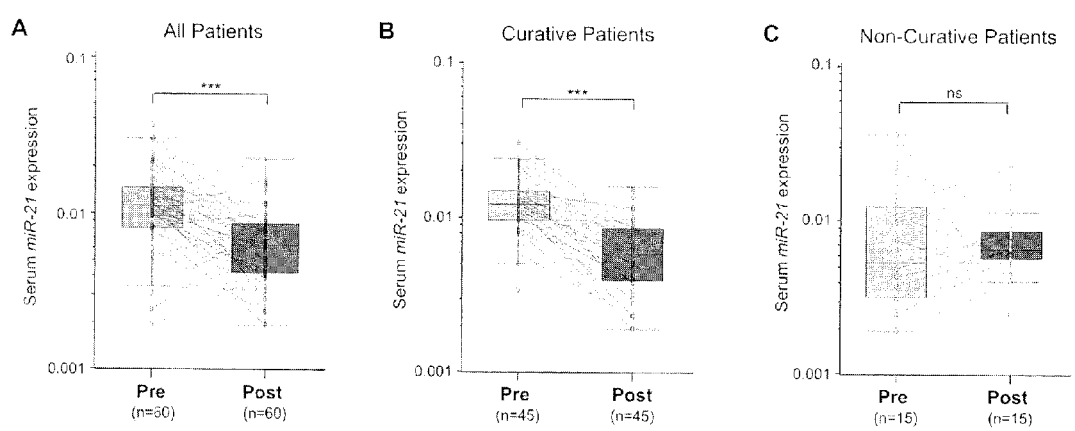
FIGS. 16A-16C—Alterations in serum miR-21 expression levels in patients with CRC before surgery (Pre), and 7 days after post-surgical removal of primary tumors (Post). (A) Comparison of serum miR-21 levels from all CRC patients (n=60). (B) Comparison of serum miR-21 levels in 45 CRC patients who underwent potentially curative surgeries. (C) Comparison of serum miR-21 levels in 15 CRC patients with non-curative surgeries. Y-axis (log 10 scale) represents relative expression of miR-21 normalized to cel-miR-39. Boxes represent the interquartile range and the horizontal line across each box indicates the median value. Statistically significant differences were determined using the Wilcoxon test. ***, P<0.0001; ns, not significant.

Thereafter, paired pre- and post-operative serum samples were analyzed in a subset of 60 CRC who underwent surgical resection of their tumors. In the 60 CRC patients, 45 underwent potentially curative resection, while 15 had multiple hepatic metastases and underwent primary resection to prevent bleeding and bowel obstruction (non-curative resection). It was interesting to note that serum levels of miR-21 significantly plummeted following surgery in the same subset of patients (P<0.0001; FIG. 16A). Furthermore, when data were analyzed based on potentially curative versus non-curative surgeries, post-operative reductions in serum miR-21 levels occurred exclusively among patients with potentially curative surgeries (P<0.0001; FIG. 16B). Contrariwise, no significant differences were observed in miR-21 levels before or after surgery in patients with non-curative resections (P=0.72; FIG. 16C). Collectively, these data underscore the importance of serum miR-21 expression as a highly specific biomarker for the diagnosis of colorectal neoplasia.

Association of Serum miR-21 Expression with Survival in Patients with CRC—

Figures 17A, 17B:
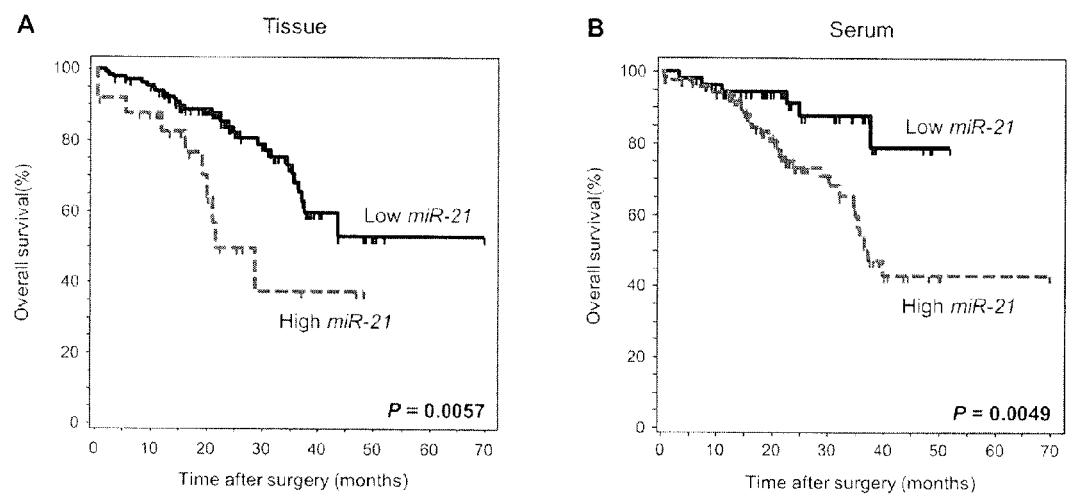
FIGS. 17A-17B—Kaplan-Meier survival analysis in CRC patients based upon miR-21 expression in primary tumors and mate/zed serum samples. (A) The overall survival rate in CRC patients with high miR-21 expression in tumor tissue (n=25) was significantly lower than for those with low miR-21 expression (n=141) (>3.7 vs. <3.7; P=0.0057; log-rank test). (B) The overall survival rate in CRC patients with high serum miR-21 expression (n=126) was significantly lower than for those with low serum miR-21 expression (n=62) (>0.0031 vs. <0.0031; P=0.0049; log-rank test). Cut-off values for miR-21 expression in serum and primary tumor tissues were determined from the ROC curves by using Youden's Index.

To further evaluate whether serum miR-21 levels can serve as a predictor of patient outcome, Kaplan-Meier survival analysis was performed. As anticipated, patients with higher levels of miR-21 in the tumor tissues had significantly worse overall survival (P=0.0057; log-rank test; FIG. 17A). Moreover, similar pattern of increased miR-21 concentrations associated with significantly decreased overall survival was observed when the analysis utilized serum miR-21 expression levels (P=0.0049; log-rank test; FIG. 17B).

Furthermore, Cox proportional hazard regression analyses revealed that in the univariate analysis, poor prognosis in CRC patients was associated with high levels of miR-21 in both tumor and serum (P=0.014 and P=0.0026, respectively), high levels of carcinoembryonic antigen (CEA>5 ng/mL, P=0.0001), high T stage (T3/T4, P=0.0024), lymph node metastasis (P<0.0001), poorly differentiated tumors (P=0.036) and distant metastasis (P<0.0001; Table 23). More importantly, multivariate analysis demonstrated that high levels of serum miR-21, but not high concentrations of miR-21 in tumor tissues or high CEA levels, served as an independent prognostic marker for indicating overall survival in CRC patients (HR=4.12; 95% CI=1.10-15.4; P=0.03).

specimens (n=20) and their corresponding liver metastasis tissues (n=20) were analyzed during this step of the study.

Patients treated with radiotherapy or chemotherapy prior to surgery were not included in this study. Patients with stage III and IV disease received 5-fluorouracil-based chemotherapy, whereas no adjuvant therapy was given to stage I and II CRC patients. CEA levels in serum samples were measured by standard enzyme immunoassay as a routine clinical test. Both serum- and tissue-based studies were approved by the Institutional Review Broad (IRB) of the Mie University Hospital, Japan and Baylor University Medical Center, Dallas, USA. All participants gave written consent for their information to be stored in the hospital database and used for research.

TABLE 23

Uni- and multivariate analyses of factors predictive of poor overall survival in CRC patients

| Variables | Univariate[#] | | | Multivariate[##] | | |
|---|---|---|---|---|---|---|
| | HR | 95% CI | P-value | HR | 95% CI | P-value |
| Age (>67 vs. ≤67)** | 0.72 | 0.43-1.37 | 0.37 | 1.23 | 0.57-2.67 | 0.59 |
| Gender (female vs. male) | 1.02 | 0.56-1.86 | 0.92 | 2.07 | 1.86-4.96 | 0.1 |
| Pathological T (T3/4 vs. T1/2) | 8.97 | 2.19-36.7 | 0.0024* | 2.38 | 0.3-29.77 | 0.31 |
| Pathology (poor diff. vs. diff.) | 2.26 | 1.05-4.84 | 0.036* | 2.39 | 0.57-9.92 | 0.23 |
| Lymph node metastasis (yes vs. no) | 17.1 | 6.18-47.8 | <0.0001* | 6.83 | 1.69-28.36 | 0.008* |
| Distant metastasis (yes vs. no) | 35.6 | 14.4-86.6 | <0.0001* | 21.7 | 5.92-79.99 | <0.0001* |
| CEA (>5 vs. ≤5)† | 4.84 | 2.15-10.89 | 0.001* | 1.03 | 0.33-3.22 | 0.94 |
| miR-21 in tissue (>3.7 vs. ≤3.7)† | 2.66 | 1.29-5.45 | 0.014* | 0.59 | 0.21-1.63 | 0.31 |
| miR-21 in serum (>0.0031 vs. ≤0.0031)† | 3.25 | 1.36-7.73 | 0.0026* | 4.12 | 1.1-15.4 | 0.03* |

CRC: colorectal cancer;
HR: Hazard Ratio;
CI: Confidence Interval;
CEA: Carcinoembryonic antigen;
diff: differentiation,
*P < 0.05.
**The median age (year) is 67.
†Cut-off values for CEA is 5 (as per American Association of Clinical Oncology recommendations). Cut-off values of miR-21 in tissue and serum are derived from ROC curve with Youden's index.
[#]Univariate analysis was performed using clinical data available from 200 patients, serum miR-21 data from 186 patients and tissue miR-21 data from 166 CRC patients, respectively.
[##]Multivariate analysis was performed using data from 153 CRC patients from whom matched matching data were available for all clinico-pathological factors as well as serum and tissue miR-21 expression results.

Example 4—Serum miR-200c is a Novel Prognostic and Metastasis-Predictive Biomarker in Patients with Colorectal Cancer Methods Study Design and Clinical Specimens—

This study included analysis of 446 colorectal specimens that which were obtained at Mie University Medical Hospital, Mie prefecture in Japan between 2005 and 2011. This was a three phase study, which aimed to screen, validate, and determine the potential contribution of serum miRNAs in CRC patients.

During the initial screening phase, serum levels of several candidate miR-200 family were analyzed in a subset of 24 serum samples from stage I (n=12) and stage IV (n=12) CRC patients. In the second phase, candidate miRNAs that were overexpressed in serum of stage IV vs. stage I patients in the initial screening step were further validated in a larger, independent cohort, which included serum samples from 182 CRC patients and 24 normal controls. The final phase aimed to evaluate the potential source of miRNAs in the serum in CRC patients by comparing expression of selected miRNAs in matched surgical FFPE tissues (n=156) from 182 CRC patients and 20 adjacent normal mucosa. In addition, an independent set of matched primary CRC RNA Isolation from Serum and qRT-PCR—

Small RNAs were enriched from all serum samples using the Qiagen miRNAeasy Kit (Qiagen, Valencia, Calif.). Briefly, 250 µL of serum was thawed on ice and centrifuged at 10,000 rpm for 5 minutes to remove cellular debris. Next, 200 µL of supernatant was lysed with five volumes of Qiazol solution. For normalization of sample-to-sample variation during the RNA isolation procedures, 25 fmol of synthetic C. elegans miRNA (cel-miR-39) was added to each denatured sample. Small RNAs were then enriched and purified according to the manufacturer's protocol, with the exception that the enriched small RNAs were eluted in 40 µL of preheated nuclease-free water. For miRNA-based RT-PCR assays, 1.67 µL of enriched small RNAs from serum samples were reverse-transcribed using the TaqMan MicroRNA Reverse Transcription Kit (Applied Biosystems, San Diego, Calif.) in a total reaction volume of 5.0 µL, according to the manufacturer's instructions. RT products were diluted 1:15 and used as PCR template. PCR reactions for quantification of miR-200b, miR-200c, miR-141, miR-429 and cel-miR-39 were performed in duplicate using TaqMan 2× Universal PCR Master Mix using conditions described previously (Kroh 2010). The qRT-PCR reactions were performed using an Applied Biosystems 7000 Sequence Detection System with the following cycling conditions: 95° C. for 10 min, followed by 45 cycles of 95° C. for 15 s and 60° C. for 1 min.

The cycle threshold (Ct) values were calculated with SDS 1.4 software (Applied Biosystems, Foster City, Calif.).

RNA Isolation from FFPE Tissues and qRT-PCR—

Total RNA was isolated from FFPE samples using the RecoverAll Total Nucleic Acid Isolation Kit (Ambion Inc., Austin, Tex., USA). Briefly, tissue sections were microdissected to enrich for neoplastic cells, followed by deparaffinization and RNA extraction using the manufacturer's protocol. Total RNA was eluted in appropriate buffer, and quantified using a NanoDrop spectrophotometer (NanoDrop Technologies, Wilmington, Del.). Reverse transcription reactions were carried out using the TaqMan MicroRNA Reverse Transcription Kit (Applied Biosystems, San Diego, Calif.) in a total reaction volume of 15 pt. MiR-200c and miR-16 were quantified in duplicate by qRT-PCR, using TaqMan MicroRNA Assay Kits (Applied Biosystems, Foster City, Calif.). qRT-PCR was performed on an Applied Biosystems 7000 Sequence Detection System using the following cycling conditions: 95° C. for 10 min, followed by 45 cycles of 95° C. for 15 s and 60° C. for 1 min. Cycle threshold (Ct) values were calculated with SDS 1.4 software (Applied Biosystems, Foster City, Calif.).

Calculation of miRNA Expression—

The average expression levels of serum and tissue miRNAs were normalized against cel-miR-39 (Mitchel 2008; Kroh 2010) and miR-16 (Link 2010; Chang 2010) using the $2^{-\Delta Ct}$ method. Differences between the groups are presented as ΔCt, indicating the difference between the Ct value of the miRNA of interest and the Ct value of the normalizer miRNA. To ensure consistent measurements throughout all assays, for each PCR amplification reaction, three independent RNA samples were loaded as internal controls to account for any plate to plate variation, and the results from each plate were normalized against internal normalization controls.

In Situ Hybridization—

Five micrometer-thick FFPE tissue sections were hybridized with the miR-200c probe (LNA-modified and 5'- and 3'-DIG-labeled oligonucleotide; Exiqon, Woburn, Mass., USA), followed by incubation with anti-DIG-AP Fab fragments conjugated to alkaline phosphatase, and the hybridization signal was detected by applying nitroblue tetrazolium/5-bromo-4-chloro-3-indolyl phosphate color substrate (Roche Applied Science, Mannheim, Germany). Positive controls (U6 snRNA, LNA-modified and 5'- and 3'-DIG-labeled Oligonucleotide; Exiqon) and negative controls (scrambled microRNA control, LNA-modified and 5'- and 3'-DIG-labeled oligonucleotide; Exiqon) were included in each hybridization procedure.

Statistical Analysis—

The significance of serum and tissue miRNA levels was determined by the Mann-Whitney test, Kruskal-Wallis test or the χ2 test where appropriate. Logistic regression analysis was used to predict the factors influencing lymph node metastasis. Overall and disease free survival curves were analyzed using the Kaplan-Meier method, and differences were examined using Log-rank tests. Cox's proportional hazard regression test was used to estimate univariate and multivariate hazard ratios for recurrence and prognosis. Receiver operating characteristic (ROC) curves with Youden's Index connection (Kuopp 2008) were established for determining optimal miRNA expression cut-off thresholds for analyzing lymph node metastasis prediction, disease free survival and overall survival. All P values were two-sided, and those less than 0.05 were considered statistically significant. All statistical analyses were carried out using Medcalc 7.2 for Windows (Broekstraat 52, 9030, Mariakerke, Belgium).

Results

Serum miR-200c is a Candidate miRNA that is Associated with CRC Metastasis—

Figures 18A, 18B, 18C, 18D:
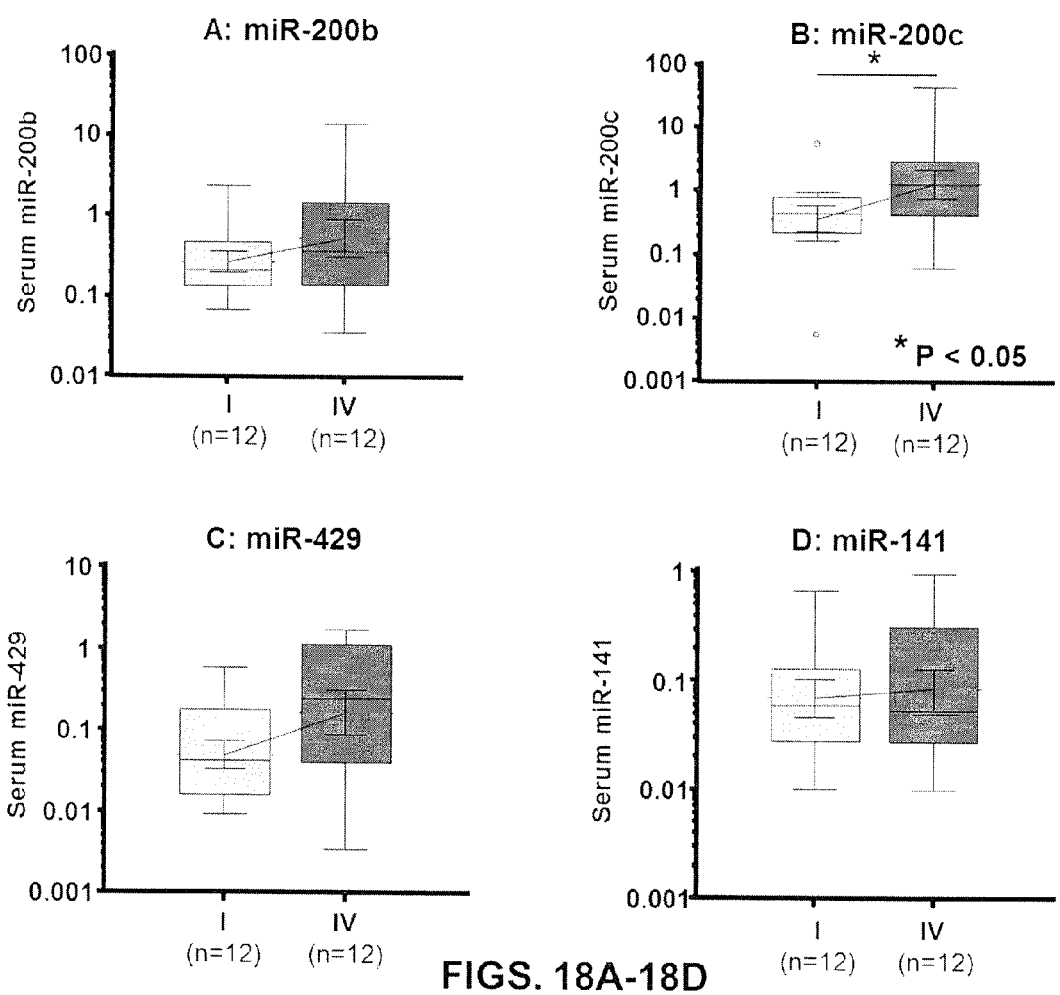
FIGS. 18A-18D—Expression analysis of miR-200 family members in the serum of stage I and stage IV CRC patients. Box plots of serum levels of miR-200b (A), miR-200c (B), miR-429 (C) and miR-141 (D) in stage I (n=12) and stage IV (n=12) CRC patients. MiR-200c levels in serum from stage IV patients were significantly higher than that of stage I patients. The boxes represent the interquartile range, and the lines across the boxes indicate the median values. Expression levels of these miRNAs (log 10 scale on the y-axis) were normalized to cel-miR-39. Statistical analysis was performed using Mann-Whitney test.

In the initial screening step aimed at identifying metastasis-associated serum miRNA biomarkers as noninvasive prognostic markers, the relative expression levels of miR-200 family (miR-200b, miR-200c, miR-141 and miR-429) was investigated in a subset of serum specimens from 12 stage IV and 12 stage I CRC patients (Table 24). Among all miRNA analyzed (FIG. 18), miR-200c was significantly elevated in the serum of stage IV patients compared to stage I CRC patients (P<0.05; FIG. 18B). In contrast, no significant differences were observed in miR-141, miR-200b and miR-429 expression between stage I and stage IV CRC patients (FIGS. 18A, 18C and 18D). Based upon these observations, subsequent experiments focused on validating and further exploring the clinical significance of miR-200c in an independent set of serum samples from 182 CRC patients. In addition, the potential origin of miR-200c in serum was investigated by analyzing matched serum and tumor tissues samples from patients who had—matched primary tissues from 182 CRC patients and an independent set of tissues from 20 pairs of primary CRCs and matched liver metastases.

TABLE 24

Patient characteristics in the initial screening set

| Age | Gender | Pathology | T stage | N stage | M stage | Liver Metastasis | TNM stage |
|---|---|---|---|---|---|---|---|
| 57 | M | well | 2 | n0 | M0 | H0 | stage I |
| 62 | M | well | 2 | n0 | M0 | H0 | stage I |
| 51 | F | well | 1 | n0 | M0 | H0 | stage I |
| 73 | M | well | 2 | n0 | M0 | H0 | stage I |
| 69 | F | well | 1 | n0 | M0 | H0 | stage I |
| 72 | M | well | 1 | n0 | M0 | H0 | stage I |
| 47 | F | mod | 1 | n0 | M0 | H0 | stage I |
| 37 | F | well | 1 | n0 | M0 | H0 | stage I |
| 79 | F | well | 1 | n0 | M0 | H0 | stage I |
| 82 | M | mod | 2 | n0 | M0 | H0 | stage I |
| 76 | F | mod | 2 | n0 | M0 | H0 | stage I |
| 57 | F | well | 2 | n0 | M0 | H0 | stage I |
| 82 | F | mod | 4 | n1 | M1 | H1 | stage IV |
| 70 | M | mod | 3 | n1 | M1 | H2 | stage IV |
| 67 | M | mod | 3 | n2 | M1 | H2 | stage IV |
| 72 | F | mod | 3 | n2 | M1 | H3 | stage IV |
| 60 | M | mod | 3 | n1 | M1 | H3 | stage IV |
| 84 | M | mucinous | 2 | n1 | M1 | H2 | stage IV |
| 61 | M | mod | 3 | n1 | M1 | H3 | stage IV |
| 75 | M | poor | 3 | n1 | M1 | H3 | stage IV |
| 76 | M | mod | 3 | n1 | M1 | H1 | stage IV |
| 62 | M | mod | 4 | n2 | M1 | H3 | stage IV |
| 71 | M | well | 3 | n0 | M1 | H1 | stage IV |
| 61 | F | well | 4 | n2 | M1 | H1 | stage IV |

Well, well differentiated;
mod, moderately differentiated;
poor, poorly differentiated Serum miR-200c Expression Levels Serve as a Predictive and Prognostic Biomarker in CRC Patients—

Patient characteristics and distribution of tumor stages are summarized. There were no significant differences in the mean age between CRC patients (67±10.4 years) and healthy controls (64±12.9 years; P>0.05; ANOVA). The gender distribution in the CRC group was 105:77 (males:

females), and in the control group it was 13:11 (P>0.05; Chi-square test). For miR-200c expression analysis in matched primary CRCs tissues and serum, 156 of 182 samples were available from the CRC patient cohort.

Serum miR-200c Levels Predict Lymph Node Metastasis in Patients with CRC—

Figures 19A, 19B, 19C, 19D:
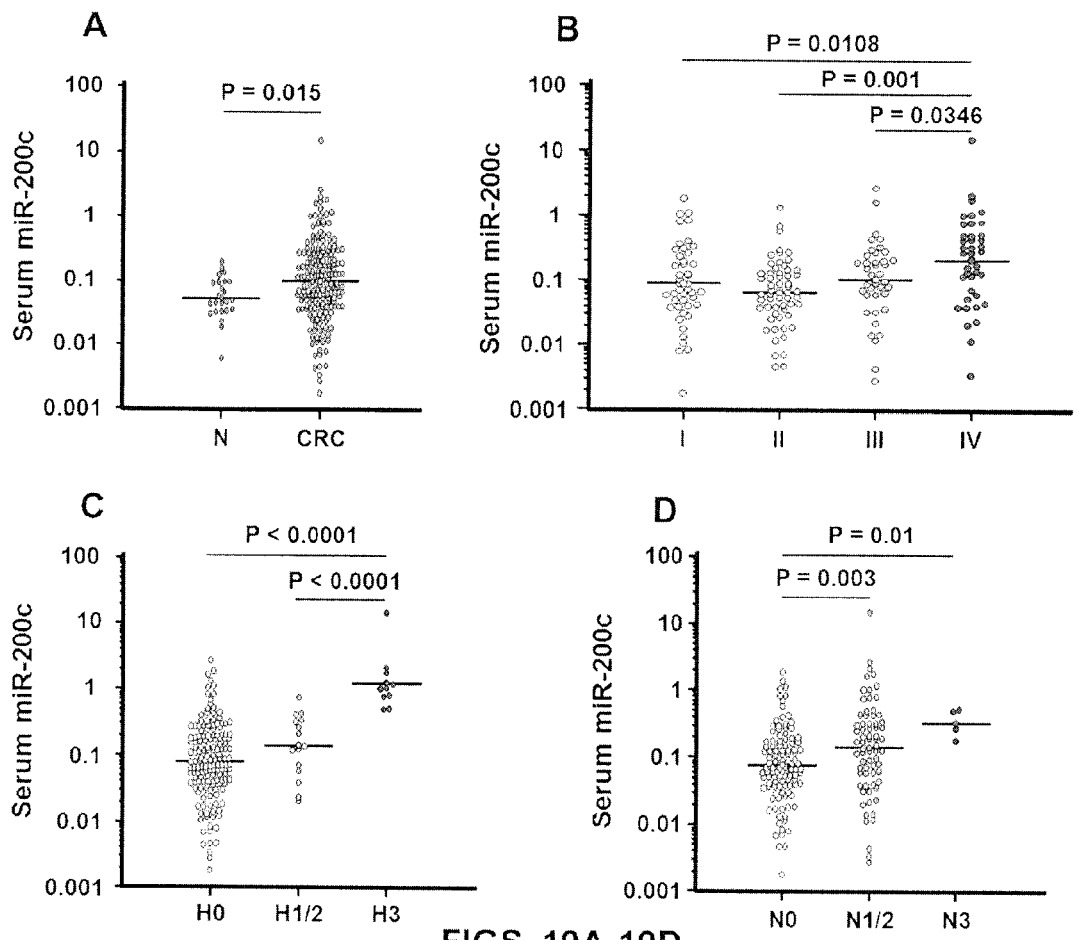
FIGS. 19A-19D—Validation of miR-200c expression in a validation cohort of CRC patients. (A) Dot plots of serum miR-200c levels in healthy normal controls (NC) (n=24) and patients with CRC (n=182). (B) Dot plots of serum miR-200c levels across various stages of CRCs. MiR-200c levels in serum from CRC patients were significantly elevated compared with those of normal controls, and the expression levels in stage IV CRC patients were significantly higher than those in stage I-III patients. (C) Dot plots of serum miR-200c levels subdivided by H Stage. (D) Dot plots of serum miR-200c levels subdivided by N Stage. Serum miR-200c increased depending on the higher N and H stages. The lines indicate the mean values. Expression levels of miR-200c (log 10 scale on the y-axis) were normalized to cel-miR-39. Statistically significant differences were determined using Mann-Whitney tests and Kruskal-Wallis test.
Figure 22A:
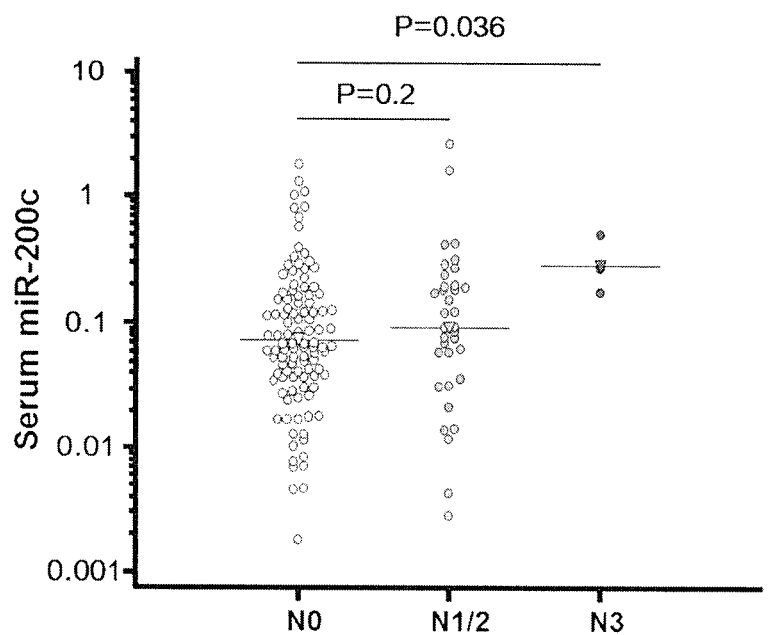
FIGS. 22A-22B—Serum miR-200c expression based upon N stage in curative patients. (A) Dot plots of serum miR-200c levels based upon N Stage in stage I-III CRC patients. (B) Dot plots of serum miR-200c levels subdivided by N Stage in stage II+III CRC patients. The lines indicate the mean values. Expression levels of miR-200c (log 10 scale on the y-axis) were normalized to cel-miR-39. Statistically significant differences were determined using Mann-Whitney tests and Kruskal-Wallis test.
Figure 22B:
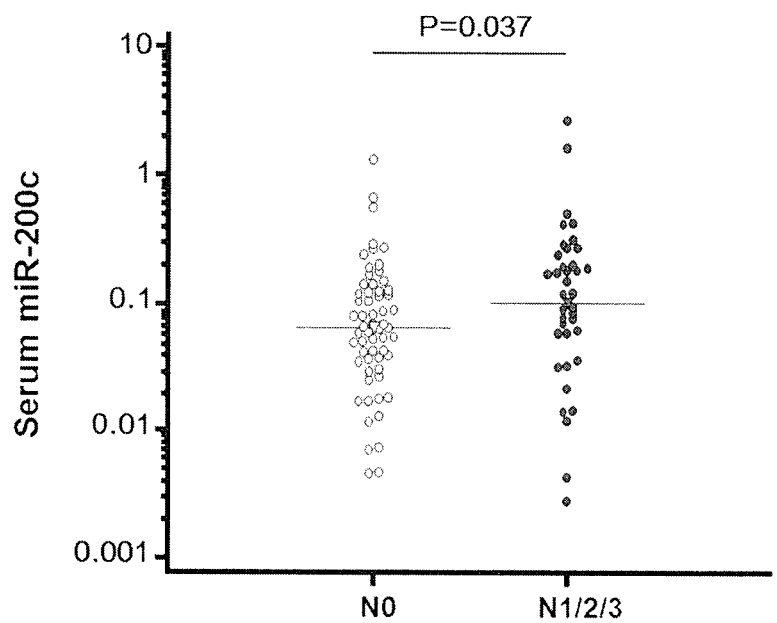

The expression levels of serum miR-200c in CRC were significantly higher compared to that in normal controls (P=0.015; FIG. 19A). Serum miR-200c levels were significantly higher in stage IV patients than in normal controls, and stage I, II and III CRC patients (FIG. 19B). The potential clinical significance of serum miR-200c expression is presented in Table 25. As shown, high expression of serum miR-200c was associated with a metastatic phenotype, including lymph node metastasis (P=0.0026), liver metastasis (P=0.0015) and the development of distant metastases (P=0.0023) in CRC patients.

serum expression of miR-200c was significantly higher in patients with lymph node metastasis to the aorta (n3) compared with regional (n1-2: P=0.003; FIG. 19D) or absent lymph node metastasis (n0: P=0.01; FIG. 19D) in CRC patients. Additionally in stage I-III patients, serum miR-200c expression increased in accordance with progression of lymph node metastasis, and miR-200c expression in N3 patients was significantly higher than that in N0 patients (P=0.036; FIG. 22A). Furthermore, serum miR-200c expression of lymph node-positive patients was significantly higher than that of node-negative patients in stage II and III CRC patients (P=0.037; FIG. 22B). Taken together, these results indicate that serum miR-200c levels in CRC could be influenced by tumor volume or its dissemination to lymph node or hepatic metastatic sites.

To further evaluate whether serum miR-200c levels can serve as a predictor of lymph node metastasis, logistic

TABLE 25

Association between miR-200c expression in serum and primary CRC and various clinicopathological characteristics

| Factors | | Serum miR-200c (n = 182) | | | Tissue miR-200c (n = 156) | | |
|---|---|---|---|---|---|---|---|
| | | high (n = 91) | low (n = 91) | P-value | high (n = 78) | low (n = 78) | P-value |
| Age | ≤68 | 43 | 43 | 0.88 | 31 | 43 | 0.078 |
| | >68 | 48 | 48 | | 47 | 35 | |
| Gender | Male | 49 | 56 | 0.36 | 41 | 48 | 0.29 |
| | Female | 42 | 35 | | 37 | 30 | |
| Histological grade | well/mod | 83 | 82 | 0.99 | 69 | 71 | 0.79 |
| | poor/mucinous | 8 | 9 | | 9 | 7 | |
| Tumor size | ≤40 (small) | 47 | 42 | 0.50 | 38 | 40 | 0.87 |
| | >40 (large) | 44 | 49 | | 40 | 38 | |
| Serosal invasion | Absent | 26 | 29 | 0.78 | 27 | 18 | 0.12 |
| | Present | 65 | 62 | | 51 | 60 | |
| Lymph node met. | Absent | 43 | 64 | 0.0026 | 49 | 38 | 0.10 |
| | Present | 48 | 27 | | 29 | 40 | |
| Venous invasion | Absent | 52 | 53 | 0.99 | 49 | 38 | 0.10 |
| | Present | 39 | 38 | | 29 | 40 | |
| Lymphatic invasion | Absent | 20 | 26 | 0.39 | 26 | 10 | 0.0044 |
| | Present | 71 | 65 | | 52 | 68 | |
| Liver metastasis | Absent | 70 | 86 | 0.0015 | 71 | 67 | 0.45 |
| | Present | 21 | 5 | | 7 | 11 | |
| Peritoneal metastasis | Absent | 83 | 88 | 0.21 | 76 | 70 | 0.10 |
| | Present | 8 | 3 | | 2 | 8 | |
| Distant metastasis | Absent | 62 | 80 | 0.0023 | 68 | 59 | 0.099 |
| | Present | 29 | 11 | | 10 | 19 | | well, well differentiated;
mod, moderately differentiated;
poor, poorly differentiated miR-200c levels were analyzed in serum based upon pathological extension of colorectal neoplasia to hepatic or lymph node metastasis. Associations between miR-200c expression and the H-classification of CRCs were determined; with 1-10 indicating no liver metastasis; H1 representing liver metastasis with less than five nodules smaller than 5 cm; H2 indicative of metastasis that does not involve H1 and H3; and H3 indicating liver metastasis with more than five metastasis larger than 5 cm. The miR-200c levels were significantly higher in H3CRC patients than those in H0 or H1-2 CRC patients (P<0.0001; FIG. 19C). Likewise, regression analysis was performed. Univariate analysis demonstrated that highly invasive tumors (T3/4; P=0.0024), with lymphatic (P<0.0001) and venous invasion (P=0.0001), high CEA levels (P=0.0001) and high levels of serum miR-200c (P=0.0001) were all significantly associated with lymph node metastasis (Table 26). Furthermore, serum miR-200c expression was an independent predictor of lymph node metastasis in CRC based upon multivariate logistic regression analysis (HR=4.81, 95% CI=1.98-11.7 P=0.0005), suggesting that serum miR-200c as a predictor of lymph node metastasis is superior to pathological findings that are known to be risk factors.

TABLE 26

Uni-and multi-variate analyses for predicting lymph node metastasis in CRC patients

| Variables | Univariate | | | Multivariate | | |
|---|---|---|---|---|---|---|
| | HR$ | 95% CI | p-value | HR$ | 95% CI | p value |
| Pathological T stage (T3/4 vs. 1/2) | 6.46 | 2.61-59.96 | 0.0024 | 2.38 | 0.81-7.03 | 0.11 |
| Pathology (poor vs. mod/well differentiated) | 2 | 0.57-6.98 | 0.2715 | 1.39 | 0.38-5.07 | 0.62 |
| Venous Invasion (positive vs. negative) | 4.59 | 2.13-9.89 | 0.0001 | 1.24 | 0.52-2.96 | 0.62 |
| Lymphatic Invasion (positive vs. negative) | 18.26 | 5.43-61.38 | <0.0001 | 6.56 | 1.55-27.8 | 0.010 |
| CEA (≥5 vs. <5) | 6.25 | 2.45-15.92 | 0.0001 | 2.44 | 1.02-5.84 | 0.044 |
| miR-200c in serum (high vs. low) | 3.61 | 1.85-7.09 | 0.0001 | 4.81 | 1.98-11.7 | 0.0005 |

Serum miR-200c is a Prognostic and Tumor Recurrence Predictive Biomarker in CRC—

Figures 20A, 20B:
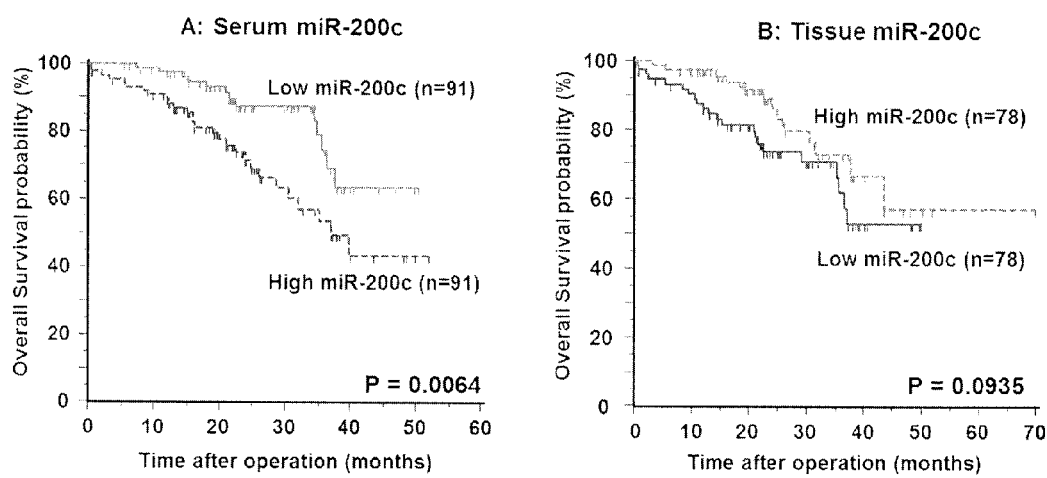
FIGS. 20A-20B—Kaplan-Meier survival curves of CRC patients subdivided by miR-200c levels in serum and matched primary tumors from CRC patients. (A) Overall survival rates of CRC patients with high serum miR-200c levels were significantly lower than for those with low miR-200c expression (P=0.0064; Log-rank test). (B) Overall survival rates of CRC patients with high miR-200c expression in primary CRC were lower than for those with low miR-200c expression (P=0.0935; Log-rank test). The miRNA expression cut-off thresholds for miR-200c expression in serum were deduced from the ROC curves with Youden's Index.
Figures 23A, 23B:
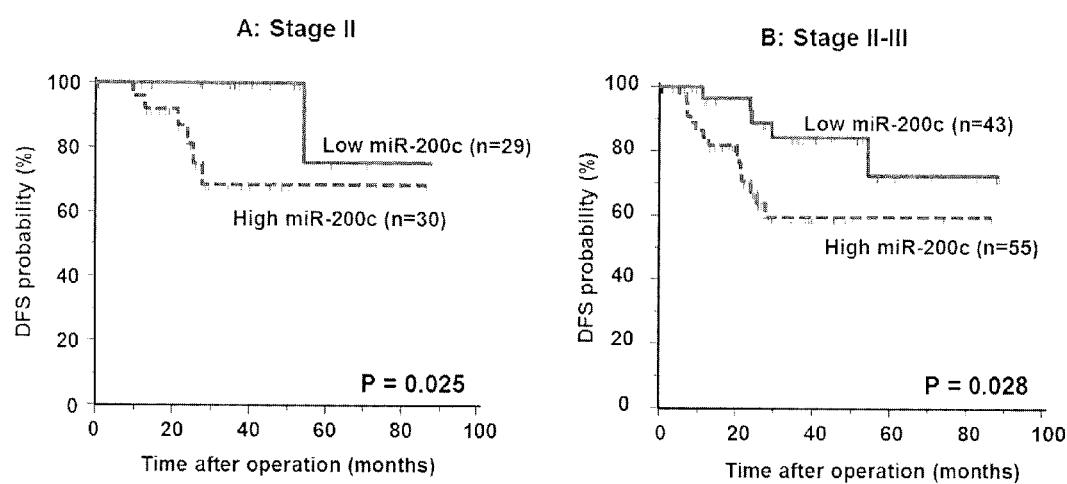
FIGS. 23A-23B—Serum miR-200c expression and Kaplan-Meier survival curves of CRC patients who underwent curative surgery. (A) Kaplan-Meier curves for disease free survival (DFS) in stage II CRC patients according to serum miR-200c expression (P=0.025; Log-rank test). (B) Kaplan-Meyer curves for DFS in stage II+III CRC patients according to serum miR-200c expression (P=0.028; Log-rank test). The cut-off values for miR-200c expression in serum were deduced from the ROC curves with Youden's Index.

To further evaluate whether serum miR-200c levels can predict CRC prognosis, survival analysis was performed. Kaplan-Meier analysis showed that patients with higher levels of serum miR-200c had significantly poorer survival than those with lower expression of this miRNA (P=0.0064, log-rank test; FIG. 20A). To determine whether serum miR-200c expression was an independent risk factor for prognosis, the Cox proportional hazard regression model was employed (Table 27). In univariate analysis, high levels of miR-200c in serum (P=0.006), high levels of CEA (P=0.0001), high pathological T stage (T3/4; P=0.0024), lymph node metastasis (P<0.0001), poor differentiation (P=0.036) and high TNM stage (stage III/IV; P<0.0001) were significantly associated with poor prognosis. On the other hand, multivariate analysis showed that high serum miR-200c expression was an independent prognostic marker for predicting poorer overall survival in CRC patients (HR=2.67, 95% CI=1.28-5.67 P=0.01; Table 27). In addition, patients with high serum miR-200c in stage II or stage II-III had shorter disease free survival than those with low serum miR-200c, respectively (P=0.025, log-rank test; FIG. 23A, P=0.028, log-rank test; FIG. 23B). To determine whether serum miR-200c can serve as a predictor for tumor recurrence in curative patients (stage II-III), Cox's proportional hazard regression model was utilized (Table 28). Univariate analysis showed that venous invasion (positive; P=0.038), lymph node metastasis (P=0.0015) and high serum miR-200c levels (P=0.024) were significantly associated with disease free survival. In contrast, multivariate analysis revealed that high serum miR-200c was an independent predictor for tumor recurrence in stage II-III CRC patients (HR=4.51, 95% CI=1.56-13.01 P=0.005). Therefore, serum miR-200c levels may not only serve as predictive marker of lymph node metastasis, but also predict poor prognosis and early recurrence in patients with higher accuracy than serum CEA levels or pathological staging.

TABLE 27

Uni- and multi-variate analyses for prognostic factors in CRC patients

| Variables | Univariate | | | Multivariate | | |
|---|---|---|---|---|---|---|
| | HR$ | 95% CI | p-value | HR$ | 95% CI | p value |
| Age (≥67 vs. <67) | 0.76 | 0.42-1.35 | 0.35 | — | — | — |
| Gender (Female vs. Male) | 1.02 | 0.56-1.86 | 0.92 | — | — | — |
| Pathological T stage (T3/4 vs. 1/2) | 8.97 | 2.19-36.7 | 0.0024 | 3.63 | 0.82-16.1 | 0.91 |
| Pathology (poor vs. mod/well differentiated) | 2.26 | 1.05-4.84 | 0.036 | 2.07 | 0.86-4.96 | 0.105 |
| Lymph node metastasis (positive vs. negative) | 17.1 | 6.18-47.8 | <0.0001 | 1.24 | 0.28-5.46 | 0.78 |
| TNM stage (III/IV vs. I/II) | 33.4 | 8.12-136.9 | <0.0001 | 10.2 | 1.27-81.7 | 0.03 |
| CEA (≥5 vs. <5) | 4.84 | 2.15-10.89 | 0.0001 | 1.46 | 0.57-3.74 | 0.43 |
| miR-200c in serum (high vs. low) | 2.43 | 1.26-4.68 | 0.006 | 2.67 | 1.28-5.67 | 0.01 |
| miR-200c in primary tumor (high vs. low) | 0.56 | 0.28-1.10 | 0.092 | — | — | — |

HR, Hazard ratio;

CI, Confidence interval;

CEA, Carcinoembryonic antigen;

mod, moderately;

TNM, tumor-node-metastasis staging $HR, hazard ratio for survival outcome in CRC patients

TABLE 28

Uni- and multi-variate analyses for predictive factors of recurrence in stage II-III CRC patients

| Variables | Univariate | | | Multivariate | | |
|---|---|---|---|---|---|---|
| | HR$ | 95% CI | p-value | HR$ | 95% CI | p value |
| Age (≥67 vs. <67) | 0.89 | 0.40-1.99 | 0.78 | — | — | — |
| Gender (Female vs. Male) | 0.65 | 0.29-1.44 | 0.29 | — | — | — |
| Pathological T stage (T3/4 vs. 1/2) | 0.78 | 0.18-3.33 | 0.75 | — | — | — |
| Pathology (poor vs. mod/well differentiated) | 1.29 | 0.39-4.34 | 0.67 | — | — | — |
| Venous invasion (positive vs. negative) | 2.47 | 1.05-5.78 | 0.038 | 3.76 | 1.43-9.93 | 0.008 |
| Lymphatic invasion (positive vs. negative) | 1.92 | 0.45-8.11 | 0.34 | — | — | — |
| TNM stage (III vs. II) | 3.98 | 1.71-9.30 | 0.0015 | 3.24 | 1.32-7.96 | 0.01 |
| CEA (≥5 vs. <5) | 1.89 | 0.77-4.62 | 0.1646 | — | — | — |
| miR-200c in serum (high vs. low) | 3.01 | 1.08-8.39 | 0.024 | 4.51 | 1.56-13.01 | 0.005 |

Investigation of miR-200c Source in Serum of CRC Patients—

Figures 21A, 21B, 21C, 21D:
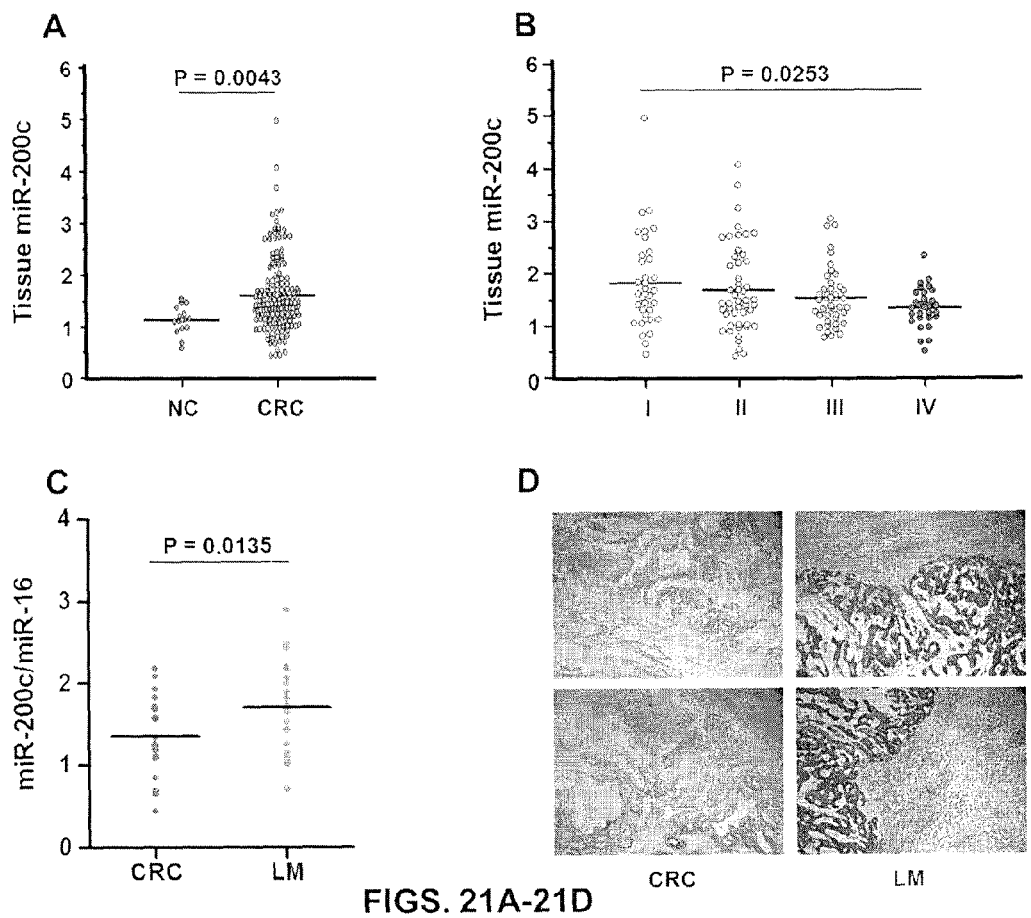
FIGS. 21A-21D—Expression of miR-200c in tissues from CRC patients. (A) Dot plots of miR-200c levels in adjacent normal mucosae (NC) (n=20) and CRC tissues (n=156). (B) Dot plots of miR-200c tissue levels across various CRC stages. (C) Dot plots of miR-200c tissue levels for comparisons between matched primary CRCs (CRC) (n=20) and their corresponding liver metastasis (LM) (n=20). (D) In situ hybridization analysis of miR-200c in matched primary CRCs and their corresponding LM. Representative photomicrographs are shown from 2 primary CRCs (left panels) and matched LM (right panels). MiR-200c expressions in LMs were higher than that in primary CRCs expressed. In contrast, miR-200c expression in normal liver tissues was either very low or absent. Line indicates the mean value. Expression levels of miR-200c were normalized to has-miR-16. Statistically significant differences were determined using Mann-Whitney tests and Kruskal-Wallis test.

In an effort to determine whether miR-200c levels in serum are of tumor origin, the expression levels of miR-200c was quantified in matched CRC tissues. As expected, miR-200c expression in CRC tissues was significantly higher than in normal colonic mucosa (P=0.0043; FIG. 21A). Surprisingly however, miR-200c levels in CRC tissues gradually decreased with increasing tumor stage and the levels in stage IV CRCs were significantly lower than in stage I CRC (P=0.0253; FIG. 21B), suggesting a lack of direct correlation between serum and matched tissue miR-200c expression. In addition, there were no associations between miR-200c expression in CRC and clinicopathological findings, except for lymphatic invasion (Table 25, FIG. 20B). miR-200c expression was analyzed in both primary CRC and matched liver metastases from 20 independent CRC patients. Of interest, the levels of miR-200c in liver metastases were significantly higher than in primary CRC (P=0.0135; FIG. 21C). Furthermore, miR-200c expression was confirmed in both primary CRC tumors and matched liver metastases by in situ hybridization, illustrating that miR-200c was highly expressed in liver metastases compared with primary CRC (FIG. 21D). Taken together, it is envisaged that a potential source of miR-200c in serum of CRC patients might be the metastatic sites; hence, serum miR-200c levels may serve as a superior metastasis, recurrence-predictive and prognostic marker of CRC.

Example 5—Clinical Significance of MicroRNA-124 Methylation and Expression in Colorectal Neoplasia Methods and Materials DNA Extraction from Formalin Fixed Paraffin Embedded (FFPE) Samples.

FFPE samples were cut serially at 10 μM Based on histological findings, the tissue of each region was microdissected and DNA was extracted using the QIAmp DNA FFPE tissue kit (Qiagen, Valencia, Calif., USA) according to the manufacturer's protocol.

DNA Methylation Analysis.

DNA was bisulfite modified using the EZ DNA methylation Gold Kit (Zymo Research, Irvine, Calif., USA). Methylation of putative miR-124 promoter region was quantified by bisulfite pyrosequencing (PSQ HS 96A pyrosequencing system, Qiagen). The methylation levels of some CpG sites were analyzed and the methylation levels of each sample are represented as the mean value of methylation levels of some CpG sites in microRNA promoter region.

RNA Isolation and qRT-PCR from FFPE Tissues.

Total RNA was isolated from FFPE samples using the RecoverAll Total Nucleic Acid Isolation Kit (Ambion Inc., Austin, Tex.). Briefly, tissue sections were microdissected to enrich for neoplastic cells, followed by deparaffinization and RNA extraction using the manufacturer's protocol. Total RNA was eluted in the appropriate buffer, and quantified using a NanoDrop Spectrophotometer (NanoDrop Technologies, Wilmington, Del.). Reverse transcription reactions were carried out using the TaqMan MicroRNA Reverse Transcription Kit (Applied Biosystems, Foster City, Calif.) in a total reaction volume of 15 μL. MiR-124 and miR-16 were quantified in duplicate by qRT-PCR, using MicroRNA Assay Kits (Applied Biosystems, Foster City, Calif.). qRT-PCR was performed on an Applied Biosystems 7000 Sequence Detection System with the following cycling conditions: 95° C. for 10 min, followed by 45 cycles of 95° C. for 15 s and 60° C. for 1 min. Cycle threshold (Ct) values were calculated with SDS 1.4 software (Applied Biosystems, Foster City, Calif.). Expression levels of tissue miRNAs were normalized using miR-16 using the $2^{-\Delta Ct}$ method. Differences between the groups are presented as ΔCt, indicating differences between Ct values of miRNAs of interest and Ct values of normalizer miRNAs.

Transfection of miR-124 Precursor Molecules.

Lovo, HT29 and HCT116 cells were transfected with Pre-miR miRNA precursor molecules (Ambion Inc, Austin, Tex.) or Pre-miR miRNA negative control #1 (Ambion Inc, Austin, Tex.) at a final concentration of 10 nM, using Lipofectamine 2000 (Invitrogen, Rockville Md.) according to manufacturer's instructions. For microarray and RT-PCR analysis, total RNA was extracted 48 h after transfection; for Western blot analysis, cell lysates were prepared 48 h after transfection. In order to ensure the transfection efficiency, the protein downregulation of CDK6 was verified, a previously validated target by Western blotting.

Gene Expression Microarray Analysis, RT-PCR and miRNA Target Prediction.

Lovo and HCT116 cells were transfected with control miRNA precursor or miR-124 precursor as described above. Extracted RNA was amplified using Illumina's TotalPrep RNA Amplification Kit. RNA integrity was assessed using the Agilent 2100 Bioanalyzer Labeled cRNA was hybridized overnight to Human HT-12 V3 chips, washed, and scanned on an Illumina BeadStation-500. Illumina's BeadStudio version 3.1 was used to process signal intensity values from the scans, and background subtracted. Normalization was done using quantiles with the Lumi R-package. Fold-changes were calculated with respect to their respective control. miRecords website (http://mirecords.umn.edu/miRecords) (reference) was used to predict the miRNA targeting of miR-124. In order to narrow down the list of predicted targets, genes found to be downregulated (>2 fold-change) after transfection of miR-124 precursor in the microarray were crossed with the genes predicted to be targets based on miRecords. Genes previously found to be associated with either CRC specifically or carcinogenesis in general were selected for validation. For reverse transcription-PCR (RT-PCR), RNA was reverse transcribed to cDNA from 1 μg of total RNA using random hexamers and Advantage RT—for PCR Kit (Clontech Laboratories, CA). Power SYBR Green (Applied Biosystems Inc., Foster City, Calif.) RTPCR was performed for selected targets found with the strategy described above. Results were normalized to the expression of β-actin. All the experiments were performed in triplicates.

Western Blot Analysis.

Western blot analysis was carried out using standard methods. The following primary antibodies were used: anti-CDK6 (cell signaling, MA) at 1:2000 dilution; anti-EB1 (cell signaling) at 1:1000 dilution and anti-β-actin antibody (Clone AC-15) at 1:32000 dilution Proliferation Assay.

Twenty-four hours after transfection, control miRNA precursor or miR-124 precursor-transfected cells were seeded at $5\times10^3$ cells per well in 96-well flat-bottomed microliter plates, in a final volume of 100 μL culture medium per well, and incubated in a humidified atmosphere. After 0-72 hour culture, MTT assays were used to assess cell viability. Briefly, 200 uL sterile MTT dye (5 mg/mL, Sigma, St Louis, Mo.) was added. After incubating for 4 hours at 37° C. in 5% CO2, MTT medium mixture was removed and 200 μL of dimethyl sulfoxide was added to each well. Absorbance was measured by SoftMax Pro (Molecular Devices Corp., Sunnyvale, Calif.) at a wavelength of 450 nm. Each experiment was performed independently three times in triplicates.

Invasion Assay.

Transfected cells ($2.5\times10^5$ cells/well) were seeded in serum-free media (in triplicate) in 24-well (8 μm pore size) Matrigel™ Invasion Chambers (BD Biosciences, Franklin Lakes, N.J.). Inserts were placed into Falcon companion plates containing 10% FBS and incubated for 48 hours. The incubation media and cells were then removed from the top chamber using cotton swabs and phosphate buffered saline and the number of cells invading the membrane underside was determined. Membranes were fixed and stained with Diff-Quik Stain™ (Sysmex, Kobe, Japan) and mounted on glass slides. The numbers of invading cells in 10 microscopic fields were subsequently counted with a light microscope at 10× magnification.

Migration Assay.

Transfected CRC cells were incubated until confluent in 6-well plates and wounds were generated using a sterile 200 μL pipette tip. Cells were then grown for an additional 24 hours. Wound closure was assessed using an Olympus IX71 microscope (Olympus, Center valley, PA) at 40× magnification. Cell migration distance was measured using Adobe Photoshop 9.0.2 software and compared with baseline measurements.

Statistical Analysis.

All data were analyzed using the Medcalc v12.3.0 (Broekstraat 52, 9030, Mariakerke, Belgium) software. Quantitative variables were analyzed using Student's test, Wilcoxon test (non-parametric paired analysis) and Mann-Whitney U test (non paired analysis). Qualitative variables were analyzed using either the Chi Square Test or the Fisher's test. Receiver operating characteristic (ROC) curves were established to distinguish neoplasia from normal colonic mucosa. The predictive accuracy was determined by measuring area under ROC curve (AUC), specificity and sensitivity. Survival analyses were performed using the Kaplan-Meier method and the differences in survival were examined using log-rank tests. Cox's proportional hazard regression analyses were used to estimate hazard ratios of death according miR-124 methylation levels and expression levels.

Results

Epigenetic Silencing of miR-124 is an Early Event in Colorectal Carcinogenesis.

Figures 24A, 24B, 24C, 24D:
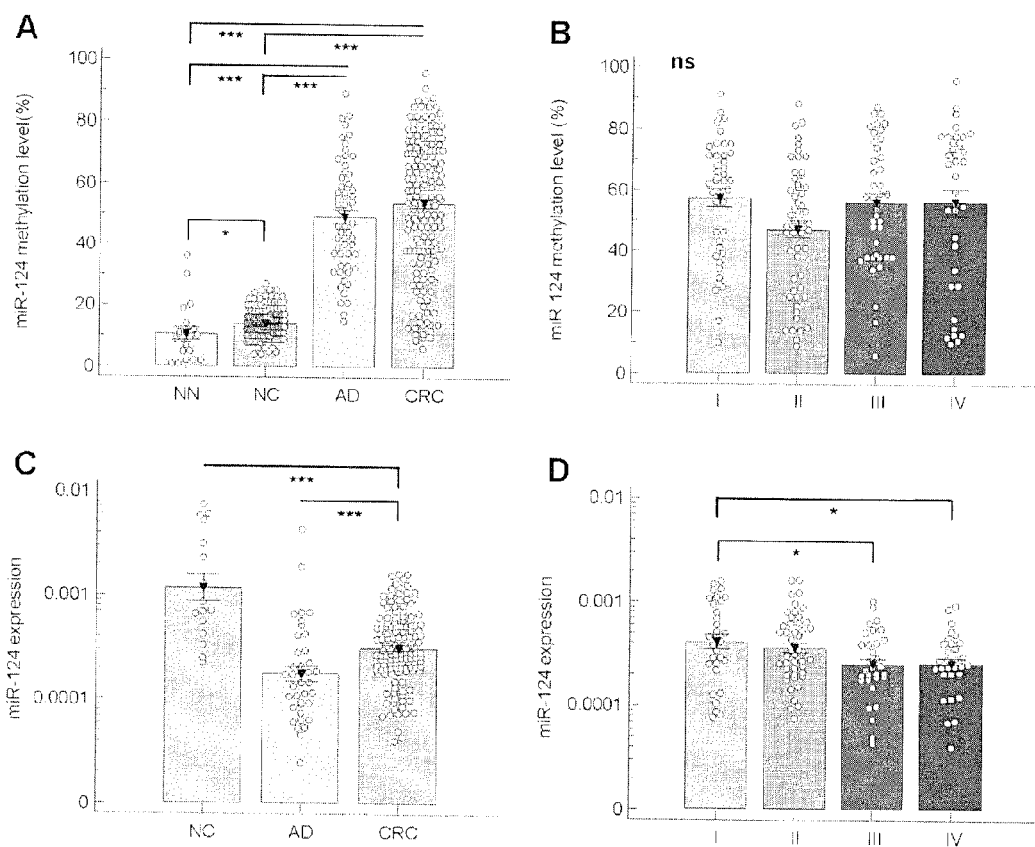
FIGS. 24A-24D—The miR-124 methylation (n=431) and expression levels (n=217) in colorectal samples. (A) Box plots representing miR-124 methylation in healthy controls (NN; n=20), patients with adjacent normal mucosa from colorectal cancer (CRC) (NC; n=177), patients with adenoma (AD: n=57) and patients with CRC (n=177) (B) Box plots illustrating miR-124 methylation levels across different stages of CRCs. (C) Box plots representing miR-124 expression levels in adjacent normal mucosa from colorectal cancer (CRC) (NC; n=20), adenoma (AD: n=57) and CRC (n=140) (D) Box plots illustrating miR-124 expression levels across different stages of CRCs. Boxes represent the interquartile range and the horizontal line across each box indicates median values. Data for tissue expression were normalized relative to miR-16 expression. Statistically significant differences were determined using the Mann-Whitney test. *P<0.05; ***P<0.0001.

The miR-124 pyrosequencing assay was used to analyze the methylation status in a cohort of colorectal tissues which included 20 normal mucosa from non-tumor patients (N-N), 177 CRC tissues with their corresponding adjacent normal mucosa (N-C), and 57 colorectal adenomas. The mean levels of methylation (±standard deviation, SD) in N-N, N-C, CRC and adenoma was 10.75% (±9.41), 14.14% (±4.51), 49.09% (±18.13) and 53.69% (±21.86), respectively (FIG. 24A). Thus, the level of miR-124 methylation was significantly higher in CRC tissues (53.69% vs. 14.14%, p<0.0001) (FIG. 24A), demonstrating the cancer specificity of miR-124 methylation.

Figures 25A, 25B, 25C, 25D:
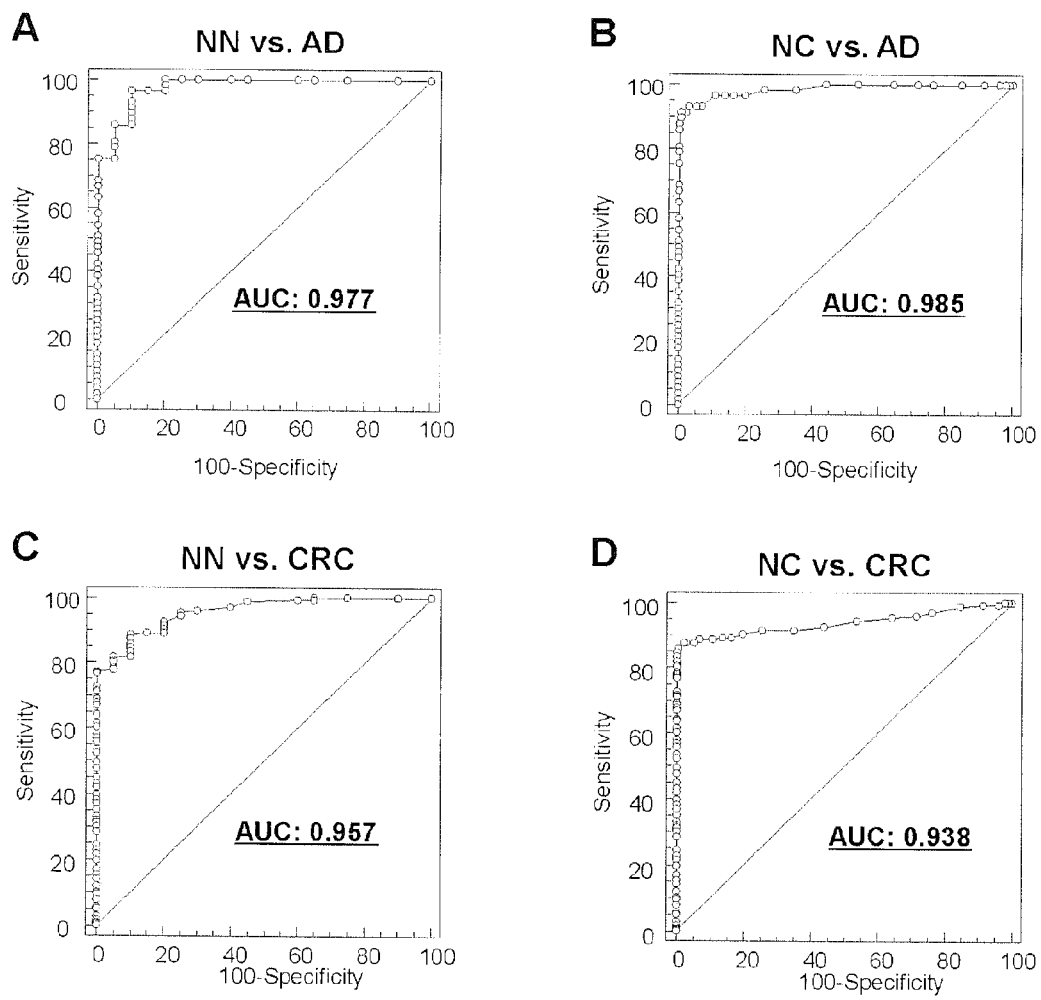
FIGS. 25A-25D—Receiver operating characteristics (ROC) curve analysis using serum miR-21 for distinguishing patients with colorectal neoplasms from normal controls. (A) miR-124 methylation levels yielded an AUC value of 0.960 (95% CI: 0.92-0.98), with 89.1% sensitivity and 90.0% in distinguishing CRC from healthy mucosa (B) AUC value of 0.942 for discriminating CRC from adjacent normal mucosa from CRC patients, with 88.0% sensitivity and 97.4% specificity. (C) miR-124 methylation levels yielded an AUC value of 0.977 (95% CI: 0.91-0.99), with 96.5% sensitivity and 90.0% specificity in distinguishing adenoma (AD) from healthy mucosa (NN) (D) AUC value of 0.985 (95% CI: 0.96-0.99) for discriminating adenoma (AD) from adjacent normal mucosa (NC) from CRC patients, with 91.2% sensitivity and 99.4% specificity.

In addition, a significantly higher degree of methylation was observed in N-C compared to N-N (14.14% vs. 10.75%, p<0.05) (FIG. 24A) consistent with the paradigm of methylation-related field defects in CRC. And more interestingly, methylation of mir-124 in adenoma showed the same degree of methylation as CRC. Next, the accuracy of this methylation was evaluated as histological differentiation between colonic neoplasia and adjacent normal mucosa. The ROC analysis showed that high miR-124 methylation levels can discriminate CRC from N-N or N-C with extreme high AUC values (CRC vs. N-N, 0.957, CRC vs, N-C, 0.938: FIGS. 25C and 25D). More importantly, AUC values of discriminating AD from N-N or N-C also were high with 0.977 and 0.985, respectively (FIGS. 25A and 25B). these results suggested that methylation of miR-124 methylation is an early event in colorectal carcinogenesis and has high accuracy of differentiating neoplasia in colorectum from normal colonic mucosa.

Figures 26A, 26B, 26C, 26D, 26E, 26F:
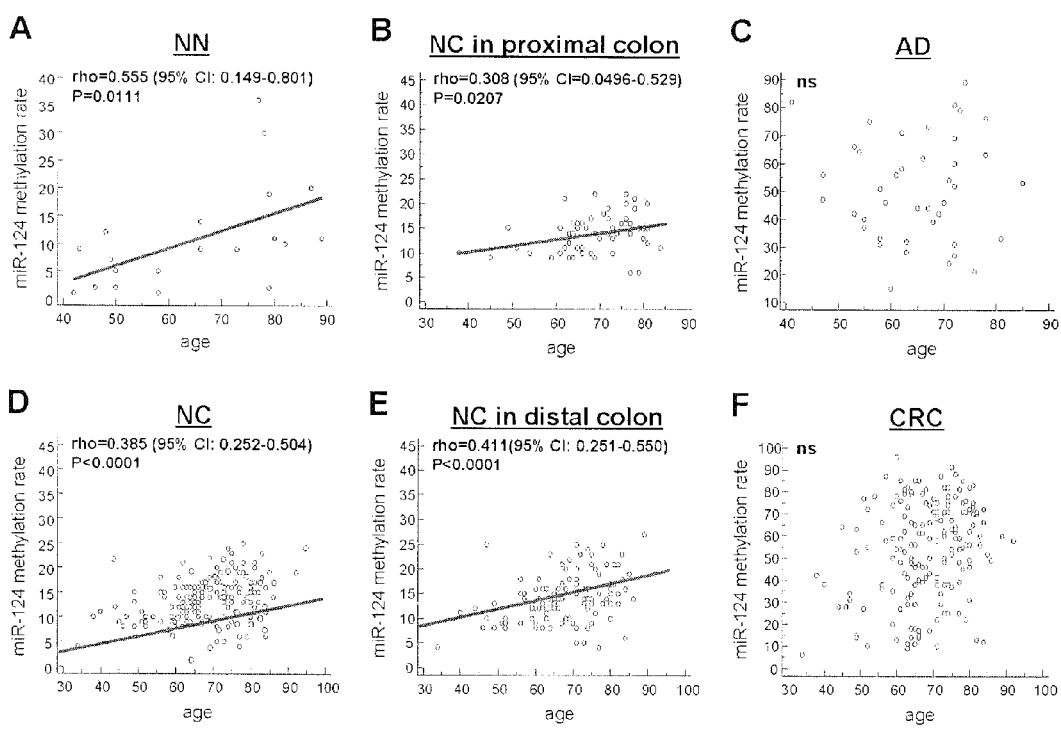
FIGS. 26A-26F—Correlation between miR-124 methylation and Age in healthy colonic mucosa (NN), adjacent normal mucosa (NC), adenoma (AD) and colorectal cancer (CRC) (A) Significant correlation between miR-124 methylation and Age in healthy colonic mucosa (rho=0.555 95% CI: 0.149-0.801, p<0.0001). (B) Significant correlation between miR-124 methylation and Age in adjacent normal mucosa (rho=0.385 95% CI: 0.252-0.504, p<0.0001). (C, D) No correlation between miR-124 methylation and Age in adenoma and CRC.

Next, the correlation between miR-124 methylation status of normal colonic mucosa and age was investigated. Methylation levels of miR-124 in both N-N and N-C significantly increased with patient age, respectively (N-N; rho=0.514 (95% CI=0.106-0.774) p=0.0172, N-C; rho=0.385 (95% CI=0.252-0.504) p<0.0001) (FIG. 26A, 26B). In addition, methylation levels miR-124 in distal colon exhibited a higher degree of leaning of liner regression with age (regression coefficient=0.1712) than that in proximal colon (regression coefficient=0.1262) (FIG. 26C, 26D). This result suggests that this methylation have an age related feature and is most specifically correlated with aging in the distal colonic mucosa. In contrast, the interesting result of which the significant correlation between miR-124 methylation in colonic tumors including adenoma and CRC disappeared was observed (FIG. 26E, 26F).

Furthermore, the relationships between miR-124 methylation levels and clinical categorical variables of CRC patients were analyzed (Table 29). High methylation levels of miR-124 in CRC were significantly associated with larger tumor size (p=0.03), presence of liver metastasis (p=0.003) and distant metastasis (p=0.01). In addition, significant association between miR-124 methylation and somatic KRAS mutation (p<0.0001) was recognized. However, there was no association between methylation status and TNM stage (FIG. 24A).

TABLE 29

Clinico-pathological features of colorectal cancer patients analyzed for miR-124 methylation.

| Factors | | Low methylation (n = 120) | High methylation (n = 55) | P |
|---|---|---|---|---|
| Age | ≤68 | 62 | 18 | 0.029 |
| | >68 | 58 | 37 | |
| Gender | Male | 67 | 28 | 0.63 |
| | Female | 42 | 22 | |
| Histological grade | Well and mod | 108 | 52 | 0.74 |
| | Poor and muci | 12 | 4 | |
| KRAS mutation | positive | 100 | 28 | <0.0001 |
| | negative | 20 | 27 | |
| BRAF mutation | positive | 119 | 53 | 0.49 |
| | negative | 1 | 2 | |
| Tumor size | ≤40 (small) | 59 | 18 | 0.03 |
| | >40 (large) | 50 | 33 | |
| Serosal invasion | Absent | 31 | 20 | 0.24 |
| | Present | 89 | 36 | |
| Lymph node metastasis | Absent | 75 | 26 | 0.065 |
| | Present | 45 | 30 | |
| Venous invasion | Absent | 66 | 33 | 0.74 |
| | Present | 54 | 23 | |
| Lymphatic invasion | Absent | 30 | 13 | 0.94 |
| | Present | 90 | 43 | |
| Liver metastasis | Absent | 111 | 42 | 0.003 |
| | Present | 9 | 14 | |
| Distant metastasis | Absent | 101 | 37 | 0.01 |
| | Present | 19 | 19 | |

MiR-124 is Constitutively Expressed in Normal Colonic Mucosa and Down-Regulated in Adenoma and CRC.

TaqMan RT-PCR was used to assess the expression of miR-124 in matched 140 tissues of 174 CRC, 57 adenoma and 20 adjacent normal mucosa, and found substantial downregulation of the expression in the tumor tissues including adenoma and CRC compared with the normal mucosa, respectively (p<0.0001, p<0.0001 FIG. 24C). In CRC, miR-124 expression levels decreased according to TNM progression, and this methylation levels in Stage III or Stage IV were significantly lower than that in Stage I (P<0.05; Stage I vs. III, P<0.05; Stage I vs. IV: FIG. 24D).

Next, the relationships between miR-124 expressions and clinicopathological findings of CRC patients were investigated (Table 30). High levels of miR-124 expression were significantly associated with presence of lymph node metastasis (p=0.01) and distant metastasis (p=0.03).

TABLE 30

Clinico-pathological features of colorectal cancer patients analyzed for miR-124 expression.

| Factors | | Low levels (n = 97) | High levels (n = 43) | P |
|---|---|---|---|---|
| Age | ≤68 | 48 | 21 | 0.91 |
| | >68 | 49 | 22 | |
| Gender | Male | 55 | 30 | 0.15 |
| | Female | 42 | 12 | |
| Histological grade | Well and mod | 85 | 42 | 0.11 |
| | Poor and muci | 12 | 1 | |
| Tumor size | ≤40 (small) | 45 | 23 | 0.59 |
| | >40 (large) | 51 | 20 | |
| Serosal invasion | Absent | 25 | 15 | 0.37 |
| | Present | 72 | 28 | |
| Lymph node metastasis | Absent | 48 | 32 | 0.01 |
| | Present | 49 | 11 | |
| Venous invasion | Absent | 53 | 25 | 0.84 |
| | Present | 44 | 18 | |
| Lymphatic invasion | Absent | 26 | 10 | 0.069 |
| | Present | 83 | 41 | |
| Liver metastasis | Absent | 81 | 39 | 0.39 |
| | Present | 16 | 4 | |
| Distant metastasis | Absent | 71 | 39 | 0.03 |
| | Present | 26 | 4 | |

MiR-124 Transfection Inhibits Cell Proliferation, Migration and Invasion.

Figures 28A, 28B, 28C:
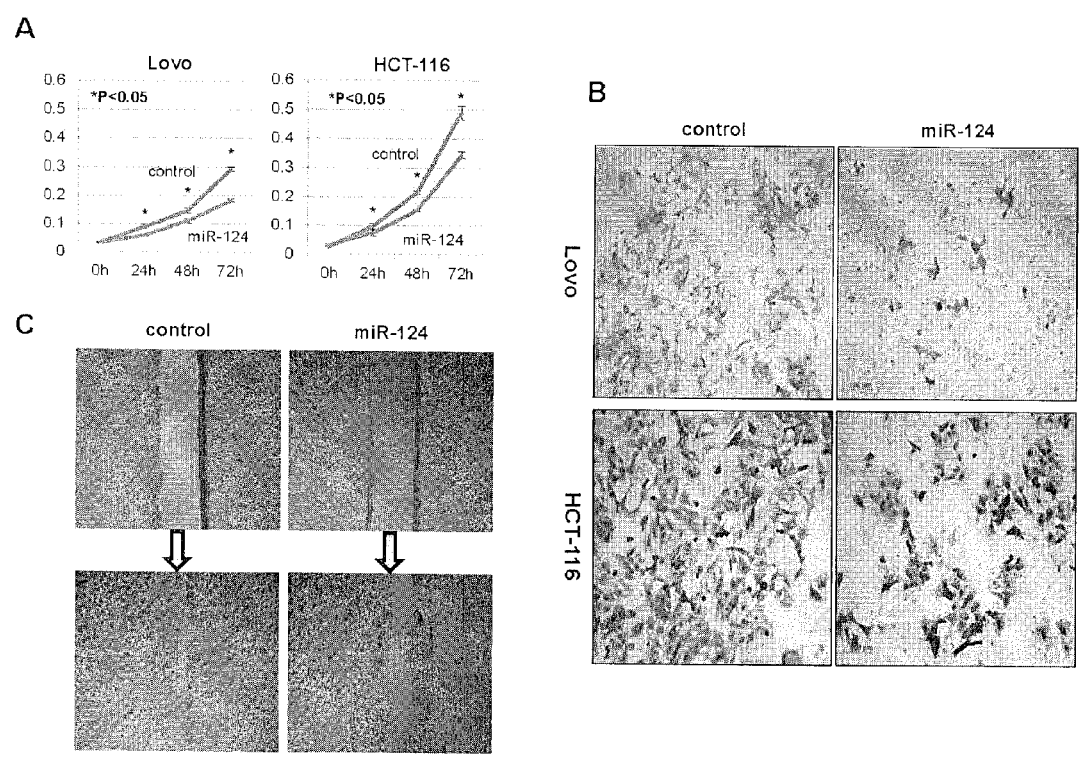
FIGS. 28A-28C—Functional analysis in vitro after transfection of either miR-124 precursor or negative control precursor to CRC cell lines (A) MTT assay showed that restoration of miR-124 inhibits cell growth in both Lovo and HCT-116 cell lines at 24 h, 48 h and 72 h after transfection. (B) Invasion assay shows Transfection of miR-124 precursor inhibits invasion ability of Lovo and HCT-116 cells compared to negative control precursor. (C) Wound healing assay shows that transfection of miR-124 precursor inhibits migration ability of both cell lines compared to negative control precursor.

Since miR-124 expression is significantly down-regulated in colonic neoplasia including adenoma and CRC, and might be silenced epigenetically, functional studies were performed to investigate whether miR-124 had in vitro tumor suppressive features following transfection of miR-124 precursor in CRC cells. MTT assay was first performed. Restoration of miR-124 significantly reduced cell proliferation in both Lovo and HCT-116 at 24 h, 48 h and 72 h after transfection of miR-124 (FIG. 28A). Next, to determine whether restoration of miR-124 levels might affect cellular invasion, invasion assays was performed. MiR-124 precursor transfection of Lovo and HCT-116 showed weakened invasive capacity compared to cells transfected with negative control precursor (FIG. 28B). Finally, a wound assay was performed to compare the migratory potential of CRC transfected with miR-124 precursor or negative control precursor. The number of migratory cells treated with miR-124 precursor was markedly decreased compared to negative control precursor treated cells (FIG. 28C).

MiR-124 Methylation and Expression are Prognostic Factors in CRC.

Figures 27A, 27B:
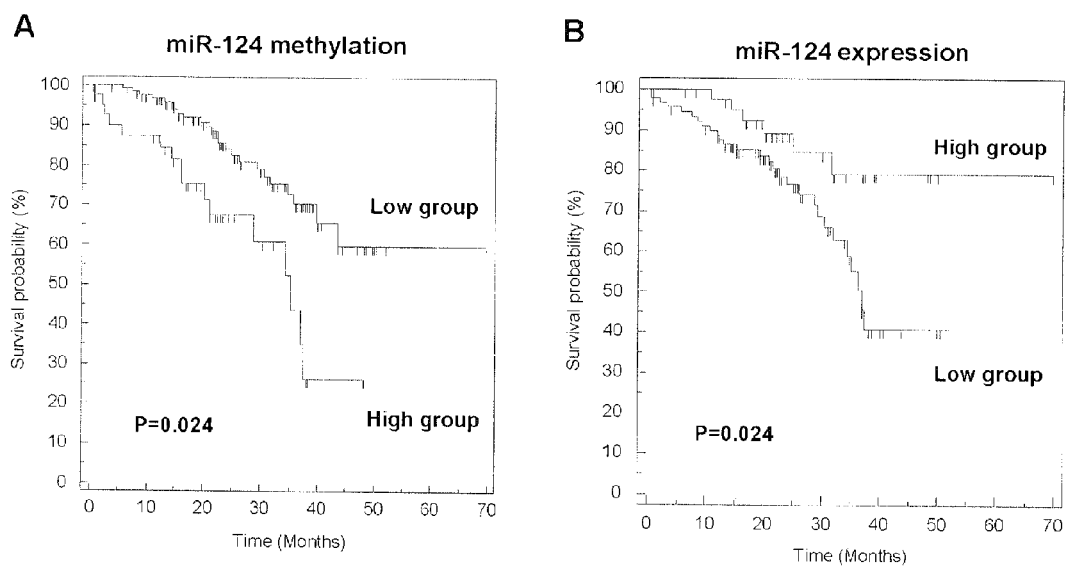
FIGS. 27A-27B—Kaplan-Meier survival analysis in CRC patients based upon miR-124 methylation and expression in primary CRC samples. (A) The overall survival rate in CRC patients with high miR-124 methylation levels in tumor was significantly lower than for those with low miR-21 expression (>3.7 vs <3.7; P=0.024; log-rank test). (B) The overall survival rate in CRC patients with low miR-124 expression levels was significantly lower than for those with high miR-124 expression (>0.0031 vs <0.0031; P=0.001; log-rank test). Cut-off values for miR-124 methylation and expression in CRC were determined from the ROC curves with Youden index.

To assess the prognostic ability of miR-124 methylation and expression, K-M analysis was performed. FIG. 27A showed survival curves subdivided by miR-124 methylation levels, and demonstrated that the patients with high methylation levels in CRC are significantly poor prognosis compared with those with low methylation levels (p=0.024). In contrast, patients with low miR-124 expression levels are shorter survival than those with high expression levels (p=0.001: FIG. 27B) In addition, Cox-hazard regression model was performed to identify the valuables associated with prognosis (Table 31). Univariate analysis showed that high T stage (p=0.0024), lymph node metastasis positive (p<0.0001), distant metastasis positive (p<0.0001), poor differentiation (p=0.036), high CEA value (p=0.0001), high miR-124 methylation (p=0.0012) and expression levels (p=0.017) are prognostic factors in the CRC cohort. More importantly, high levels of miR-124 methylation is one of independent prognostic factors in CRC(OR: 2.59 95% CI=1.08-6.20, p=0.033: Table 31)

TABLE 31

Uni- and Multivariate analyses for prognostic factors in colorectal cancer

| Variables | Univariate | | | Multivariate | | |
|---|---|---|---|---|---|---|
| | OR | 95% CI | p | OR | 95% CI | p |
| Age (>67 vs. ≤67) | 0.72 | 0.43-1.37 | 0.37 | 0.75 | 0.31-1.83 | 0.53 |
| Gender (Female vs. Male) | 1.02 | 0.56-1.86 | 0.92 | 1.07 | 0.44-2.60 | 0.88 |
| Pathological T (T3.4 vs. 1.2) | 8.97 | 2.19-36.70 | 0.0024 | 4.53 | 0.49-41.91 | 0.19 |
| Pathology (poor diff. vs. diff.) | 2.26 | 1.05-4.84 | 0.036 | 1.91 | 0.57-6.38 | 0.29 |
| Lymph node metastasis (yes vs. no) | 17.10 | 6.18-47.8 | <0.0001 | 3.84 | 1.11-13.29 | 0.035 |
| Distant metastasis (yes vs. no) | 35.60 | 14.4-86.6 | <0.0001 | 16.3 | 5 06-52.61 | <0.0001 |
| CEA (>6 vs. ≤6) | 4.84 | 2.15-10.89 | 0.0001 | 0.92 | 0.26-2.96 | 0.89 |
| Mir-124 methylation levels (high vs. low) | 2.86 | 1.51-5.39 | 0.0012 | 2.59 | 1.08-6.20 | 0.033 |
| Mir-124 expression levels (high vs. low) | 0.38 | 0.16-0.91 | 0.017 | 0.86 | 0.31-2.35 | 0.77 |

OR: Odds Ratio,
CI: Confidence Interval,
CEA: Carcino-Embryonic Antigen

Identification of Potential Gene Targets of miR-124.

In order to identify target genes of miR-124, microarray analysis was first performed in Lovo, HT29 and HCT116 cells after transfection of either miR-124 or negative control precursors. One hundred fifty-three genes showed more than 1.5 decreases in their expression following miR-124 transfection, compared to negative controls (FIG. 29A). the miRecords resource was next used to obtain the target genes with seeding cords of miR-124. After cross-referencing the microarray data and miRecords, 40 genes which are candidate of miR-124 target genes according to the criteria were determined (FIG. 29B).

Figure 29C:
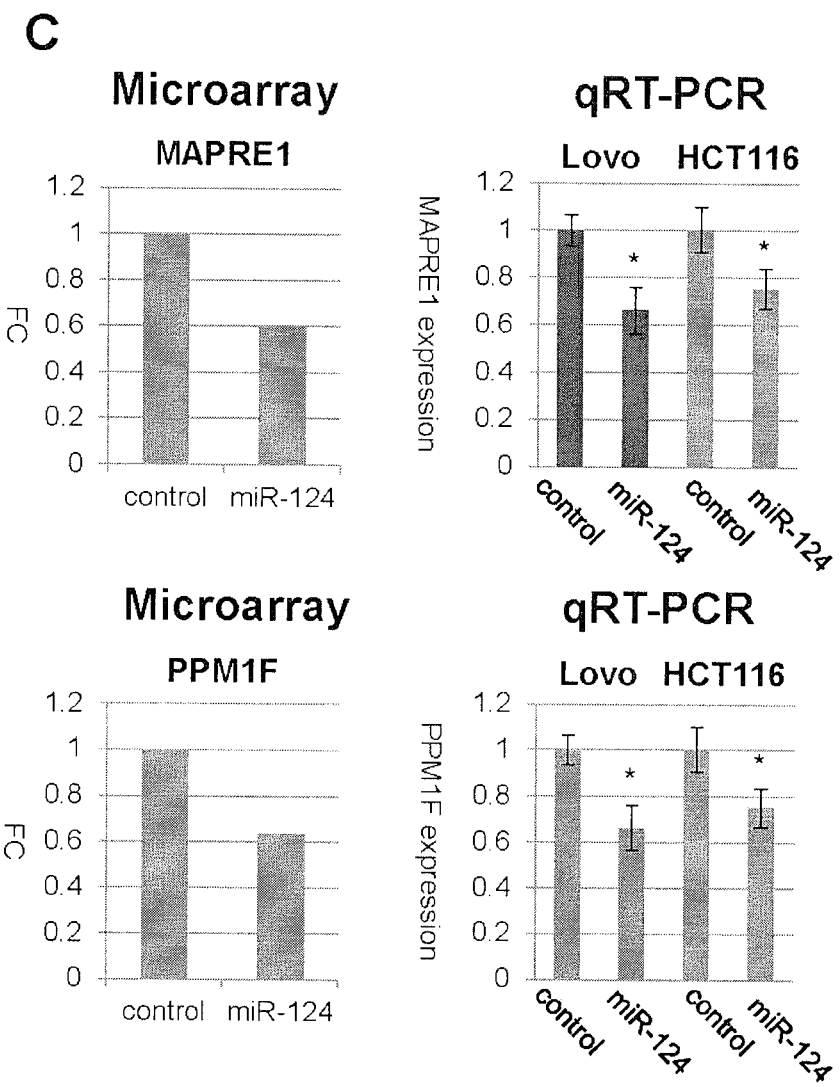

The microarray data by RT-PCR were determined for a subset of selected genes (FIG. 29C). Two candidate genes—Microtubule-associated protein RP/EB family member (MAPRE1) and Protein Phosphatase, Mg2+/Mn2+ dependent, 1F (PPM1F)—were chosen for validation because of their putative role in carcinogenesis, tumor invasion and migration.

Example 6—Serum miR-200c is a Novel Prognostic and Metastasis-Predictive Biomarker in Patients with Colorectal Cancer Methods RNA Isolation from Serum and Quantitative RT-PCR.

Small RNA was enriched from all serum samples using the Qiagen miRneasy Kit (Ambion, Austin, Tex.). Briefly, 250 uL of serum and condition medium of cell culture were thawed on ice and centrifuged at 10,000 rpm for 5 minutes to remove cell debris and other cellular organelles. Next, 200 uL of supernatant was lysed with 5 volume of Qiazol solution. For normalization of sample-to-sample variation during the RNA isolation procedures, 25 fmol of synthetic C. elegans miRNA (cel-miR-39) was added to each denatured sample. Small RNAs were then enriched and purified following manufacturer's protocol, with the exception that the enriched small RNAs were eluted in 40 uL of preheated nuclease-free water. For microRNA based RT-PCR assays, 1.67 uL of enriched small RNAs from serum samples were reverse transcribed using the TaqMan MicroRNA Reverse Transcription Kit (Applied Biosystems, San Diego, Calif.) according to manufacturer's instructions in a total reaction volume of 5.0 uL. A 1:15 dilution of RT products was used as template for the PCR stage. PCR reaction for quantification the amount of miR-21, miR-31 and cel-miR-39 was performed in duplicates using TaqMan 2× Universal PCR Master Mix with conditions as described previously. Quantitative PCR was performed using an Applied Biosystems 7300 Sequence detection system with following cycles: 95° C. for 10 min, followed by 45 cycles of 95° C. for 15 s and 60° C. for 1 min. The cycle threshold (Ct) values were calculated with SDS 1.4 software (Applied Biosystems).

RNA Isolation from FFPE Tissues and Quantitative RT-PCR.

Total RNA was isolated from the FFPE samples using the RecoverAll Total Nucleic Acid Isolation Kit (Ambion) according to manufacturer's instructions. Briefly, each FFPE tissue block was cut into 10-µm thick pieces, and then manually microdissected to collect cancer cells with reference to hematoxylin-eosin slides. To liquefy paraffin specimens, 100% xylene and 100% ethanol were added into each tube. After centrifugation, precipitated samples were air-dried and treated with protease in heat blocks for 3 hours at 50° C. Each sample was then treated with isolation reagent and filtered. Each filter was treated with DNase and incubated for 30 minutes at room temperature. After washing the filter with washing reagents, it was treated with warmed Elution Solution and centrifuged to pass the mixture through the filter. The eluate contained the isolated RNA. The concentration was quantified with a NanoDrop Spectrophotometer (NanoDrop Technologies). The miR-200c, miR-203 and miR-16 were quantified in duplicate by qRT-PCR, using TaqMan MicroRNA Assay Kits (Applied Biosystems). Reverse transcription reactions were carried out with TaqMan MicroRNA Reverse Transcription Kit (Applied Biosystems, San Diego, Calif.) according to manufacturer's instructions, in a total reaction volume of 15 uL. Quantitative PCR was performed on an Applied Biosystems 7300 Sequence detection system with following cycles: 95° C. for 10 min, followed by 45 cycles of 95° C. for 15 s and 60° C. for 1 min. Cycle threshold (Ct) values were calculated with SDS 1.4 software (Applied Biosystems).

Calculations of miRNAs.

The average expression levels of serum or tissue miRNAs were normalized with cel-miR-39 and miR-16 using the $2^{-\Delta Ct}$ methods. Differences between the groups are presented as ΔCt, indicating the difference between the Ct value of the miRNA of interest and the Ct value of the normalizer miRNA.

Statistical Analysis.

The significance of serum miRNA levels was determined by the Mann-Whitney test, Wilcoxon test, or Kruskal-Wallis test where appropriate. The Spearman rank order correlation test was used to examine correlation between the levels of miRNA in serum and matched primary cancer lesion. Receiver operating characteristic (ROC) curves were established for determine cut-off values for analyzing survival or prediction of LN metastasis. Overall survival curve was analyzed using the Kaplan-Meier method, and differences were examined using Log-rank tests. Cox proportional hazard regression was used to estimate univmiate and multivariate hazard ratios for prognosis. All p-values are two-sided and less than 0.05 was considered statistically. All statistical analyses were carried out using Medcalc 7.2 for Windows (Broekstraat 52, 9030, Mariakerke, Belgium).

Results:

Screening Analysis of EMT Related miRNAs in Serum of Stage I and Stage IV CRC Patients on a Small Number Set.

Figures 30A, 30B, 30C, 30D, 30E:
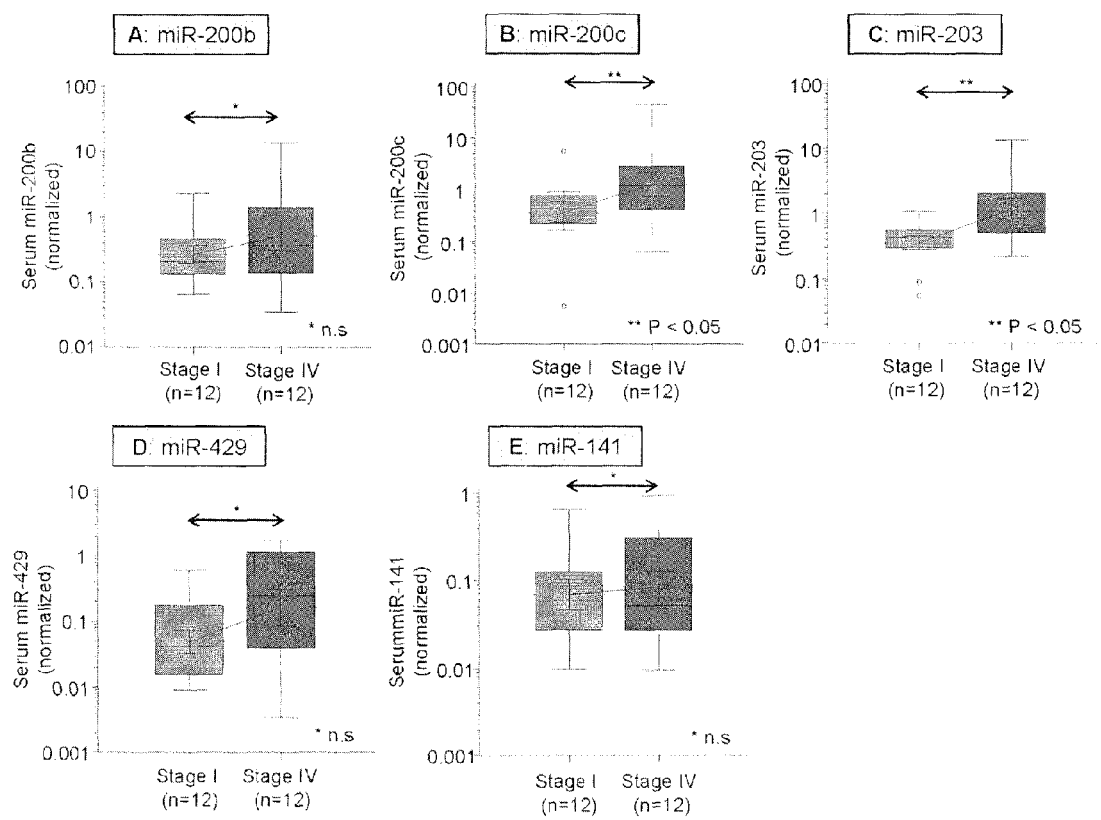
FIGS. 30A-30E—Small-scale examinations of miR-200 family and miR-203 expression in serum with Stage I and Stage IV CRC patients. Box plots of serum levels of miR-200b (A), miR-200c (B), miR-203 (C), miR-429 (D) and miR-141 (E) in Stage I and Stage IV from 12 CRC patients, respectively. MiR-200c and miR-203 levels in serum with stage IV are significantly higher than that in stage I CRC patients. The box represents the interquartile range and the line across the box indicates the median value. Expression levels of miR-200c and miR-203 (log 10 scale on the y-axis) are normalized to cel-miR-39. Statistically analysis was performed using Mann-Whiteny tests.

In this screening step, qRT-PCR based expression assay for miR-141, miR-200b, miR-200c, miR-429 and miR-203 in serums from 12 stage I and 12 stage IV CRC patients was performed. The results showed that miR-200c and miR-203 were significantly elevated in serum with stage IV CRC patients when compared that with stage I CRC patients (miR-200c: p<0.05, miR-203: p<0.05) (FIGS. 30B and 30C). In contrast, no significant difference was observed in miR-141, miR-200b and miR-429 expression in serum between stage I and stage IV (FIGS. 30A, 30E and 30D). Based on these observations, miR-200c and miR-203 in serum with CRC were focused to further assess their capacities as a prognostic marker in large scale validation.

Patient Characteristics in Large Scale Set.

Patient characteristics and distribution of tumor stages are summarized in Table 32. There were no significant differences of age between patients with CRC (67 (SD 10.4) years) and healthy controls (64 (SD 12.9) years). (p>0.05: ANOVA) The sex distribution in the CRC group was 105:79 (male:female) and in the control group was 13:11 (p>0.05, Chi-square test). In analysis of miR-200c and miR-203 expression in primary tumors, a total of 92 patients of 184 with CRC were recruited. Both serum and matched tissue were collected from 80 patients out of 184 with CRC.

TABLE 32

Characteristics for serum and tissue miR-200c and miR-203 analysis in validation set

| Characteristics | Patients with CRC for serum analysis | Patients with CRC for tissue analysis Number | Normal Controls | p-value |
|---|---|---|---|---|
| | n = 184 | n = 92/184 | n = 24 | |
| Age (years) | | | | |
| Mean ± SD | 67 ± 10.4 | — | 64 ± 12.9 | n.s |
| Gender | | | | |
| Male | 105 | — | 13 | n.s |
| Female | 79 | — | 11 | |

TABLE 32-continued

Characteristics for serum and tissue miR-200c and miR-203 analysis in validation set

| Characteristics | Patients with CRC for serum analysis | Patients with CRC for tissue analysis Number | Normal Controls | p-value |
|---|---|---|---|---|
| | n = 184 | n = 92/184 | n = 24 | |
| TNM stage | | | | |
| I | 44 | 18 | — | |
| II | 59 | 34 | — | |
| III | 41 | 19 | — | |
| IV | 40 | 21 | — | |

CRC: colorectal cancer;
TNM: tumor-node-metastasis staging system;
SD: Standard Deviation;
n.s: not significant Validation of miR-200c and miR-203 Result from Serum and Tissue in Large Set of Patients Serum miR-200c and miR-203 Expression Levels are Correlated with Clinical Stages.

Figures 31A, 31B, 31C, 31D:
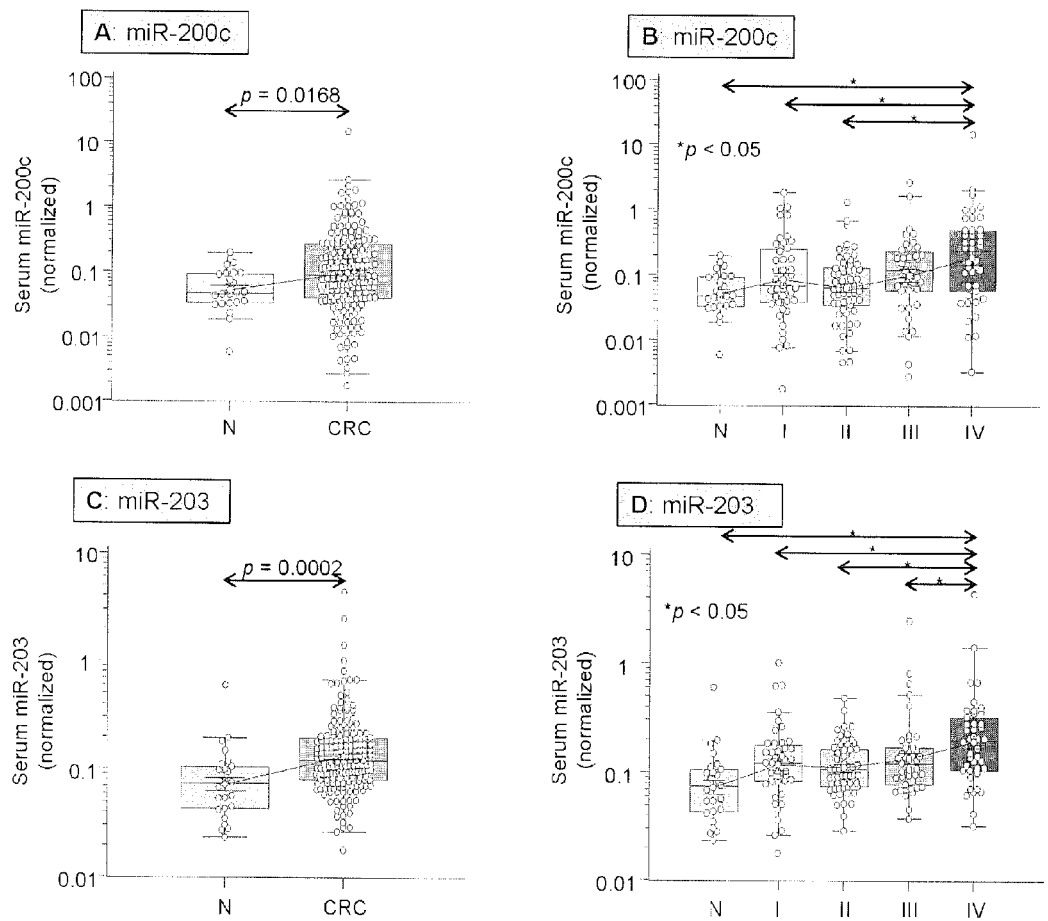
FIGS. 31A-31D—Large-scale validation of miR-200c and miR-203 in serum samples (n=208). (A) Box plot of serum miR-200c level in healthy normal controls (NC) (n=24) and patients with CRC (n=184). (B) Box plot of serum miR-200c level across TNM stage. (C) Box plot of serum miR-203 level in healthy normal controls (NC) (n=24) and patients with CRC (n=184). (D) Box plot of serum miR-203 level across TNM stage. MiR-200c and miR-203 levels in serum with CRC are significantly elevated compared to those in normal control and each miRNA level in stage IV CRC patients is significantly higher than that in stage I-II. The Box represents the interquartile range and the line across the box indicates the median value. Expression levels of miR-200c and miR-203 (log 10 scale on the y-axis) are normalized to cel-miR-39. Statistically significant differences were determined using Mann-Whiteny tests and Kruska-Wallis test. The patient number of stage I, II, III and IV is 44, 59, 41 and 40, respectively.

The expression levels of miR-200c in CRC were significantly higher compared to that in normal control (p=0.0168) (FIG. 31A). MiR-200c levels in serum increased depending TNM stage and were significantly higher in Stage IV patients than in normal controls, Stage I and Stage II patients (FIG. 31B).

In similar way, serum miR-203 levels in CRC were also significantly higher than that in normal control (p=0.0002) (FIG. 31C) and significant difference in miR-203 levels between Stage IV patients and the other stages was found (Stage I, II and III) (FIG. 31D).

Clinical Significance of miR-200c and miR-203 Expression in Serum of CRC Patients.

The mean fold changes of analyzed miR-200c and miR-203 m serum and their possible connection to clinical significances are presented in Table 33. High expression of miR-200c in serum was associated with lymph node metastasis (p=0.0008), liver metastasis (p<0.0001), peritoneal dissemination (p=0.018) and the development of distant metastases (p=0.0003) in CRC patients. Similarly, miR-203 expression in serum is significantly higher in the patients with venous invasion (p=0.045), lymph node metastasis (p=0.013), liver metastasis (p=0.0004), peritoneal dissemination (p=0.003) and distant metastases (p=0.0008), respectively.

TABLE 33

Clinical significances of preoperative serum miR-200c and miR-203 levels in CRC

| Factors | | Number | miR-200c (mean ± SD) | p-value | miR-203 (mean ± SD) | p-value |
|---|---|---|---|---|---|---|
| Age | >67 | 96 | 0.283 ± 0.43 | 0.418 | 0.183 ± 0.188 | 0.227 |
| | ≤67 | 88 | 0.336 ± 1.51 | | 0.275 ± 0.698 | |
| Gender | Male | 105 | 0.335 ± 1.445 | 0.331 | 0.224 ± 0.450 | 0.095 |
| | Female | 79 | 0.270 ± 0.466 | | 0.182 ± 0.148 | |
| Tumor size | ≤4 cm | 91 | 0.388 ± 1.60 | 0.474 | 0.215 ± 0.516 | 0.202 |
| | >4 cm | 93 | 0.233 ± 0.363 | | 0.199 ± 0.210 | |
| Serosal invasion | negative | 56 | 0.232 ± 0.452 | 0.835 | 0.162 ± 0.166 | 0.37 |
| | positive | 128 | 0.336 ± 1.333 | | 0.226 ± 0.455 | |

TABLE 33-continued

Clinical significances of preoperative serum miR-200c and miR-203 levels in CRC

| Factors | | Number | miR-200c (mean ± SD) | p-value | miR-203 (mean ± SD) | p-value |
|---|---|---|---|---|---|---|
| Lymphatic invasion | negative | 48 | 0.169 ± 0.294 | 0.288 | 0.146 ± 0.124 | 0.248 |
| | positive | 136 | 0.354 ± 1.301 | | 0.225 ± 0.441 | |
| Venous invasion | negative | 107 | 0.215 ± 0.398 | 0.514 | 0.152 ± 0.134 | 0.045* |
| | positive | 77 | 0.434 ± 1.683 | | 0.281 ± 0.575 | |
| Lymph node | negative | 109 | 0.158 ± 0.267 | 0.0008* | 0.145 ± 0.131 | 0.013* |
| metastasis | positive | 75 | 0.520 ± 1.726 | | 0.290 ± 0.574 | |
| Liver metastasis | negative | 158 | 0.181 ± 0.329 | <0.0001* | 0.166 ± 0.229 | 0.0004* |
| | positive | 26 | 1.063 ± 2.826 | | 0.450 ± 0.842 | |
| Peritoneal metastasis | negative | 173 | 0.207 ± 0.355 | 0.018* | 0.172 ± 0.225 | 0.003* |
| | positive | 11 | 1.844 ± 4.296 | | 0.735 ± 1.256 | |
| Distant metastasis | negative | 144 | 0.182 ± 0.342 | 0.0003* | 0.166 ± 0.238 | 0.0008* |
| | positive | 40 | 0.751 ± 2.305 | | 0.351 ± 0.691 | |

*$p < 0.05$;
CRC: colorectal cancer;
SD: Standard Deviation

Figures 32A, 32B, 32C, 32D:
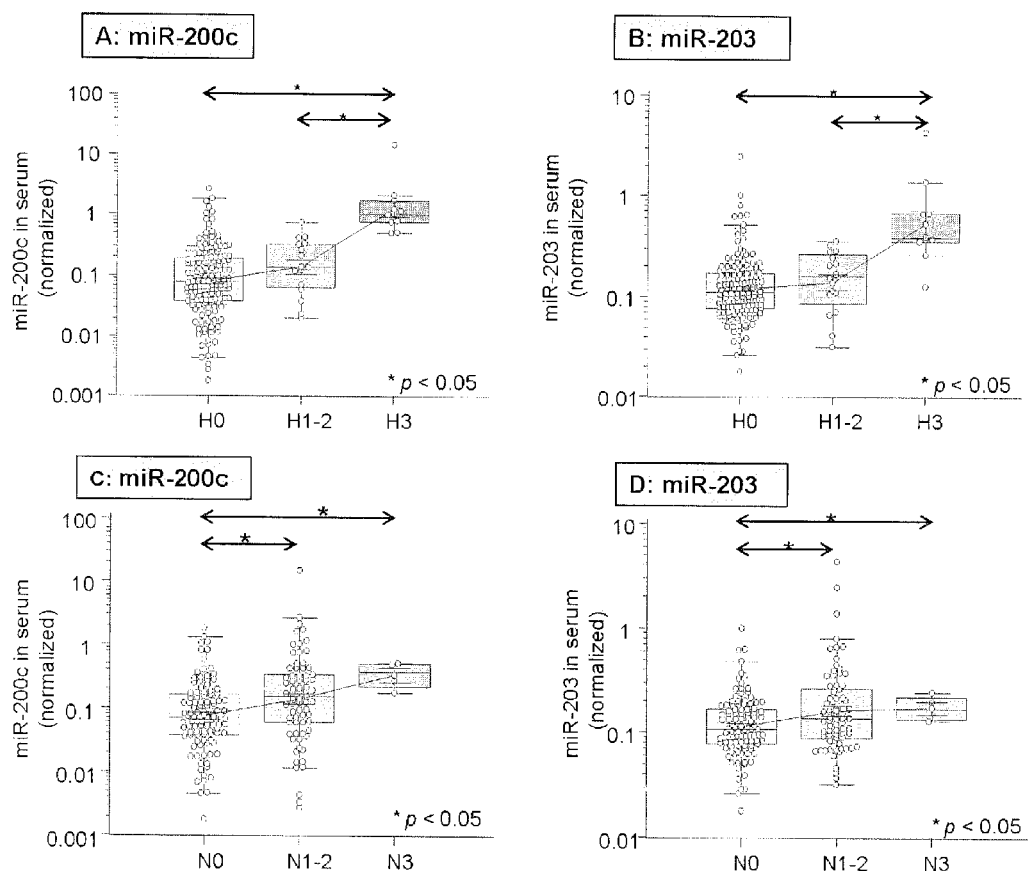
FIGS. 32A-32D—Box plots of serum miR-200c and miR-203 level in patients with CRC subdivided by Clinical H stage and Pathological N stage.

In particular, miR-200c and miR-203 levels in serum with H3CRC patients were significantly higher than that with H0 or H1-2 CRC patients (miR-200c: $p<0.0001$, miR-203: $p<0.0001$) (H0: no liver metastasis, H1: liver metastasis with less than 5 metastasis and smaller than 5 cm, H2: the other metastasis not involving H1 and H3, H3: liver metastasis with more than 5 metastasis and larger than 5 cm) (FIG. 32A, 32B).

Predictive Ability of Serum miR-200c and miR-203 Levels for Lymph Node Metastasis in CRC.

Serum miR-200c and 203 levels with lymph node metastasis were significantly higher than that without in CRC, respectively (Table 33). In addition, both miR-200c and miR-203 in serum is significantly higher in the patients with lymph node metastasis to aorta (n3) compared to regional (n1-2) or no lymph node metastasis (n0) (FIG. 32C, 32D). Univariate logistic regression analysis showed that high invasive tumor (T3/4) ($p=0.0024$), lymphatic ($p<0.0001$) and venous invasion positive ($p=0.0001$), high CEA levels ($p=0.0001$), high levels of miR-200c ($p=0.0001$) and miR-203 ($p=0.0064$) were significantly associated with lymph node metastasis (Table 34). Furthermore, miR-200c was the best predictor of lymph node metastasis in CRC by multivariate logistic regression analysis (miR-200c: HR=4.81, 95% CI=1.98-11.7 $p=0.0005$) (Table 34).

Prognostic Ability of miR-200c and miR-203 Levels Both in Serum in CRC.

Figures 33A, 33B:
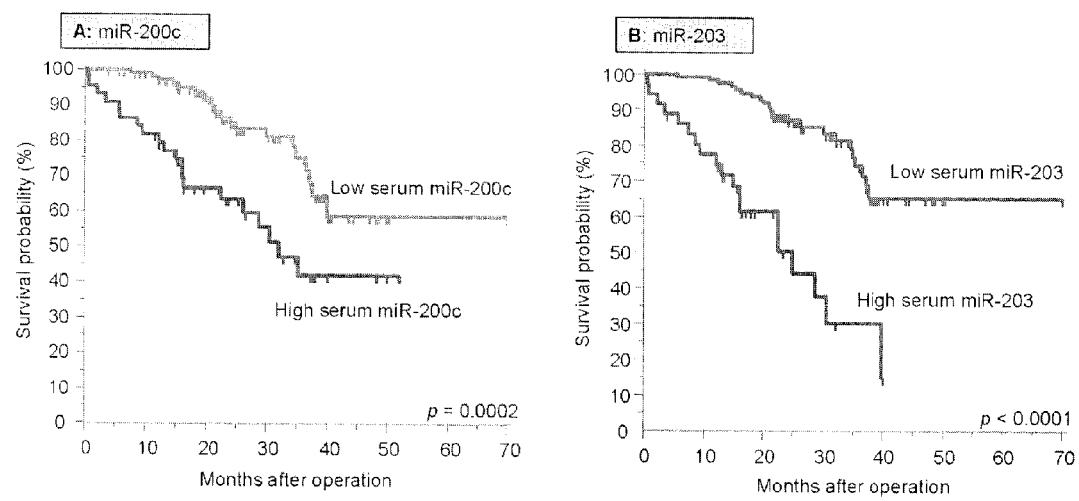
FIGS. 33A-33B—Kaplan-Meier survival curves subdivided by miR-200c and miR-203 levels in serum from CRC patients. (A) The overall survival rate of CRC patients with high serum miR-200c expression was significantly lower than that of those with low serum miR-200c expression (P=0.0002; Log-rank test). (B) The overall survival rate of CRC patients with high miR-203 expression in serum was significantly lower than that of those with low miR-203 expression (p<0.0001; Log-rank test).

To further evaluate whether serum miR-200c and miR-203 levels can predict prognosis of CRC, a survival analysis was performed. Kaplan-Meier analysis showed that the patients with higher levels of both miR-200c and miR-203 were significantly poorer survival than those with lower levels of these miRNAs, respectively (miR-200c; $p=0.0002$, miR-203; $p<0.0001$; log-rank test) (FIG. 33A, 33B). The results of univariate and multivariate Cox proportional hazard regression analysis for prognostic indicator are shown in Tables 35 [formerly 3]. In univariate analysis, high levels of both miR-200c and miR-203 in serum ($p=0.0008$, $p<0.0001$), high level of tumor marker CEA ($p=0.0001$), high grade of pathological T stage (T3/4) ($p=0.0024$), lymph node metastasis positive ($p<0.0001$), histological poorly differentiated type ($p=0.036$) and high TNM stage (Stage III/IV) ($p<0.0001$) were significantly associated with poor prognosis. On the other hands, multivariate analysis showed that high levels of serum miR-200c and miR-203 were independent prognostic markers in CRC patients, respectively (miR-200c: HR=2.67, 95% CI=1.28-5.67 $p=0.01$, miR-203: HR=2.40, 95% CI=1.19-4.83, $p=0.015$) (Table 35).

TABLE 34

Uni- and Multivariate analyses for predicting lymph-node metastasis in CRC

| | Univariate | | | Multivariate | | |
|---|---|---|---|---|---|---|
| Variables | HR | 95% CI | p-value | HR | 95% CI | p-value |
| Pathological T stage (T3/4 vs. 1/2) | 6.46 | 2.61-15.96 | 0.0024* | 2.38 | 0.81-7.03 | 0.11 |
| Pathology (poor diff. vs. diff.) | 2 | 0.57-6.98 | 0.2715 | 1.39 | 0.38-5.07 | 0.62 |
| Venous Invasion (positive vs. negative) | 4.59 | 2.13-9.89 | 0.0001* | 1.24 | 0.52-2.96 | 0.62 |
| Lymphatic Invasion (positive vs. negative) | 18.26 | 5.43-61.38 | <0.0001* | 6.56 | 1.55-27.8 | 0.010* |
| CEA (≥5 vs. <5) | 6.25 | 2.45-15.92 | 0.0001* | 2.44 | 1.02-5.84 | 0.044* |
| miR-200c in serum (high vs. low) | 3.61 | 1.85-7.09 | 0.0001* | 4.81 | 1.98-11.7 | 0.0005* |
| miR-203 in serum (high vs. low) | 2.69 | 1.30-5.55 | 0.0064* | 1.37 | 0.55-3.42 | 0.49 |

*$p < 0.05$;
CRC: colorectal cancer;
HR: Hazard Ratio;
CI: Confidence Interval;
CEA: Carcinoembryonic antigen;
diff: differentiation;
TNM: tumor-node-metastasis staging system

TABLE 35

Uni- and Multivariate analyses for prognostic factors in CRC

| Variables | Univariate | | | Multivariate | | |
|---|---|---|---|---|---|---|
| | HR | 95% CI | p-value | HR | 95% CI | p-value |
| Age (≥67 vs. <67) | 0.76 | 0.42-1.35 | 0.35 | — | — | — |
| Gender (Female vs. Male) | 1.02 | 0.56-1.86 | 0.92 | — | — | — |
| Pathological T stage (T3/4 vs. 1/2) | 8.97 | 2.19-36.7 | 0.0024* | 3.63 | 0.82-16.1 | 0.091 |
| Pathology (poor diff. vs. diff.) | 2.26 | 1.05-4.84 | 0.036* | 2.07 | 0.86-4.96 | 0.105 |
| Lymph node metastasis (positive vs. negative) | 17.1 | 6.18-47.8 | <0.0001* | 1.24 | 0.28-5.46 | 0.78 |
| TNM stage (III/IV vs. I/II) | 33.4 | 8.12-136.9 | <0.0001* | 10.2 | 1.27-81.7 | 0.03* |
| CEA (≥5 vs. <5) | 4.84 | 2.15-10.89 | 0.0001* | 1.46 | 0.57-3.74 | 0.43 |
| miR-200c in serum (high vs. low) | 2.84 | 1.55-5.24 | 0.0008* | 2.67 | 1.28-5.67 | 0.01* |
| miR-203 in serum (high vs. low) | 5.38 | 2.98-10.04 | <0.0001* | 2.40 | 1.19-4.83 | 0.015* |

*$p < 0.05$;
CRC: colorectal cancer;
HR: Hazard Ratio;
CI: Confidence Interval;
CEA: Carcinoembryonic antigen;
diff: differentiation;
TNM: tumor-node-metastasis staging system Evaluation of the Sources for miR-200c and miR-203 in Serum with CRC.

Figures 34A, 34B, 34C, 34D:
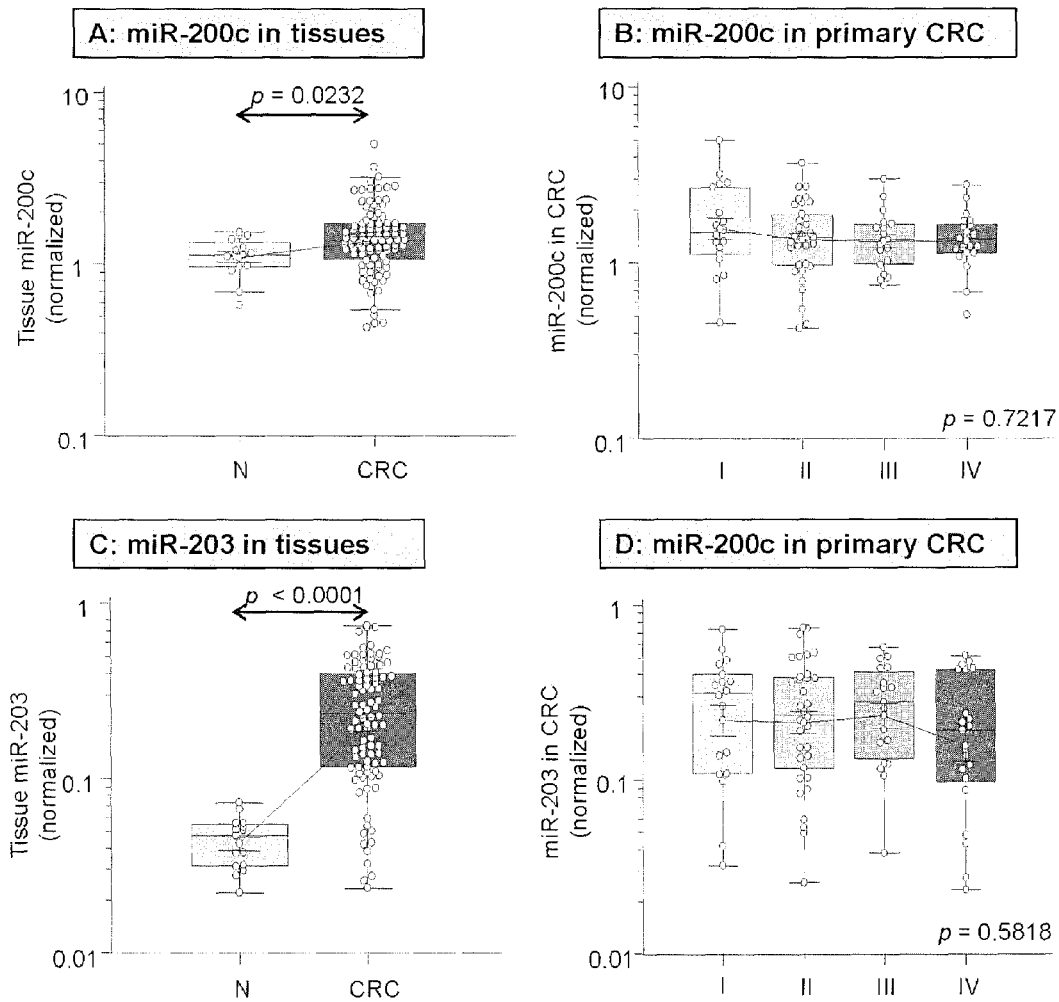
FIGS. 34A-34F—Large-scale validation of miR-200c and miR-203 in primary tumor samples from 92 out of 184 CRC patients. (A) Box plot of tissue miR-200c level across TNM stage. (B) Box plot of tissue miR-200c level across in comparison between stage I-III and stage IV CRC patients. (C) Box plot of tissue miR-203 level across TNM stage. (D) Box plot of tissue miR-203 level across in comparison between stage I-III and stage IV CRC patients. Scatter plot of miR-200c (E) and miR-203 (F) expression correlation between serum and matched primary tumor specimens from CRC patients. There are not any correlation in both miR-200c and miR-203 by Spearman correlation analysis. The Box represents the interquartile range and the line across the box indicates the median value. Expression levels of miR-200c and miR-203 (log 10 scale on the y-axis) are normalized to has-miR-16. Statistically significant differences were determined using Mann-Whiteny tests and Kruskal-Wallis test. The patient number of stage I, II, III and IV is 18, 34, 19 and 21, respectively.
Figures 34E, 34F:
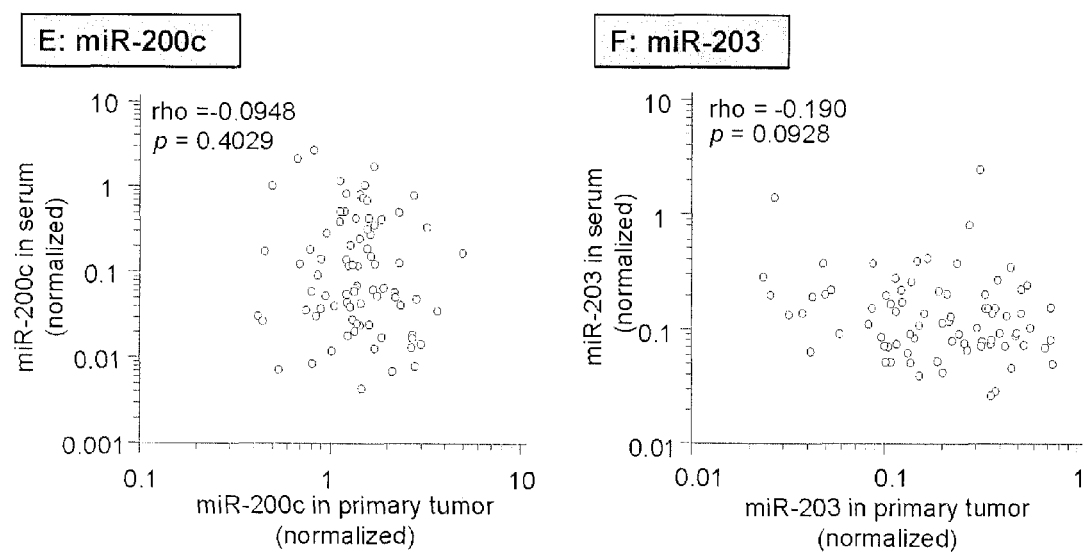

To prove circulating miR-200c and miR-203 in serum are tumor origin, the relationships between the levels of these miRNAs expression in serum and matched primary tumor were first analyzed. It was found that there was a no correlation between primary lesion and serum of these miRNAs expression (miR-200c; FIG. 34A, miR-203; FIG. 34B). In addition, both miR-200c and miR-203 expression in primary tumor were not upregulated in stage IV compared to stage I-III CRC patients (miR-200c; FIG. 34C, miR-203; FIG. 34D). Furthermore, there were no relationships between miR-200c expression in primary tumor and clinicopathological findings such as pathological T stage, tumor size, pathological N stage and distant metastasis (Table 36). In contrast, miR-203 expression levels in tumor with liver metastasis patients were significantly lower than that without liver metastasis (p=0.017) (Table 36). These miRNAs expression were first analyzed in both primary tumors and matched liver metastases from 20 CRC patients. Of interest, the levels of miR-200c in liver metastases were significantly higher than that in primary tumors. Furthermore, miR-200c expression was identified in both primary CRC tumors and their matched liver metastases by in situ hybridization. miR-200c was stained with high intensity in metastases site compared to in matched primary tumors.

TABLE 36

Clinical significances of miR-200c and miR-203 expression levels of primary tumors in CRC

| Factors | | Number | miR-200c (mean ± SD) | p-value | miR-203 (mean ± SD) | p-value |
|---|---|---|---|---|---|---|
| Age | >67 | 48 | 1.62 ± 0.83 | 0.26 | 0.26 ± 0.17 | 0.45 |
| | ≤67 | 44 | 1.44 ± 0.65 | | 0.29 ± 0.19 | |
| Gender | Male | 60 | 1.45 ± 0.62 | 0.45 | 0.27 ± 0.19 | 0.63 |
| | Female | 32 | 1.68 ± 0.94 | | 0.28 ± 0.16 | |
| Tumor size | ≤4 cm | 43 | 1.41 ± 0.65 | 0.18 | 0.31 ± 0.19 | 0.052 |
| | >4 cm | 49 | 1.64 ± 0.81 | | 0.23 ± 0.18 | |
| Serosal invasion | negative | 21 | 1.73 ± 1.05 | 0.64 | 0.28 ± 0.19 | 0.83 |
| | positive | 70 | 1.47 ± 0.63 | | 0.27 ± 0.13 | |
| Lymphatic invasion | negative | 16 | 1.75 ± 1.17 | 0.81 | 0.28 ± 0.23 | 0.73 |
| | positive | 76 | 1.49 ± 0.62 | | 0.27 ± 0.17 | |
| Venous invasion | negative | 45 | 1.60 ± 0.88 | 0.85 | 0.26 ± 0.19 | 0.35 |
| | positive | 47 | 1.47 ± 0.60 | | 0.28 ± 0.18 | |
| Lymph node metastasis | negative | 52 | 1.62 ± 0.87 | 0.41 | 0.29 ± 0.19 | 0.51 |
| | positive | 40 | 1.42 ± 0.53 | | 0.25 ± 0.16 | |
| Liver metastasis | negative | 76 | 1.54 ± 0.78 | 0.8 | 0.29 ± 0.19 | 0.017* |
| | positive | 16 | 1.48 ± 0.55 | | 0.17 ± 0.12 | |
| Peritoneal metastasis | negative | 84 | 1.56 ± 0.76 | 0.14 | 0.26 ± 0.18 | 0.45 |
| | positive | 8 | 1.21 ± 0.60 | | 0.24 ± 0.21 | |
| Distant metastasis | negative | 71 | 1.56 ± 0.80 | 0.69 | 0.28 ± 0.18 | 0.17 |
| | positive | 21 | 1.41 ± 0.50 | | 0.22 ± 0.16 | |

*$p < 0.05$;
CRC: colorectal cancer;
SD: Standard Deviation

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Asangani, et al., *Oncogene.* 27:2128-36, 2008.
Baffa, et al., *J Pathology.* 219:214-21, 2009.
Balaguer, et al., *Cancer Res.* 70:6609-18, 2010.
Balaguer, et al., *Clin Cancer Res.* 17:6239-49, 2011.
Bipat, et al., *Netherlands J. Med.* 65:5-14, 2007.
Bitarte, et al., *Stem Cells.* 29:1661-71, 2011.
Bloomston, et al., *JAMA.* 297:1901-8, 2007.
Burk, et al., *EMBO Rep.* 9:582-9, 2008.
Calin, et al., *Cancer.* 6:857-66, 2006.
Calin, et al., *New England J. Med.* 353:1793-801, 2005.
Chang, et al., *BMC Cancer.* 10:173, 2010.
Chang, et al., *RNA Biol.* 1:106-13, 2004.
Cheng, et al., *PLoS One.* 6:e17745, 2011.
Cortez, et al., *Expert Opin Biol Ther.* 9:703-711, 2009.
Cottonham, et al., *J Biol Chem.* 285:35293-302, 2010.
De Angelis, et al., *Brit J Cancer.* 80:526-35, 1999.
de Krijger, et al., *J Pathol.* 224:438-47, 2011.
Dews, et al., *Nat. Genet.* 38:1060-5, 2006.
Duffy, *Clin Chem.* 47:624-630, 2001.
Duffy, et al., *Eur J Cancer.* 43:1348-60, 2007.
Earle, et al., *J Malec Diagnostics.* 12:433-40, 2010.
Egashira, et al., *Mod Pathol.* 17:503-11, 2004.
Fakih, et al., *Oncology.* 20:579-87, 2006.
Fernandez, et al., *Ann Surg.* 240:438-47; discussion 47-50, 2004.
Gregory, et al., *Nat cell Biol.* 10:593-601, 2008.
Halama, et al., *Anticancer Res.* 28:4111-5, 2008.
Huang, et al., *Int J Cancer.* 127:118-26, 2010.
Hugo, et al., *J Cell Physiol.* 213:374-83, 2007.
Hur, et al., *Gut.* 2012 Jul. 10. [Epub ahead of print].
Hur, et al., *Gut.* doi:10.1136/gutjnl-2011-301846, 2012.
Hur, et al., *Gut.* Doi: 10.1136/gutjnl-2011-301846, 2012.
Japanese Society of Colon of the Colon and Rectum. Japanese Classification of Colorectal Carcinoma. Second English Edition. Kanehara & Co., Ltd., Tokyo 2009.
Kopetz, et al., *J Clin Oncol.* 27:3677-83, 2009.
Kroh, et al., *Methods.* 50:298-301, 2010.
Kulda, et al., *Cancer Genet Cytogenet.* 200:154-60, 2010.
Lanza, et al., *Molecular Cancer.* 6:54, 2007.
Lewis, et al., *Cell.* 120:15-20, 2005.
Lieberman, et al., *Gastroenterology.* 143:844-57, 2012.
Link, et al., *Cancer Epidemiol Biomarkers Prev.* 19:1766-74, 2010.
Lu, et al., *Nature.* 435:834-8, 2005.
Meropol, et al., *J Clin Oncol.* 25:180-6, 2007.
Mitchell, et al., *Proc Natl Acad Sci USA.* 105:10513-8, 2008.
Ng, et al., *Gut.* 58:1375-81, 2009.
Nishida, et al., *Ann Surg Oncology.* 19:3065-71, 2012.
Nishida, et al., *Clin Cancer Res.* 18:3054-70, 2012.
Polyak, et al., *Nat Rev Cancer.* 9:265-73, 2009.
Pu, et al., *J Gastroenterol Hepatol.* 25:1674-80, 2010.
Rees, et al., *Ann Surg.* 247:125-35, 2008.
Reiter, et al., *Anticancer Res.* 20:5195-8, 2000.
Ruopp, et al., *Biom J.* 50:419-30, 2008.
Schetter, et al., *JAMA.* 299:425-36, 2008.
Schetter, et al., *JAMA.* 299:425-36, 2008.
Schimanski, et al., *World J Gastroenterol.* 15:2089-96, 2009.
Siegel R, Naishadham D, Jemal A. Cancer statistics, 2012. *CA Cancer J. Clin.* 2012; 62:10-29.
Siegel, et al., *CA Cancer J. Clin.* 62:10-29, 2012.
Siegel, et al., *CA: a cancer journal for clinicians.* 62:10-29, 2012.
Slaby, et al., *Oncology.* 72:397-402, 2007.
Spaderna, et al., *Gastroenterology.* 131:830-40, 2006.
Sun, et al., *Acta pharmacologica Sinica.* 32:375-84, 2011.
Tan, et al., *Surg Oncol.* 18:15-24, 2009.
Thiery, et al., *Cell.* 139:871-90, 2009.
Thiery, *Nat Rev Cancer.* 2:442-54, 2002.
Tominaga, et al., *Dis Colon Rectum.* 48:92-100, 2005.
van Kouwenhove, et al., *Nat Rev Cancer.* 11:644-56, 2011.
Wang & Gu, *Cancer Epidemiol.* 36:e62-7, 2012.
Wellner, et al., *Nat Cell Biol.* 11:1487-95, 2009.
Yamakuchi, et al., *Proc Natl Acad Sci USA.* 6334-9, 2010.

What is claimed is:

1. A method for treating colorectal cancer in a subject suspected of having or determined to have a colorectal cancer, comprising:
   treating the subject with an adjuvant therapy comprising a chemotherapeutic agent; wherein the subject was determined to have increased expression level of miR-885-5p and increased expression level of one or more of miR-21, miR-200c, and miR-203 in a serum sample from the subject compared to a control or reference level of expression.

2. The method of claim 1, wherein the subject was determined to have increased expression level of miR-885-5p, miR-21, miR-200c, and miR-203 in a serum sample from the subject.

3. The method of claim 1, wherein the subject was determined to have increased expression level of miR-885-5p, miR-21, miR-200c, and miR-203 in a serum sample from the subject compared to a control or reference level of expression by contacting the serum sample with nucleic acid probes that specifically bind to miR-885-5p, miR-21, miR-200c, and miR-203.

4. The method of claim 3, wherein nucleic acids from the subject were amplified.

5. The method of claim 4, wherein the expression level of miR-885-5p, miR-21, miR-200c, and miR-203 in the serum sample from the subject was determined by contacting the amplified nucleic acids with nucleic acid probes for miR-885-5p, miR-21, miR-200c, and miR-203.

6. The method of claim 1, wherein the subject was determined to have increased expression level of miR-885-5p, miR-21, miR-200c, and miR-203 in a serum sample from the subject by PCR amplification of nucleic acids in the serum sample from the subject, followed by detection of the level of amplification of miR-885-5p, miR-21, miR-200c, and miR-203.

7. The method of claim 1, wherein the chemotherapeutic agent comprises one or more of cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin or methotrexate.

8. The method of claim 1, wherein the chemotherapeutic agent comprises 5-fluorouracil.

9. The method of claim 1, wherein the subject has previously been diagnosed with colorectal cancer.

* * * * *

UNITED STATES PATENT AND TRADEMARK OFFICE
CERTIFICATE OF CORRECTION

PATENT NO. : 9,868,992 B2
APPLICATION NO. : 14/215959
DATED : January 16, 2018
INVENTOR(S) : Goel et al.

It is certified that error appears in the above-identified patent and that said Letters Patent is hereby corrected as shown below:

In the Specification

Column 1, Line 11, delete the entire paragraph beginning "The invention was made..." and replace with the following:
--STATEMENT OF FEDERALLY FUNDED RESEARCH
This invention was made with government support under Grant Nos. R01 CA072851 and R01 CA129286 awarded by the National Institutes of Health (NIH). The government has certain rights in the invention.-- therefore.

Signed and Sealed this
Fifteenth Day of May, 2018

Andrei Iancu
*Director of the United States Patent and Trademark Office*